(12) United States Patent
Sugawara et al.

(10) Patent No.: US 11,696,500 B2
(45) Date of Patent: Jul. 4, 2023

(54) ORGANIC ELECTROLUMINESCENT ELEMENT, DISPLAY DEVICE, ILLUMINATION DEVICE, AND PI-CONJUGATED COMPOUND

(71) Applicant: Konica Minolta, Inc., Tokyo (JP)

(72) Inventors: Ryutaro Sugawara, Tokyo (JP); Takatugu Suzuki, Tokyo (JP)

(73) Assignee: MERCK PATENT GMBH, Darmstadt (DE)

( * ) Notice: Subject to any disclaimer, the term of this patent is extended or adjusted under 35 U.S.C. 154(b) by 267 days.

(21) Appl. No.: 16/309,245

(22) PCT Filed: Jun. 26, 2017

(86) PCT No.: PCT/JP2017/023364
§ 371 (c)(1),
(2) Date: Dec. 12, 2018

(87) PCT Pub. No.: WO2018/008442
PCT Pub. Date: Jan. 11, 2018

(65) Prior Publication Data
US 2019/0334097 A1    Oct. 31, 2019

(30) Foreign Application Priority Data
Jul. 8, 2016    (JP) .................. 2016-135999

(51) Int. Cl.
*H10K 85/60* (2023.01)
*H10K 50/11* (2023.01)
(Continued)

(52) U.S. Cl.
CPC ....... *H10K 85/6572* (2023.02); *H10K 85/653* (2023.02); *H10K 85/654* (2023.02);
(Continued)

(58) Field of Classification Search
None
See application file for complete search history.

(56) References Cited

U.S. PATENT DOCUMENTS

2012/0319567 A1* 12/2012 Uetani .......................... 313/504
2013/0082909 A1*  4/2013 Miura ............................. 345/76
(Continued)

FOREIGN PATENT DOCUMENTS

| JP | 2013116975 A | 6/2013 |
|----|--------------|--------|
| JP | 2016210913 A | 12/2016 |
| WO | 2016042070 A1 | 3/2016 |

OTHER PUBLICATIONS

Takahashi et al., "Donor-acceptor-structured 1,4-diazatriphenylene derivatives exhibiting thermally activated delayed fluorescence: design and synthesis, photophysical properties and OLED characteristics", Sci. Technol. Adv. Mater. 2014, vol. 15, p. 034202-1-10 (Year: 2014).*

(Continued)

*Primary Examiner* — Dylan C Kershner
*Assistant Examiner* — Seokmin Jeon
(74) *Attorney, Agent, or Firm* — Lucas & Mercanti, LLP

(57) ABSTRACT

The purpose of the present invention is to provide: a π-conjugated compound exhibiting excellent light emission characteristics; an organic electroluminescent element using same; a display device; and an illumination device. Accordingly, this organic electroluminescent element is provided with: a positive electrode; a negative electrode; and at least one organic layer which is sandwiched between the positive electrode and the negative electrode, and which includes a light emission layer. The light emission layer includes a π-conjugated compound having a structure represented by any of general formulae (1)-(3)

(Continued)

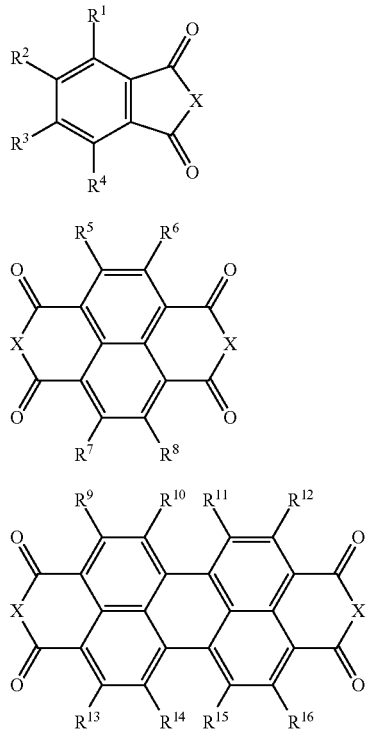

General formula 1

General formula 2

General formula 3

(in general formulae (1)-(3), at least one among R1-R4, R5-R8, and R9-R16 represents a group represented by general formula (4)

General formula 4

(in general formula (4): Ar1 and Ar2 represent substituted or unsubstituted aryl groups; L1 represents a single bond or a substituted or unsubstituted arylene group; and # represents a bond to general formulae (1)-(3))).

8 Claims, 10 Drawing Sheets

(51) Int. Cl.
| | |
|---|---|
| *H10K 50/15* | (2023.01) |
| *H10K 50/16* | (2023.01) |
| *H10K 101/10* | (2023.01) |

(52) U.S. Cl.
CPC ....... *H10K 85/656* (2023.02); *H10K 85/6574* (2023.02); *H10K 50/11* (2023.02); *H10K 50/15* (2023.02); *H10K 50/16* (2023.02); *H10K 2101/10* (2023.02)

(56) References Cited

U.S. PATENT DOCUMENTS

| | | | |
|---|---|---|---|
| 2016/0087221 A1* | 3/2016 | Liu | H01L 51/0061 |
| 2017/0062731 A1* | 3/2017 | Ogiwara | H01L 51/0072 |
| 2017/0309858 A1* | 10/2017 | Omata | H01L 51/5044 |

OTHER PUBLICATIONS

Screen shot of Merriam-Webster dictionary to show definition of "apparatus"; https://www.merriam-webster.com/dictionary/apparatus (Year: 2020).*
English translation of CN 101665492 A and the original CN 101665492 A, Liu Di, Mar. 10, 2010 (Year: 2010).*
Rybakiewicz et al. "Electronic properties of semiconducting naphthalene bisimide derivatives—Ultraviolet photoelectron spectroscopy versus electrochemistry", Electrochimica Acta, 2013, vol. 96, p. 13-17 (Year: 2013)*
Yuki Shibano et al. "Organic Thin-Film Solar Cells Using Electron-Donating Perylene Tetracarboxylic Acid Derivatives", J. Phys. Chem. C, 2009, vol. 113, p. 15454-15466 (Year: 2009).*
Ashok Keerthi et al. "Regioisomers of Perylenediimide: Synthesis, Photophysical, and Electrochemical Properties" J. Phys. Chem. B, 2012, vol. 116, p. 4603-4614 (Year: 2012).*
K. Chen, et al; Highly soluble monoamino-substituted perylen tetracarboxylic dianhydrides: synthesis, optical and electrochemical properties; Int. J. Mol. Sci.; 2014; vol. 15; pp. 22642-22660.
P. Ranke, et al; Electroluminescence and electron transport in a perylene dye; Applied Physics Letters; 1997; vol. 71; No. 10; pp. 1332-1334.
H. Uoyama, et al; Highly efficient organic light-emitting diodes from delayed fluorescence; Nature; 2012; vol. 492; pp. 234-238.
H. Nakanotani, et al; High-efficiency organic light-emitting diodes with fluorescent emitters; Nature Communication; 2014; vol. 5; pp. 4016-4022.
M.E. Jang, et al; Organic light-emitting diodes based on donor-substituted phthalimide and maleimide fluorophores; Chemistry Letters; vol. 44; No. 9; 2015; pp. 1248-1250.
H. Patil, et al; Donor-acceptor-donor modular small organic molecules based on the naphthalene diimide acceptor unit for solution-processable photovoltaic devices; Journal of Electronic Materials; vol. 43; No. 9; 2014; pp. 3243-3254.
M. Shi, et al; Synthesis and photovoltaic properties of perylene diimide derivatives with aryl electron-donating substitutes at bay positions; Gongneng Cailiao; vol. 43; No. 9; 2012; pp. 1122-1129.
International Search Report dated Sep. 5, 2017 for PCT/JP2017/023364 and English translation.
Written Opinion of International Searching Authority dated Sep. 5, 2017 from the corresponding International Application No. PCT/JP2017/023364 and English translation.
JPO, Office Action for the corresponding Japanese patent application No. 2018-526039, dated Mar. 30, 2021, with English translation.

* cited by examiner

ORGANIC ELECTROLUMINESCENT ELEMENT, DISPLAY DEVICE, ILLUMINATION DEVICE, AND PI-CONJUGATED COMPOUND

CROSS REFERENCE TO RELATED APPLICATION

This Application is a 371 of PCT/JP2017/023364 filed on Jun. 26, 2017 which, in turn, claimed the priority of Japanese Patent Application No. 2016-135999 filed on Jul. 8, 2016, both applications are incorporated herein by reference.

TECHNICAL FIELD

The present invention relates to an organic electroluminescent element, a display apparatus, a lighting apparatus, and a π-conjugated compound. Particularly, the present invention relates to an organic electroluminescent element having excellent emission efficiency and lifetime, a π-conjugated compound to be used in the organic electroluminescent element, and a display apparatus and a lighting apparatus including the organic electroluminescent element.

BACKGROUND ART

Organic EL elements (also referred to as "organic electroluminescence light emitting elements"), which employ electroluminescence of organic materials (hereinafter referred to as "EL"), have already been put into practice as novel light-emitting systems capable of planar light emission. Organic EL elements have recently been employed in electronic displays and also in lighting apparatuses, and development of such organic EL elements is progressing. Particularly, various investigations have been targeted on hole transport materials, electron transport materials, light-emitting materials, and the like that constitute organic EL elements to develop techniques to improve the emission efficiency. Of these, studies on organic EL elements that employ a compound having a carboxylic diimide structure or a carboxylic anhydride structure have been reported.

For example, NPL 1 describes a perylenetetracarboxylic dianhydride substituted by an alkylamino group represented by the following structure. NPL 1 also mentions that use of the compound in the light-emitting layer of an organic EL element provides red color emission.

[Formula 1]

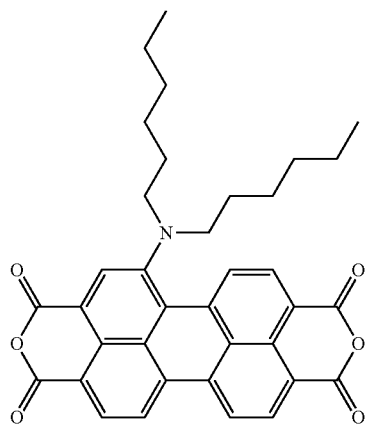

NLP 2 describes a perylenecarboxylic diimide compound substituted by phenoxy groups represented by the following structure. NLP 2 also mentions that use of the compound in the light-emitting layer of an organic EL element provides red color emission.

[Formula 2]

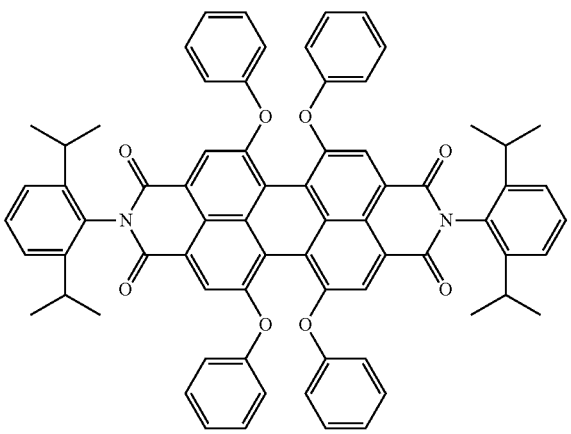

Meanwhile, it has been reported recently that some π-conjugated compounds undergo crossing from the triplet excited state, which has a lower energy level, to the singlet excited state, which has a higher energy level (reverse intersystem crossing) depending on the Joule heat during emission of an organic EL element and/or the ambient temperature (see e.g., PTL 1, NPL 3, NPL 4, and the like). Occurrence of such reverse intersystem crossing can achieve fluorescence at substantially 100% (also referred to as "thermally activated delayed fluorescence, hereinbelow, also referred to as "TADF"), and thus, development of light-emitting materials exhibiting the TADF property has been required.

CITATION LIST

Patent Literature

PTL 1
Japanese Patent Application Laid-Open No. 2013-116975

Non-Patent Literature

NPL 1
Kew-Yu Chen, Che-Wei Chang, Int. J. Mol. Sci. 2014, 15, 22642-22660
NPL 2
H. W. Schmidt et al., Appl. Phys. Lett. 2014, 71, 1332-1334
NPL 3
H. Uoyama, et al., Nature, 2012, 492, 234-238
NPL 4
H. Nakanotani, et al., Nature Communication, 2014, 5, 4016-4022

SUMMARY OF INVENTION

Technical Problem

As mentioned above, from the viewpoint of improving the performance of organic EL elements, light-emitting materials and the like having high emission efficiency have been required. In NPL 1 and NPL 2, the perylenetetracarboxylic dianhydride substituted by an alkylamino group and the perylenecarboxylic diimide compound substituted by phenoxy groups are described as red light-emitting materials. However, when the present inventors have evaluated the emission characteristics of these compounds, the compounds exhibited insufficient performance as light-emitting materials. Also, as mentioned above, from the viewpoint of the emission efficiency and the like of organic EL elements, development of compounds exhibiting the TADF property has been required, but neither of the compounds in NPL 1 nor NPL 2 exhibited the TADF property.

The present invention has been made in view of the above problems. That is, an object of the present invention is to provide a π-conjugated compound having excellent emission characteristics, and an organic EL element, a display apparatus, a lighting apparatus, and the like including the compound.

Solution to Problem

The present inventors have made various investigations on many π-conjugate compound groups having a carboxylic anhydride structure and a carboxylic diimide structure with an intention of providing light-emitting materials having excellent emission characteristics. As a result, the present inventors have newly found that compounds produced by introducing a diarylamino group into a π-conjugate compound group having a specific carboxylic anhydride structure and a carboxylic diimide structure have high emission efficiency and a long emission lifetime, having led to the present invention.

The problems according to the present invention described above are solved by the following aspects:

[1] An organic electroluminescent element comprising an anode, a cathode, and an organic layer including a light-emitting layer sandwiched between the anode and the cathode, in which the light-emitting layer comprises a π-conjugated compound having a structure represented by any of the following general formulas 1 to 3:

[Formula 3]

General formula 1

[Structure of general formula 1 showing substituted phthalic anhydride/imide with $R^1$, $R^2$, $R^3$, $R^4$ and X]

General formula 2

[Structure of general formula 2 showing naphthalene diimide/dianhydride with $R^5$, $R^6$, $R^7$, $R^8$ and X]

General formula 3

[Structure of general formula 3 showing perylene diimide/dianhydride with $R^9$ to $R^{16}$ and X]

in which X's each independently represent O or $NR^{17}$, and $R^1$ to $R^{17}$ each independently represent a hydrogen atom or a substituent; provided that at least one of $R^1$ to $R^4$, at least one of $R^5$ to $R^8$, or at least one of $R^9$ to $R^{16}$ represents a group represented by the following general formula 4:

[Formula 4]

General formula 4

$$\begin{array}{c} Ar^1 \\ \phantom{Ar}\diagdown \\ \phantom{Arm}N—L^1—\# \\ \phantom{Ar}\diagup \\ Ar^2 \end{array}$$

in which $Ar^1$ and $Ar^2$ each independently represent a substituted or unsubstituted aryl group, $L^1$ represents a single bond or a substituted or unsubstituted arylene group, and # represents a bonding to the general formulas 1 to 3; and $Ar^1$ and $Ar^2$ may form a ring structure via a single bond or a crosslinking group.

[2] The organic electroluminescent element according to [1], in which, in the general formulas 1 to 3, at least two of $R^1$ to $R^4$, at least two of $R^5$ to $R^8$, or at least two of $R^9$ to $R^{16}$ represent a group represented by the general formula 4.

[3] The organic electroluminescent element according to [1] or [2], in which, in the general formula 4, $L^1$ is an unsubstituted phenylene group.

[4] The organic electroluminescent element according to any one of [1] to [3], in which the group represented by the general formula 4 is a group represented by any of the following general formulas 5 to 8:

[Formula 5]

General formula 5

[Structure of general formula 5 showing triarylamine with $R^{18}$ to $R^{27}$ and $L^2$]

-continued

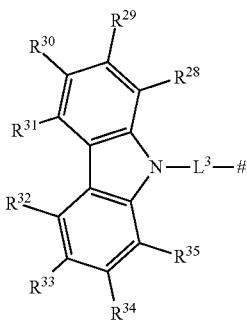
General formula 6

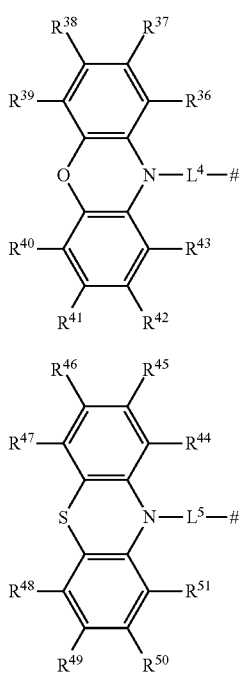
General formula 7

General formula 8 in which $L^2$ to $L^5$ each independently represent a single bond or a substituted or unsubstituted arylene group, # represents a bonding to the general formulas 1 to 3, and $R^{18}$ to $R^{27}$, $R^{28}$ to $R^{35}$, $R^{36}$ to $R^{43}$, and $R^{44}$ to $R^{51}$ each independently represent a hydrogen atom or a substituent; and $R^{18}$ and $R^{19}$, $R^{19}$ and $R^{20}$, $R^{20}$ and $R^{21}$, $R^{21}$ and $R^{22}$, $R^{23}$ and $R^{24}$, $R^{24}$ and $R^{25}$, $R^{25}$ and $R^{26}$, $R^{26}$ and $R^{27}$, $R^{28}$ and $R^{29}$, $R^{29}$ and $R^{30}$, $R^{30}$ and $R^{31}$, $R^{32}$ and $R^{33}$, $R^{33}$ and $R^{34}$, $R^{34}$ and $R^{35}$, $R^{36}$ and $R^{37}$, $R^{37}$ and $R^{38}$, $R^{38}$ and $R^{39}$, $R^{40}$ and $R^{41}$, $R^{41}$ and $R^{42}$, $R^{42}$ and $R^{43}$, $R^{44}$ and $R^{45}$, $R^{45}$ and $R^{46}$, $R^{46}$ and $R^{47}$, $R^{48}$ and $R^{49}$, $R^{49}$ and $R^{50}$, $R^{50}$ and $R^{51}$ may be bonded to each other to form a cyclic structure.

[5] The organic electroluminescent element according to any one of [1] to [4], in which $\Delta E_{ST}$ of the π-conjugated compound is 0.50 eV or less, the $\Delta E_{ST}$ being an absolute value of difference between the lowest singlet excited energy level and the lowest triplet excited energy level of the compound.

[6] The organic electroluminescent element according to any one of [1] to [5], in which the light-emitting layer comprises the π-conjugated compound and at least one of a fluorescence-emitting compound and a phosphorescence-emitting compound.

[7] The organic electroluminescent element according to any one of [1] to [5], in which the light-emitting layer comprises the π-conjugated compound, at least one of a fluorescence-emitting compound and a phosphorescence-emitting compound, and a host compound.

[8] A display apparatus comprising the organic electroluminescent element according to any one of [1] to [7].

[9] A lighting apparatus comprising the organic electroluminescent element according to any one of [1] to [7].

[10] A π-conjugated compound, in which $\Delta E_{ST}$ of the π-conjugated compound is 0.50 eV or less, the $\Delta E_{ST}$ being an absolute value of difference between the lowest singlet excited energy level and the lowest triplet excited energy level of the compound, and the compound comprises a structure represented by the following general formulas 1 to 3:

[Formula 6]

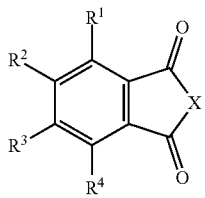
General formula 1

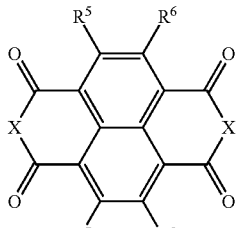
General formula 2

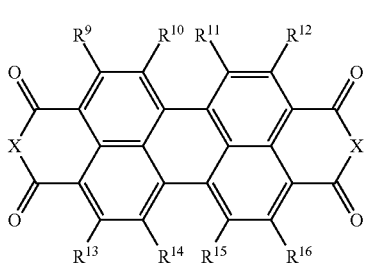
General formula 3 wherein X's each independently represent O or $NR^{17}$, and $R^1$ to $R^{17}$ each independently represent a hydrogen atom or a substituent; provided that at least one of $R^1$ to $R^4$, at least one of $R^5$ to $R^8$, or at least one of $R^9$ to $R^{16}$ represents a group represented by the following general formula 4:

[Formula 7]

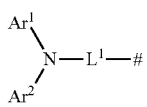
General formula 4 in which $Ar^1$ and $Ar^2$ each independently represent a substituted or unsubstituted aryl group, $L^1$ represents a single bond or a substituted or unsubstituted arylene group, and # represents a bonding to the general formulas 1 to 3; and $Ar^1$ and $Ar^2$ may form a ring structure via a single bond or a crosslinking group.

Advantageous Effects of Invention

According to the present invention, it is possible to obtain a π-conjugated compound having satisfactory emission efficiency and a long lifetime, an organic EL element including the compound, and furthermore, a lighting apparatus, a display apparatus, and the like including the organic EL element.

DESCRIPTION OF EMBODIMENTS

Figure 1A:
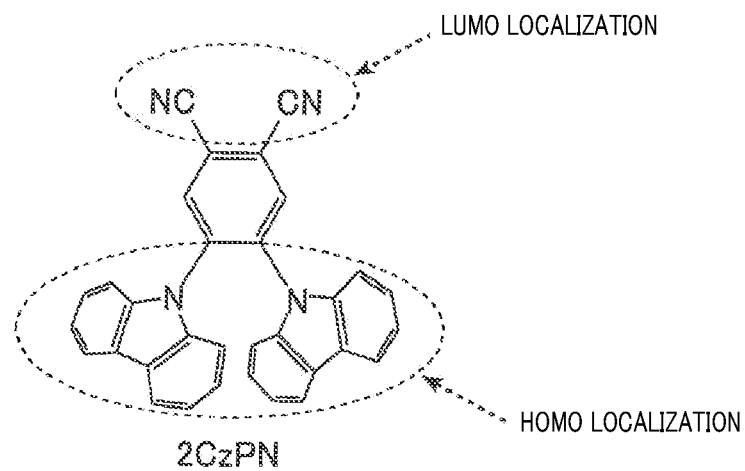
FIG. 1A is a chemical formula of a TADF compound and FIG. 1B is a schematic illustration of an energy diagram of the TADF compound.

Hereinafter, the present invention and components thereof, and embodiments and aspects for carrying out the present invention will be explained in detail. Herein, "to" between numerical values is used to mean to include the numerical values described before and after "to" as the lower limit and the upper limit.

The present inventors have found that use of a π-conjugated compound obtained by introducing a diarylamino group represented by the following general formula 4 into a structure represented by any of the following general formulas 1 to 3 in a light-emitting layer can improve the emission efficiency of an organic EL element and extend the lifetime of the element.

[Formula 8]

General formula 1

[structure showing benzene ring with $R^1$, $R^2$, $R^3$, $R^4$ substituents and two C=O groups connected via X]

General formula 2

[naphthalene diimide/anhydride structure with $R^5$, $R^6$, $R^7$, $R^8$ substituents, X groups, and C=O groups]

General formula 3

[perylene diimide/anhydride structure with $R^9$, $R^{10}$, $R^{11}$, $R^{12}$, $R^{13}$, $R^{14}$, $R^{15}$, $R^{16}$ substituents, X groups, and C=O groups]

In the above general formulas 1 to 3, X's each independently represent O or $NR^{17}$, and $R^1$ to $R^{17}$ each independently represent a hydrogen atom or a substituent. In this case, at least one of $R^1$ to $R^4$, at least one of $R^5$ to $R^8$, or at least one of $R^9$ to $R^{16}$ represents a diarylamino group represented by the following general formula 4.

[Formula 9]

General formula 4

$$Ar^1\!\!\diagdown\!\!N\!\!-\!\!L^1\!\!-\!\!\#$$
$$Ar^2\!\!\diagup$$

In the above general formula 4, $Ar^1$ and $Ar^2$ each independently represent a substituted or unsubstituted aryl group. $Ar^1$ and $Ar^2$ may form a ring structure via a single bond or a crosslinking group. Meanwhile, $L^1$ represents a single bond or a substituted or unsubstituted arylene group, and # represents a bonding to the general formulas 1 to 3.

The mechanism of development or mechanism of action of the effect of the present invention has not been clarified but is assumed as follows. In the π-conjugated compound of the present invention, a diarylamino group is bonded to the aromatic ring of an aromatic carboxylic anhydride structure or an aromatic imide structure, which is to be the main skeleton. Thus, these π-conjugated systems are further expanded to thereby form a structure having a high planarity. The non-radiative deactivation of the π-conjugated compound is herein caused by change in the molecular structure due to the excited energy or change of the excited energy into vibration energy, but in the above π-conjugated compound, of which molecule has high planarity, these changes are difficult to occur. Accordingly, in the π-conjugated compound of the present invention, non-radiative deactivation is unlikely to occur, and thus, high emission efficiency can be achieved.

Additionally, the π-conjugated compound of the present invention has a bipolar ability because of having an electron-accepting carboxylic anhydride structure or carboxylic diimide structure and an electron-donating diarylamino group. Accordingly, use of the above π-conjugated compound in the light-emitting layer of an organic EL element enables efficient transport of charges. It is assumed that the emission efficiency of the organic EL element is consequently enhanced to thereby extend the lifetime of the element. Hereinbelow, the π-conjugated compound of the present invention will be described.

<π-Conjugated Compound>

The π-conjugated compound of the present invention has a structure represented by any of the following general formulas 1 to 3.

[Formula 10]

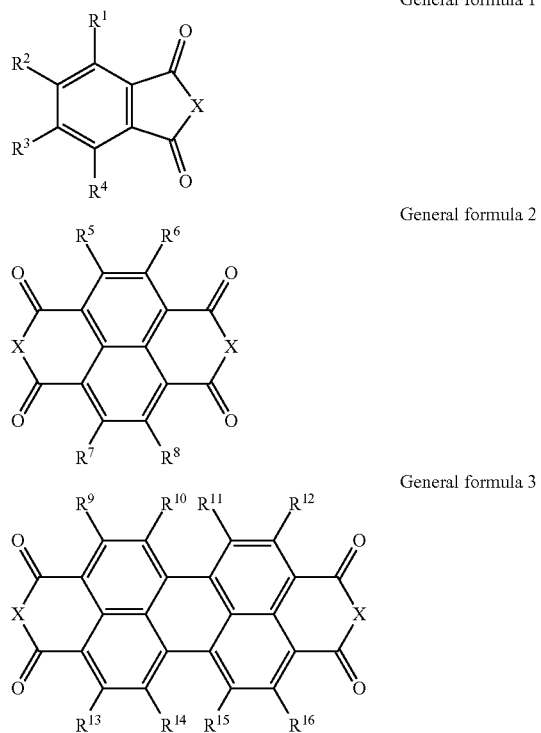

General formula 1

General formula 2

General formula 3

As mentioned above, in the above general formulas 1 to 3, X's each independently represent O or $NR^{17}$, and $R^1$ to $R^{17}$ each independently represent a hydrogen atom or a substituent. In this case, at least one of $R^1$ to $R^4$, at least one of $R^5$ to $R^8$, or at least one of $R^9$ to $R^{16}$ represents a group represented by general formula 4 described below, and two or more groups represented by general formula 4 are preferably contained. When the above π-conjugated compound contains two or more groups represented by general formula 4 per molecule, the absolute value of the difference between the lowest singlet excited energy level and the lowest triplet excited energy level, $\Delta E_{ST}$, is likely to be smaller, and thus, the TADF property is more likely to be developed. Furthermore, the emission efficiency is likely to increase when the π-conjugated compound is used in the light-emitting layer of the organic EL element.

In general formulas 1 to 3, examples of the substituent represented by $R^1$ to $R^{17}$ include an alkyl group (e.g., methyl group, ethyl group, propyl group, isopropyl group, tert-butyl group, pentyl group, hexyl group, octyl group, dodecyl group, tridecyl group, tetradecyl group, pentadecyl group, and the like), cycloalkyl group (e.g., cyclopentyl group, cyclohexyl group, and the like), alkenyl group (e.g., vinyl group, allyl group, and the like), alkynyl group (e.g., ethynyl group, propargyl group, and the like), aromatic hydrocarbon group (also referred to as an aromatic carbon ring group, aromatic carbon ring group, aryl group, or the like; e.g., phenyl group, p-chlorophenyl group, mesityl group, tolyl group, xylyl group, naphthyl group, anthryl group, azulenyl group, acenaphthenyl group, fluorenyl group, phenanthryl group, indenyl group, pyrenyl group, biphenyryl group, and the like), aromatic heterocyclic ring group (e.g., pyridyl group, pyrimidinyl group, furyl group, pyrrolyl group, imidazolyl group, benzimidazolyl group, pyrazolyl group, pyrazinyl group, triazolyl group (e.g., 1,2,4-triazol-1-yl group, 1,2,3-triazol-1-yl, and the like), oxazolyl group, benzoxazolyl group, thiazolyl group, isoxazolyl group, isothiazolyl group, furazanyl group, thienyl group, quinolyl group, benzofuryl group, dibenzofuryl group, benzothienyl group, dibenzothienyl group, indolyl group, carbazolyl group, carbolinyl group, diazacarbazolyl group (a group in which a certain carbon atom constituting the carboline ring of the carbolinyl group is substituted with a nitrogen atom), quinoxalinyl group, pyridazinyl group, triazinyl group, quinazolinyl group, phthalazinyl group, and the like), heterocyclic group (e.g., pyrrolidyl group, imidazolidyl group, morpholyl group, oxazolidyl group, and the like), alkoxy group (e.g., methoxy group, ethoxy group, propyloxy group, pentyloxy group, hexyloxy group, octyloxy group, dodecyloxy group, and the like), cycloalkoxy group (e.g., cyclopentyloxy group, cyclohexyloxy group, and the like), aryloxy group (e.g., phenoxy group, naphthyloxy group, and the like), alkylthio group (e.g., methylthio group, ethylthio group, propylthio group, pentylthio group, hexylthio group, octylthio group, dodecylthio group, and the like), cycloalkylthio group (e.g., cyclopentylthio group, cyclohexylthio group, and the like), arylthio group, (e.g., phenylthio group, naphthylthio group, and the like), alkoxycarbonyl group (e.g., methyloxycarbonyl group, ethyloxycarbonyl group, butyloxycarbonyl group, octyloxycarbonyl group, dodecyloxycarbonyl group, and the like), aryloxycarbonyl group (e.g., phenyloxycarbonyl group, naphthyloxycarbonyl group, and the like), sulfamoyl group (e.g., aminosulfonyl group, methylaminosulfonyl group, dimethylaminosulfonyl group, butylaminosulfonyl group, hexylaminosulfonyl group, cyclohexylaminosulfonyl group, octylaminosulfonyl group, dodecylaminosulfonyl group, phenylaminosulfonyl group, naphthylaminosulfonyl group, 2-pyridylaminosulfonyl group, and the like), acyl group (e.g., acetyl group, ethylcarbonyl group, propylcarbonyl group, pentylcarbonyl group, cyclohexylcarbonyl group, octylcarbonyl group, 2-ethylhexylcarbonyl group, dodecylcarbonyl group, phenylcarbonyl group, naphthylcarbonyl group, pyridylcarbonyl group, and the like), acyloxy group (e.g., acetyloxy group, ethylcarbonyloxy group, butylcarbonyloxy group, octylcarbonyloxy group, dodecylcarbonyloxy group, phenylcarbonyloxy group, and the like), amido group (e.g., methylcarbonylamino group, ethylcarbonylamino group, dimethylcarbonylamino group, propylcarbonylamino group, pentylcarbonylamino group, cyclohexylcarbonylamino group, 2-ethylhexylcarbonylamino group, octylcarbonylamino group, dodecylcarbonylamino group, phenylcarbonylamino group, naphthylcarbonylamino group, and the like), carbamoyl group (e.g., aminocarbonyl group, methylaminocarbonyl group, dimethylaminocarbonyl group, propylaminocarbonyl group, pentylaminocarbonyl group, cyclohexylaminocarbonyl group, octylaminocarbonyl group, 2-ethylhexylaminocarbonyl group, dodecylaminocarbonyl group, phenylaminocarbonyl group, naphthylaminocarbonyl group, 2-pyridylaminocarbonyl group, and the like), ureido group (e.g., methylureido group, ethylureido group, pentylureido group, cyclohexylureido group, octylureido group, dodecylureido group, phenylureido group, naphthylureido group, 2-pyridylaminoureido group, and the like), sulfinyl group (e.g., methylsulfinyl group, ethylsulfinyl group, butylsulfinyl group, cyclohexylsulfinyl group, 2-ethylhexylsulfinyl group, dodecylsulfinyl group, phenylsulfinyl group, naphthylsulfinyl group, 2-pyridylsulfinyl group, and the like), alkylsulfonyl group (e.g., methylsulfonyl group, ethylsulfonyl group, butylsulfonyl group, cyclohexylsulfonyl group, 2-ethylhexylsulfonyl group, dodecylsulfonyl group, and the like), arylsulfonyl group or heteroarylsulfonyl group (e.g., phenylsulfonyl group, naphthylsulfonyl group, 2-pyridylsulfonyl group, and the like), amino group (e.g., amino group, ethylamino group, dimethylamino group, diphenylamino group, butylamino group, cyclopentylamino group, 2-ethylhexylamino group, dodecylamino group, anilino group, naphthylamino group, 2-pyridylamino group, and the like), halogen atom (e.g., fluorine atom, chlorine atom, bromine atom, and the like), fluorinated hydrocarbon group (e.g., fluoromethyl group, trifluoromethyl group, pentafluoroethyl group, pentafluorophenyl group, and the like), cyano group, nitro group, hydroxy group, mercapto group, silyl group (e.g., trimethylsilyl group, triisopropylsilyl group, triphenylsilyl group, phenyldiethylsilyl group, and the like), phosphono group, and the like.

In general formulas 1 to 3, preferred examples of the substituent represented by $R^1$ to $R^{17}$ include $C_{1-18}$ alkyl groups, aromatic hydrocarbon groups having 5 to 12 aromatic ring atoms, aromatic heterocyclic group having 5 to 12 aromatic ring atoms, $C_{1-18}$ is alkoxy groups, and a cyano group. The above substituent represented by $R^1$ to $R^{17}$ may be further substituted by the substituents described above. In general formulas 1 to 3, when two or more substituents are included in a molecule, the substituents may be the same or different.

[Formula 11]

General formula 4

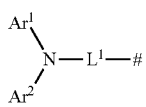

The above general formula 4 is a group to be bonded to the group represented by $R^1$ to $R^{17}$ in the π-conjugated compound represented by general formulas 1 to 3 mentioned above, wherein $Ar^1$ and $Ar^2$ each independently represent a substituted or unsubstituted aryl group. $Ar^1$ and $Ar^2$ may form a ring structure via a single bond or a crosslinking group. Meanwhile, $L^1$ represents a single bond or a substituted or unsubstituted arylene group, and # represents a bonding to the general formulas 1 to 3.

In general formula 4, examples of the aryl groups represented by $Ar^1$ and $Ar^2$ include a benzene ring, biphenyl ring, naphthalene ring, anthracene ring, phenanthrene ring, pyrene ring, chrysene ring, naphthacene ring, triphenylene ring, o-terphenyl ring, m-terphenyl ring, p-terphenyl ring, acenaphthene ring, coronene ring, fluorene ring, fluoranthrene ring, naphthacene ring, pentacene ring, perylene ring, pentaphene ring, picene ring, pyrene ring, pyranthrene ring, anthranthrene ring, and the like. Of these, a benzene ring, biphenyl ring, and naphthalene ring are preferred.

The total number of the substituents to be bonded to the aryl groups represented by $Ar^1$ and $Ar^2$ are not particularly limited. When the total number of the substituents to be bonded to $Ar^1$ and $Ar^2$ is two or more, these substituents may be the same or different from each other. The substituent to be bonded to $Ar^1$ and $Ar^2$ can be the same as the substituents represented by $R^1$ to $R^{17}$ in general formulas 1 to 3. When $Ar^1$ is bonded to $Ar^2$ via a crosslinking group, the crosslinking group is not particularly limited as long as the group is a divalent group having a linking chain length of one atom. Preferred examples of the crosslinking group include an O atom, N atom, S atom, and C atom. Of these, the crosslinking group is preferably an O atom or S atom.

In general formula 4, examples of the arylene group represented by $L^1$ include a phenylene group, biphenylene group, naphthalenylene group, fluorenylene group, and triphenylenylene group. Of these, from the viewpoint of the planarity of the molecule is likely to increase, a phenylene group and biphenylene group are preferred, and an unsubstituted phenylene group is particularly preferred. When a substituent is bonded to the arylene group represented by $L^1$, the substituent can be the same as the substituents represented by $R^1$ to $R^{17}$ in general formulas 1 to 3.

The group represented by the above general formula 4 herein is particularly preferably a group represented by any of the following general formulas 5 to 8.

[Formula 12]

General formula 5

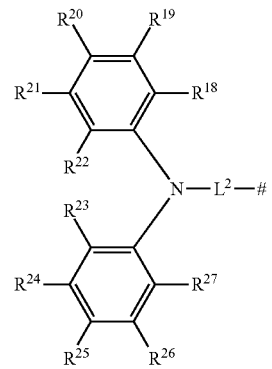

General formula 6

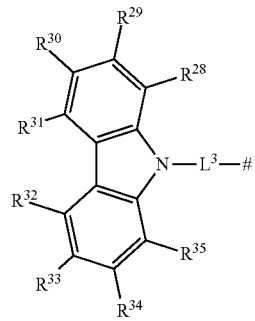

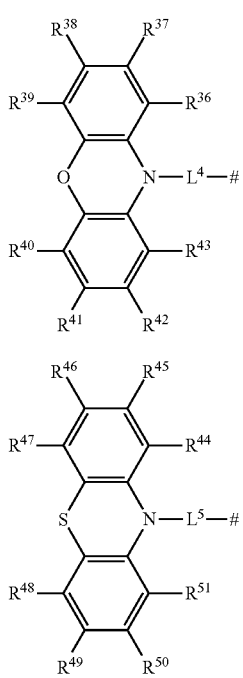

General formula 7

General formula 8

In general formulas 5 to 8, $L^2$ to $L^5$ each independently represent a single bond or a substituted or unsubstituted arylene group and can be the same group as $L^2$ in general formula 4 mentioned above. # represents a bonding to the general formulas 1 to 3.

$R^{18}$ to $R^{27}$, $R^{28}$ to $R^{35}$, $R^{36}$ to $R^{43}$, and $R^{44}$ to $R^{51}$ in general formulas 5 to 8 each independently represent a hydrogen atom or a substituent, and when these are substituents, the substituents can be the same as the substituents represented by $R^1$ to $R^{17}$ in general formulas 1 to 3. $R^{18}$ to $R^{27}$, $R^{28}$ to $R^{35}$, $R^{36}$ to $R^{43}$, and $R^{44}$ to $R^{51}$ each independently may be a group represented by any of general formulas 5 to 8.

The number of substituent to be bonded to the groups represented by general formulas 5 to 8 is not particularly limited. When two or more substituent are bonded to each of groups represented by general formulas 5 to 8, the substituents may be the same or different. In the present invention, an aspect in which $R^{18}$ to $R^{27}$, $R^{28}$ to $R^{35}$, $R^{36}$ to $R^{43}$, or $R^{44}$ to $R^{51}$ in general formulas 5 to 8 are all hydrogen atoms, that is, have no substituent bonded thereto is also preferred.

In general formulas 5 to 8, $R^{18}$ and $R^{19}$, $R^{19}$ and $R^{20}$, $R^{20}$ and $R^{21}$, $R^{21}$ and $R^{22}$, $R^{23}$ and $R^{24}$, $R^{24}$ and $R^{25}$, $R^{25}$ and $R^{26}$, $R^{26}$ and $R^{27}$, $R^{28}$ and $R^{29}$, $R^{29}$ and $R^{30}$, $R^{30}$ and $R^{31}$, $R^{32}$ and $R^{33}$, $R^{33}$ and $R^{34}$, $R^{34}$ and $R^{35}$, $R^{36}$ and $R^{37}$, $R^{37}$ and $R^{38}$, $R^{38}$ and $R^{39}$, $R^{40}$ and $R^{41}$, $R^{41}$ and $R^{42}$, $R^{42}$ and $R^{43}$, $R^{44}$ and $R^{45}$, $R^{45}$ and $R^{46}$, $R^{46}$ and $R^{47}$, $R^{48}$ and $R^{49}$, $R^{49}$ and $R^{50}$, and $R^{50}$ and $R^{51}$ may be bonded to each other to form a cyclic structure.

A cyclic structure formed by bonding of the two substituents described above may be an aromatic ring or aliphatic ring, or may be a ring containing a hetero atom. Alternatively, the cyclic structure may be a fused ring of two or more rings. The hetero atom referred to herein is preferably an atom selected from the group consisting of a nitrogen atom, oxygen atom, and sulfur atom. Examples of the cyclic structure to be formed include a benzene ring, naphthalene ring, pyridine ring, pyridazine ring, pyrimidine ring, pyradine ring, pyrrole ring, imidazole ring, pyrazole ring, triazole ring, imidazoline ring, oxazole ring, isooxazole ring, thiazole ring, isothiazole ring, cyclohexadiene ring, cyclohexene ring, cyclopentaene ring, cycloheptatriene ring, cycloheptadiene ring, cycloheptaene ring, and the like.

The π-conjugated compound having a structure represented by the general formulas 1 to 3 herein can be suitably used in organic EL element materials containing the π-conjugated compound, light-emitting thin films containing the π-conjugated compound, and organic EL element containing the π-conjugated compound.

When the π-conjugated compound having a structure represented by the general formulas 1 to 3 is used in an organic EL element, the element can be used as a material for light-emitting layers. The light-emitting layer of the organic EL element is preferably any of a layer in which the π-conjugated compound is singly used; a layer containing the π-conjugated compound and a host compound described above; a layer containing the π-conjugated compound and a luminescent compound described below (at least one of a fluorescence-emitting compound and a phosphorescence-emitting compound); and a layer containing the π-conjugated compound, a luminescent compound described below (at least one of a fluorescence-emitting compound and a phosphorescence-emitting compound), and a host compound described below, from the viewpoint of a high light-emitting ability. When the π-conjugated compounds represented by the general formulas 1 to 3 are used as the luminescent compound, these compounds emit blue light, green light, red light, and near-infrared light.

In the π-conjugated compound having a structure represented by general formulas 1 to 3, the absolute value of the difference between the lowest singlet excited level and the lowest triplet excited level of the π-conjugated compound ($\Delta E_{ST}$) is preferably 0.50 eV or less, from the viewpoint of development of the TADF property. An organic EL element containing such a π-conjugated compound in its light-emitting layer may be suitably included in a lighting apparatus and display apparatus.

Exemplary compounds of the π-conjugated compound represented by general formulas 1 to 3 are listed below, but the present invention is not limited thereto.

[Formula 13]

D-1

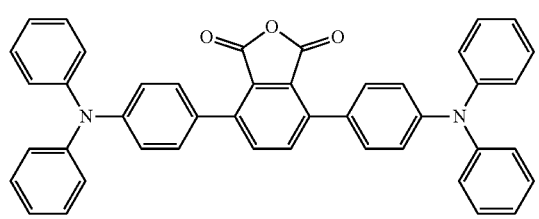

D-2

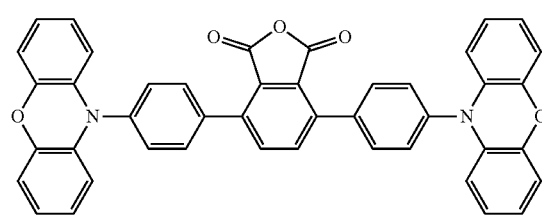

-continued
D-3
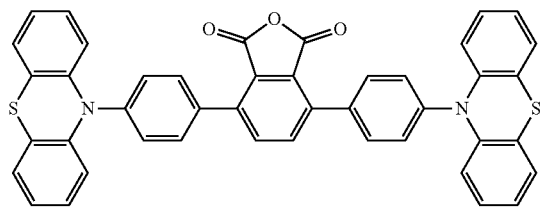
D-4
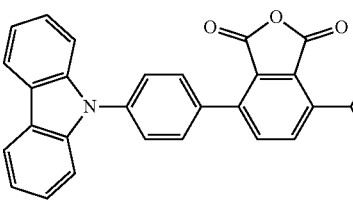
D-5
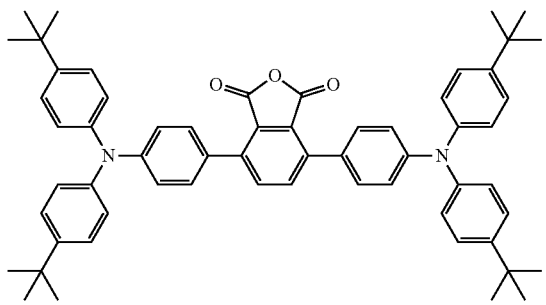
D-6
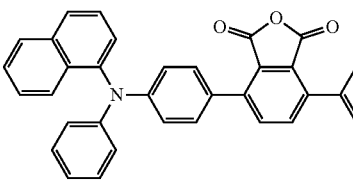
D-7
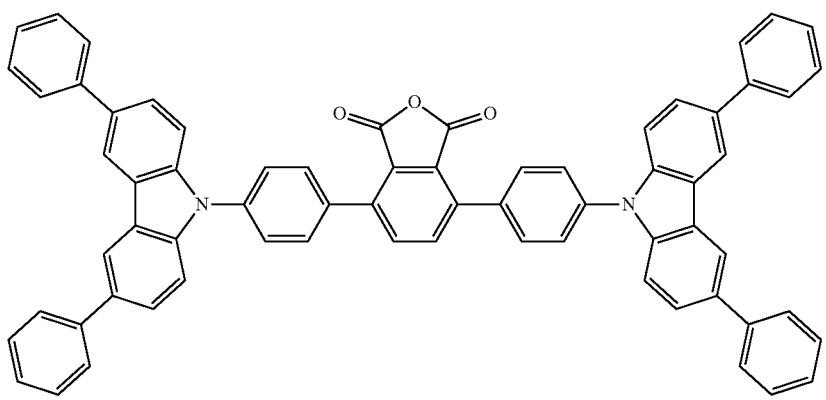
D-8
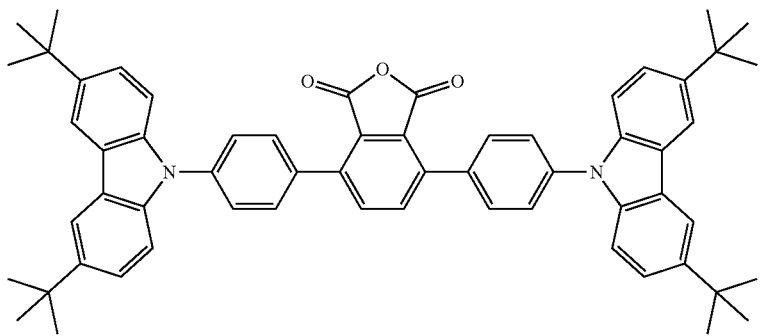
D-9
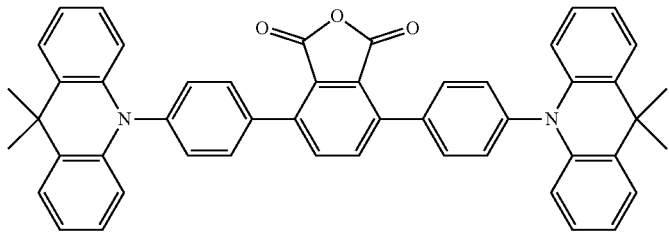

D-10
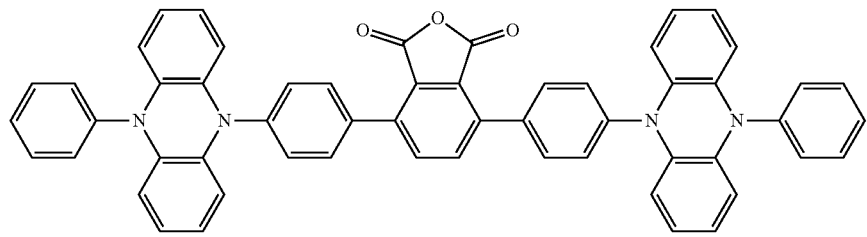
D-11
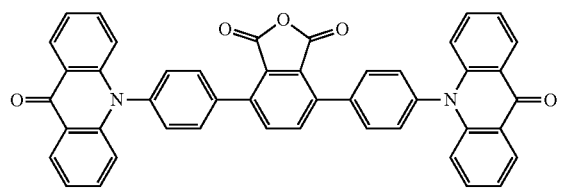
D-12
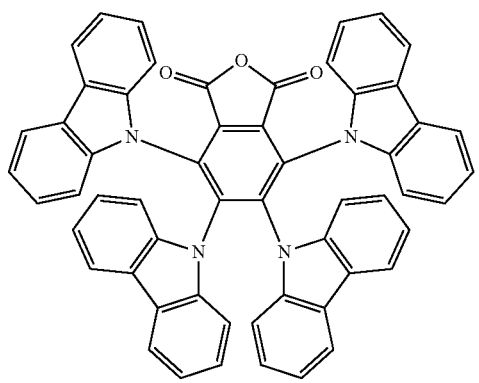
D-13
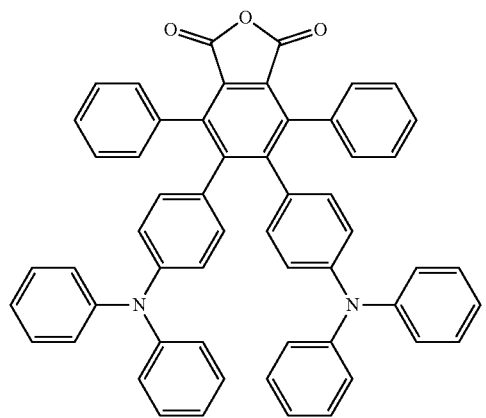
[Formula 14]
D-14
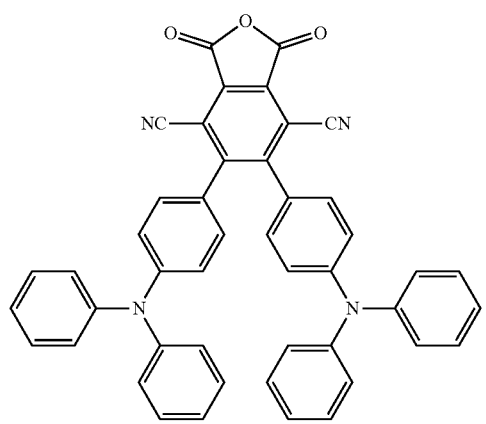
D-15
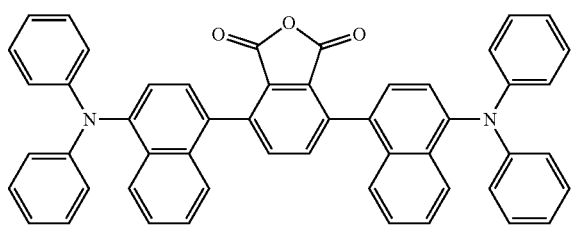

-continued
D-16
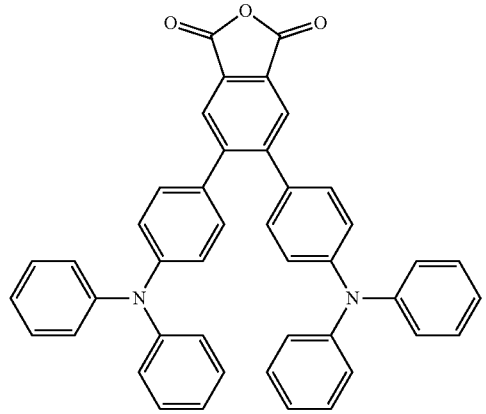
D-17
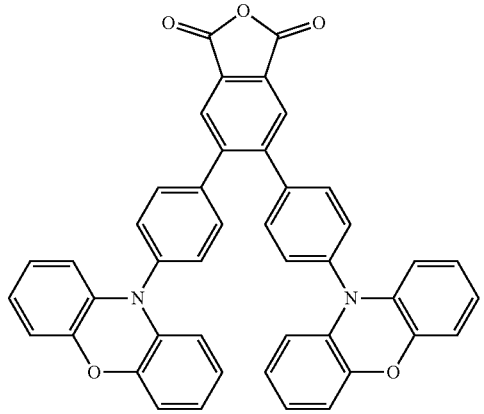
D-18
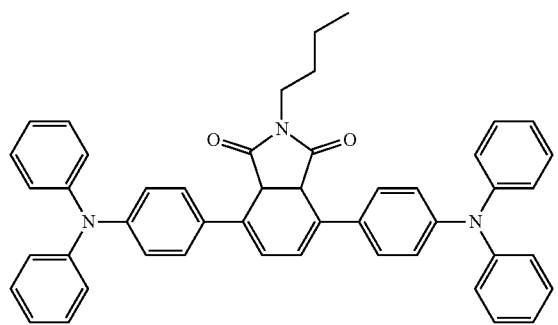
D-19
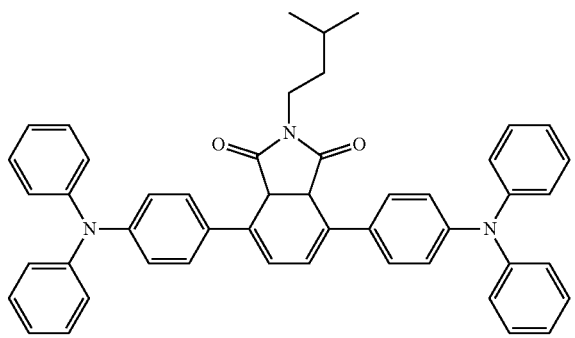
D-20
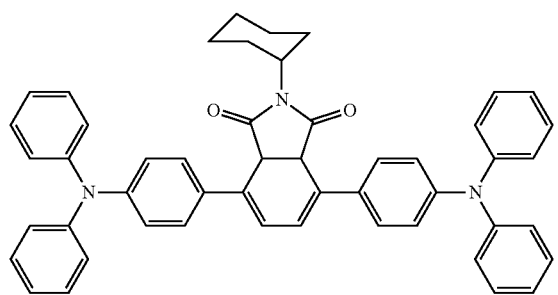
D-21
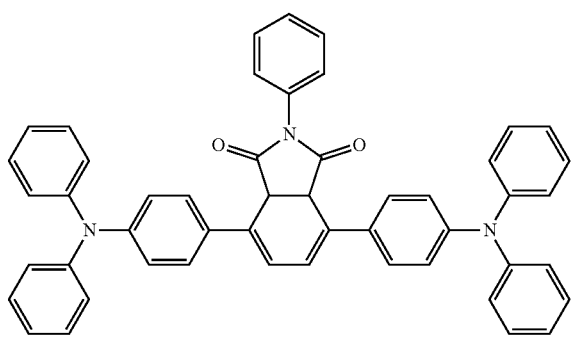
D-22
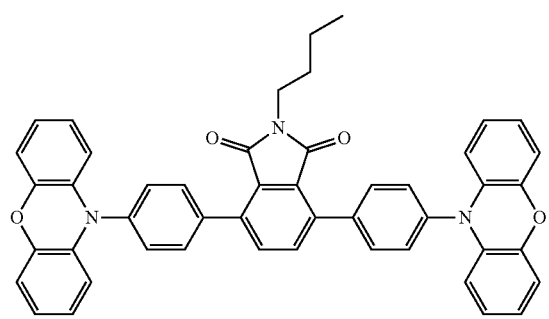
D-23
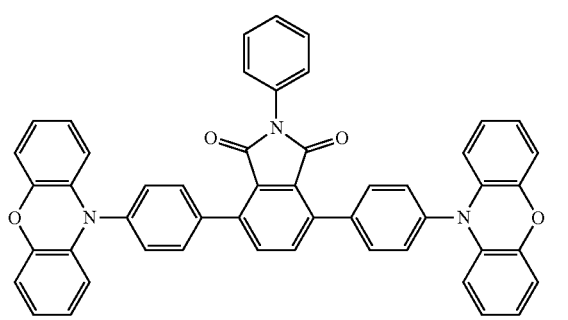

-continued
D-24
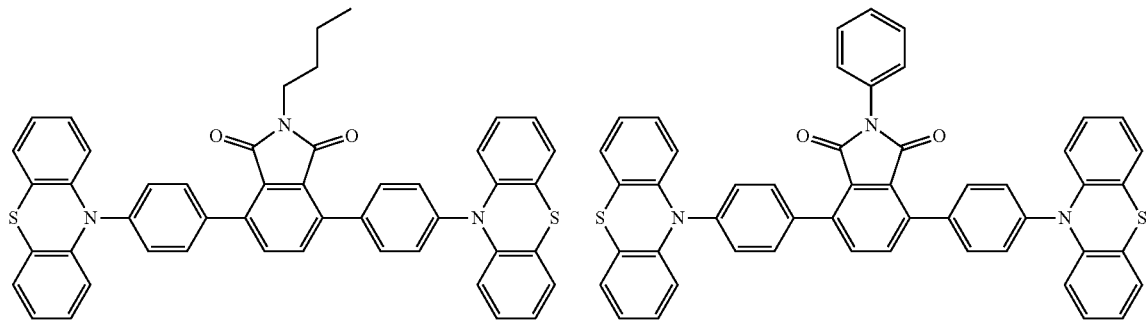
D-25
D-26
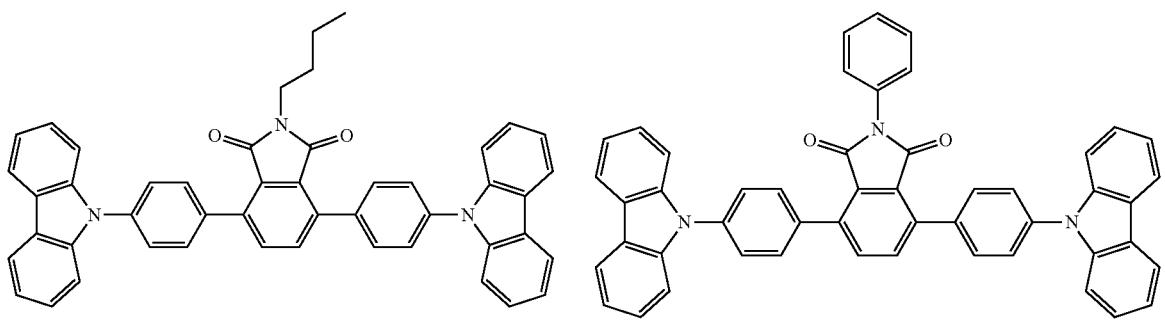
D-27
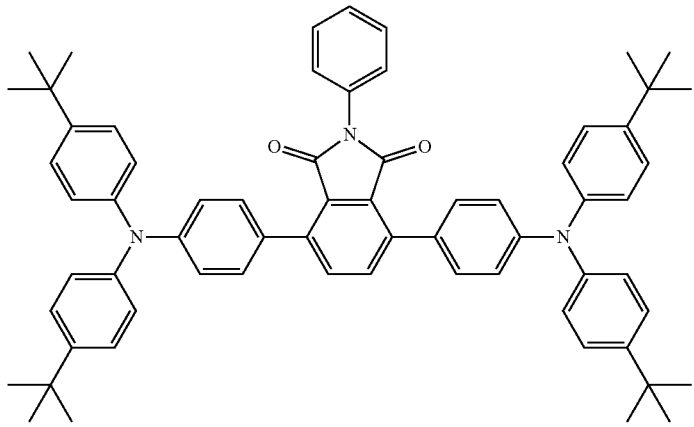
D-28
[Formula 15]
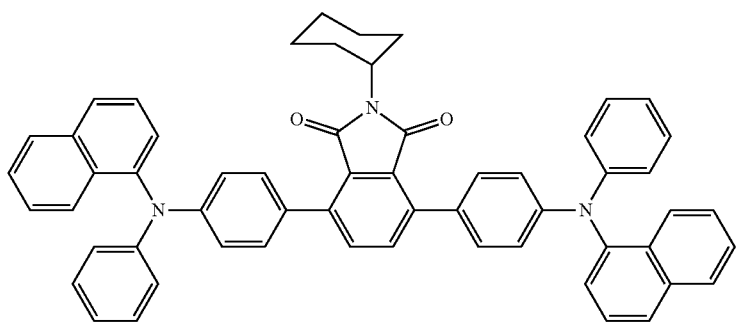
D-29

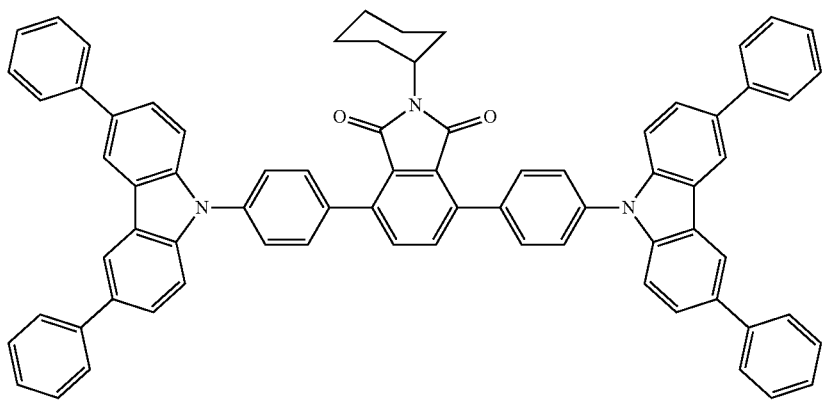
D-30
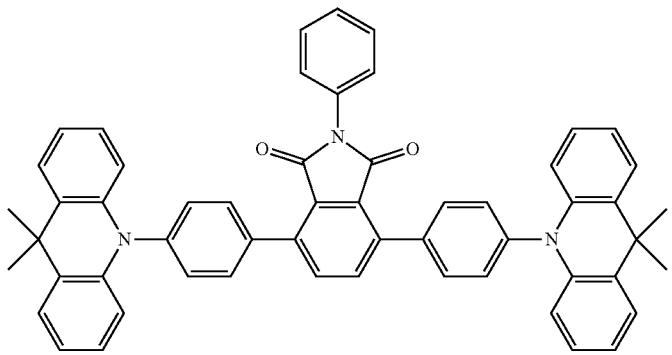
D-31
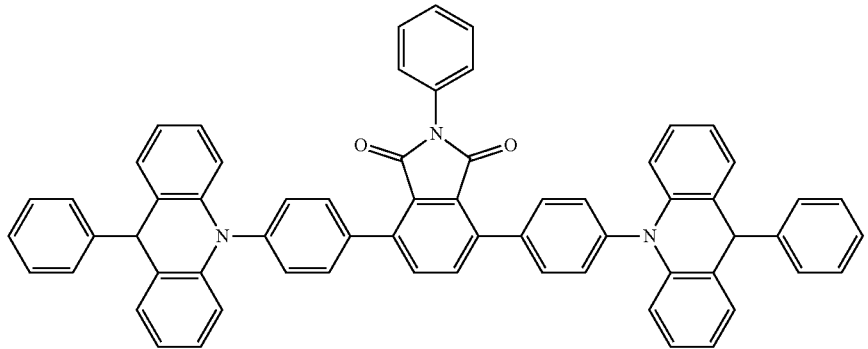
D-32
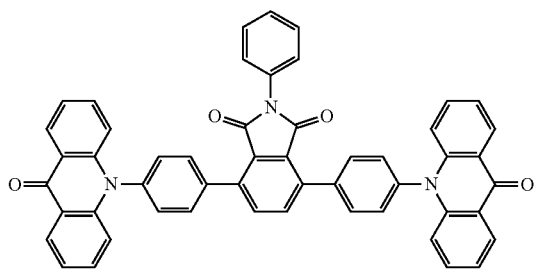
D-33
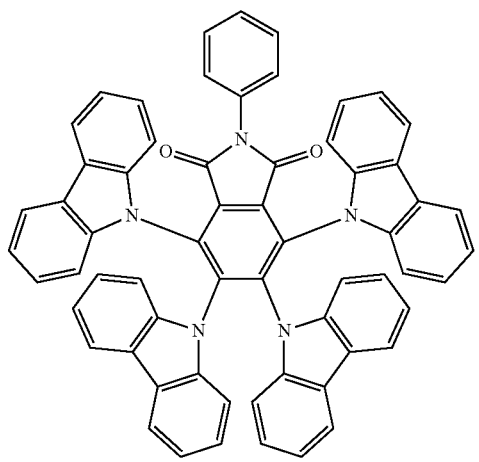
D-34

-continued
D-35
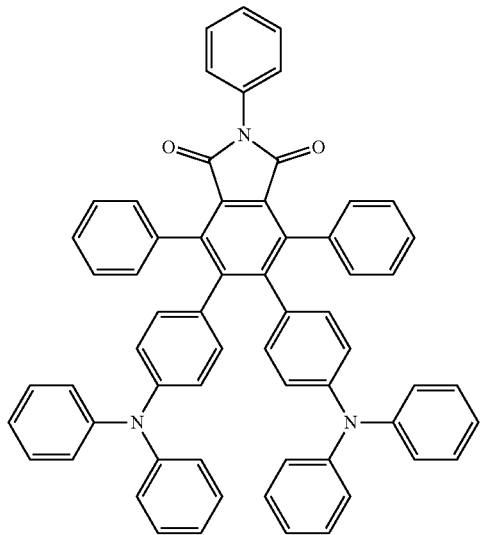
D-36
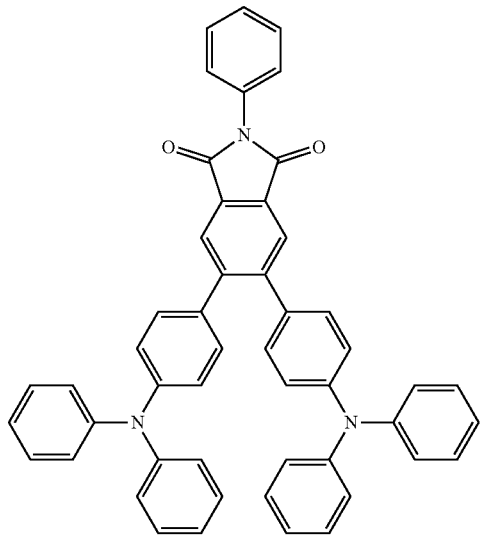
D-37
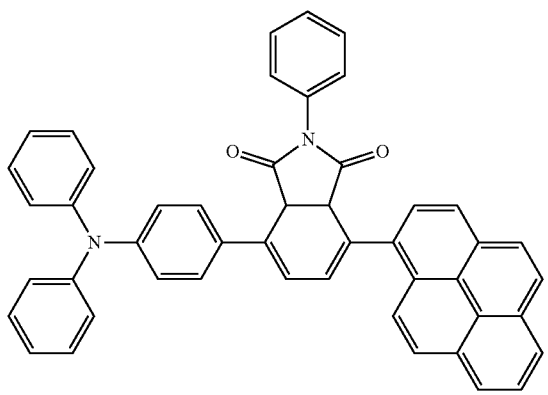
D-38
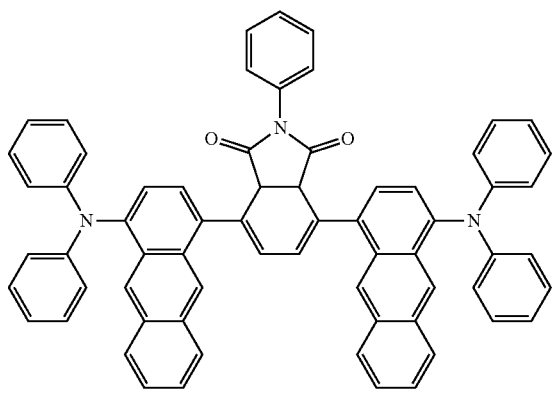
D-39
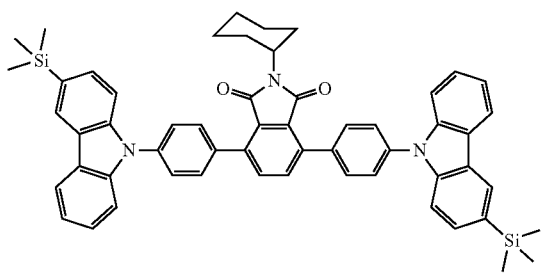
D-40
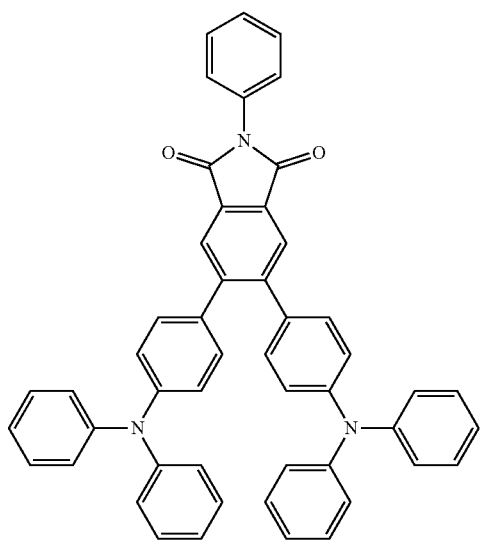

D-41
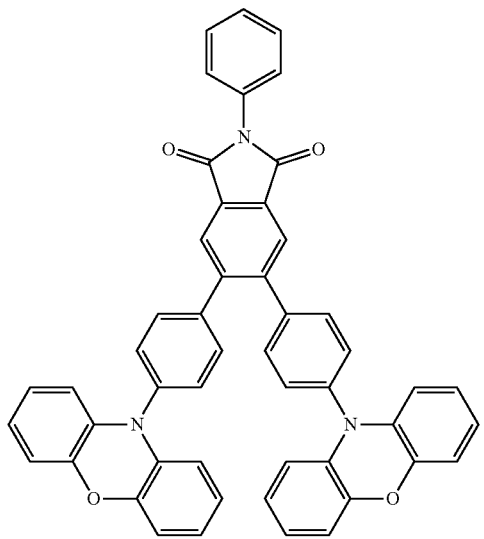
[Formula 16]
D-42
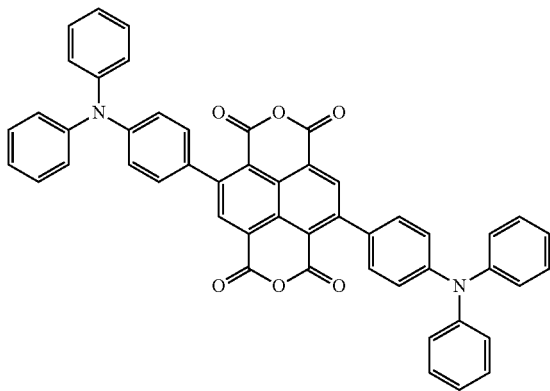
D-43
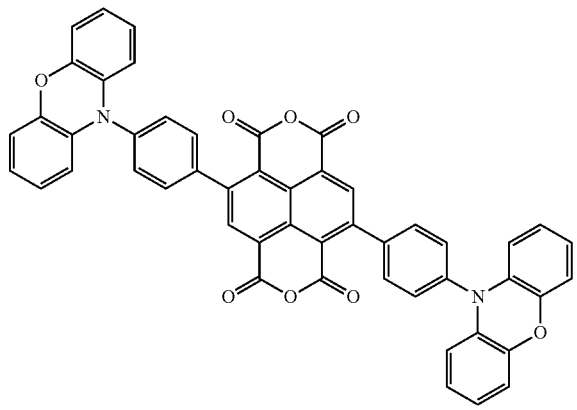
D-44
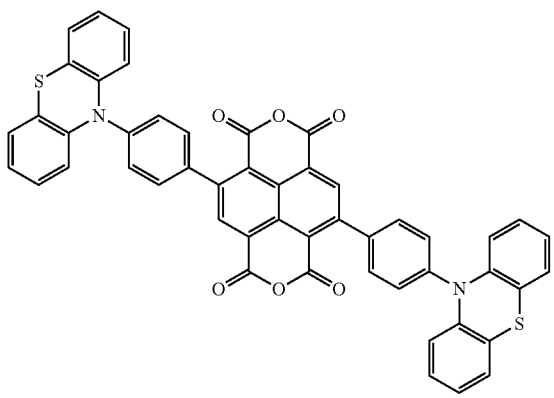
D-45
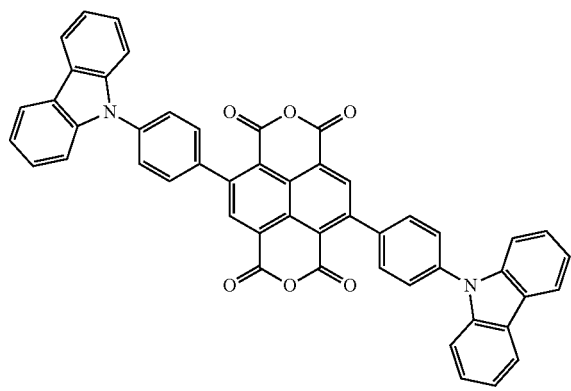

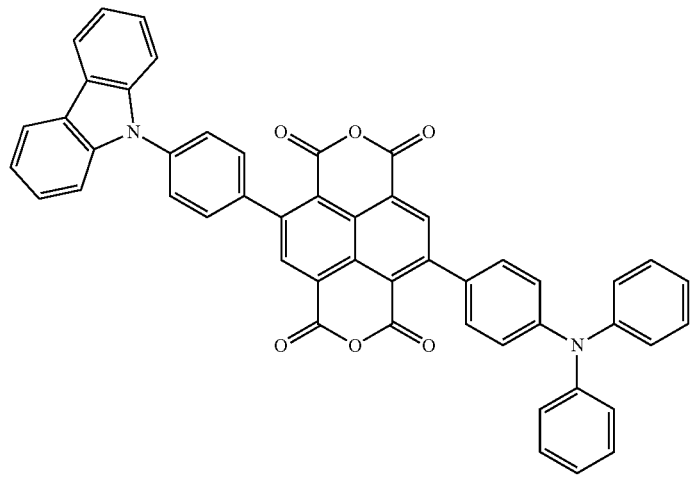
D-46
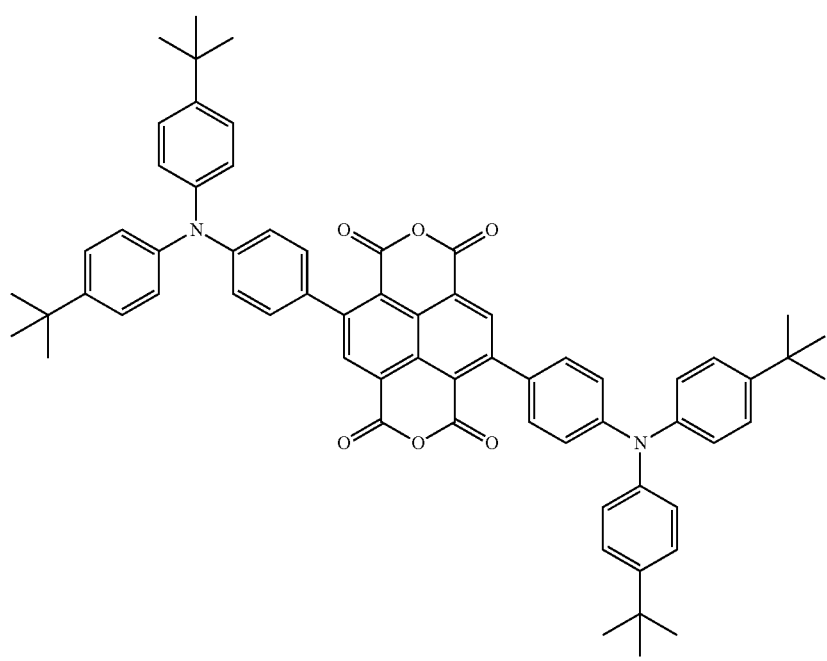
D-47

-continued
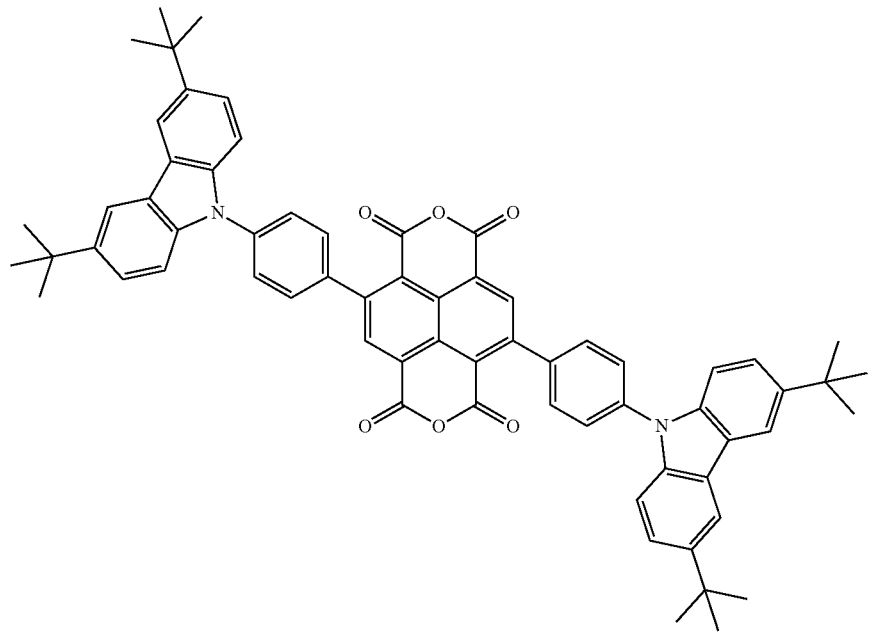
D-48
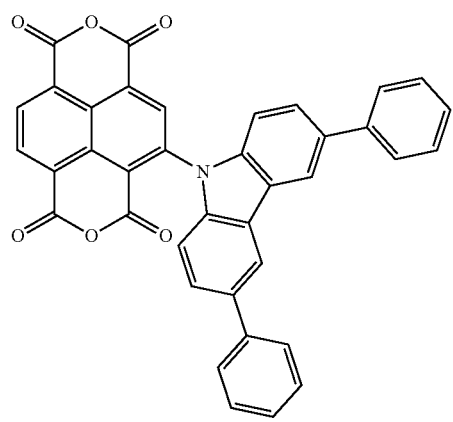
D-49
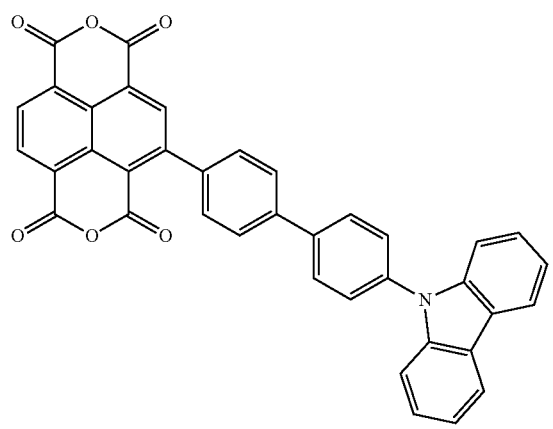
D-50
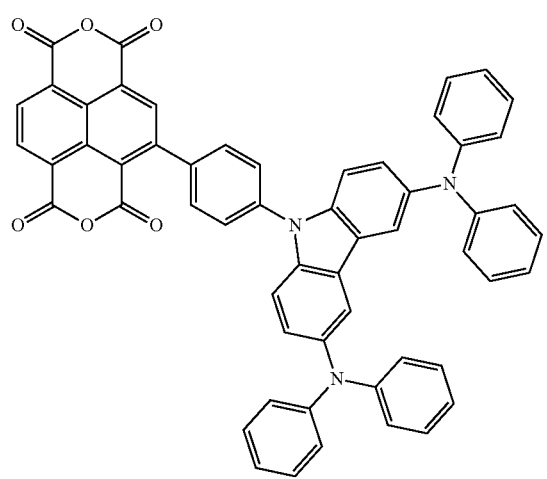
D-51

[Formula 17]
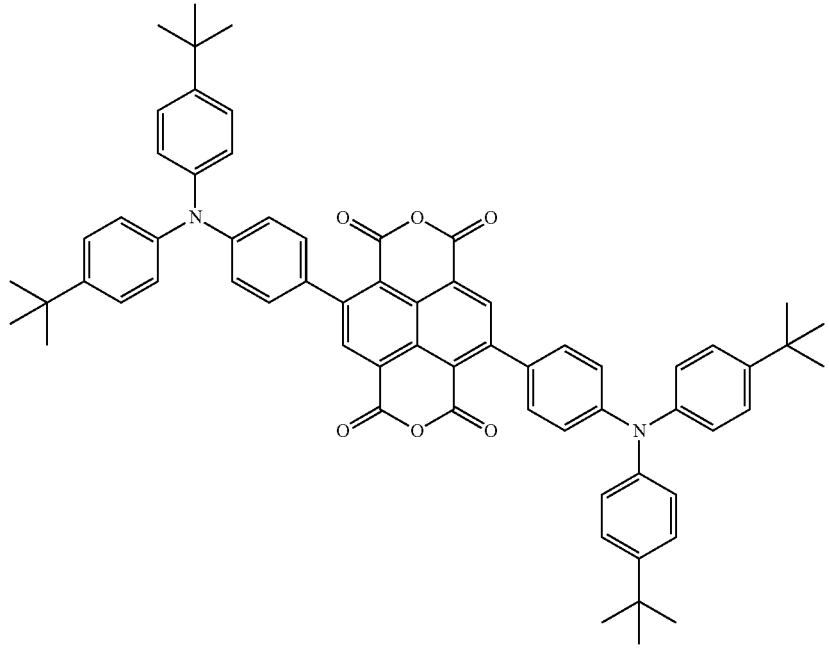
D-52
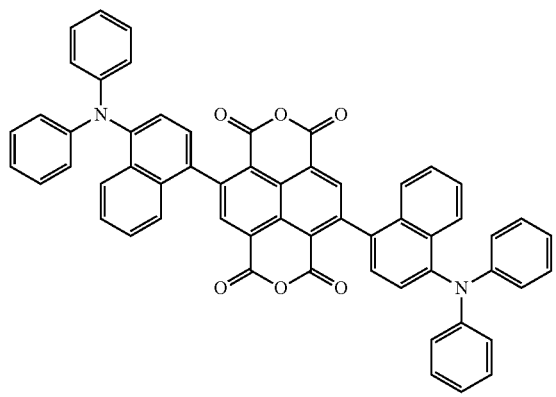
D-53
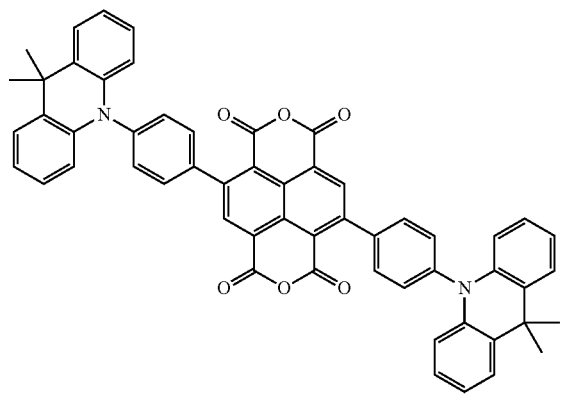
D-54
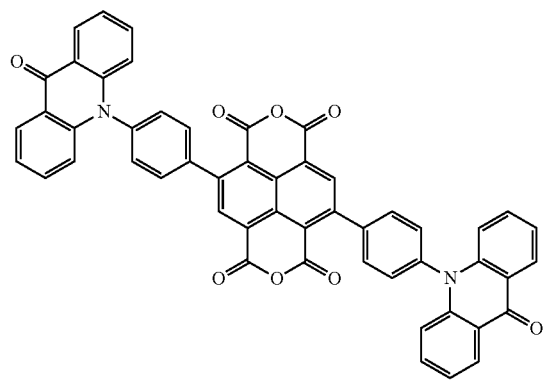
D-55
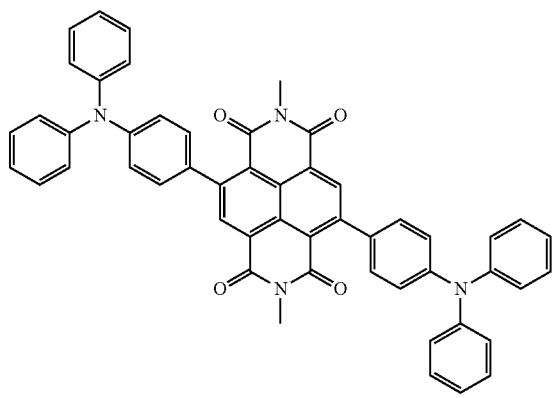
D-56

-continued
D-57
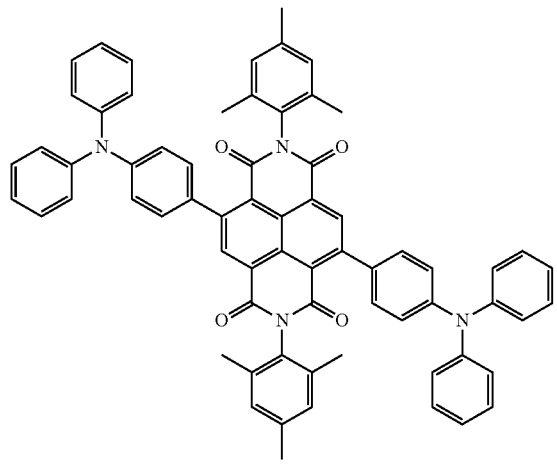
D-58
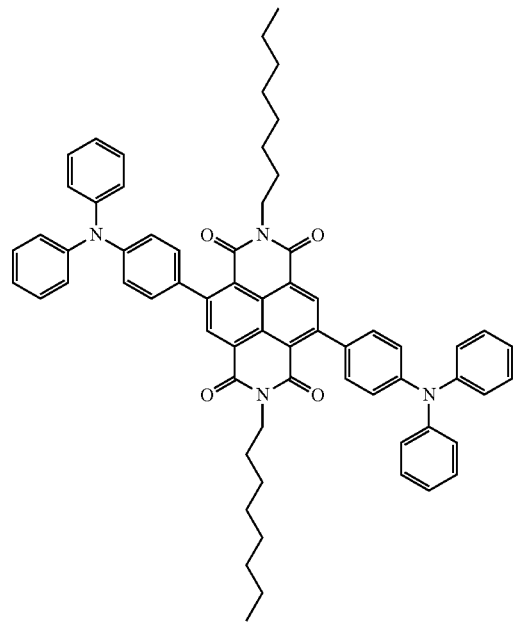
D-59
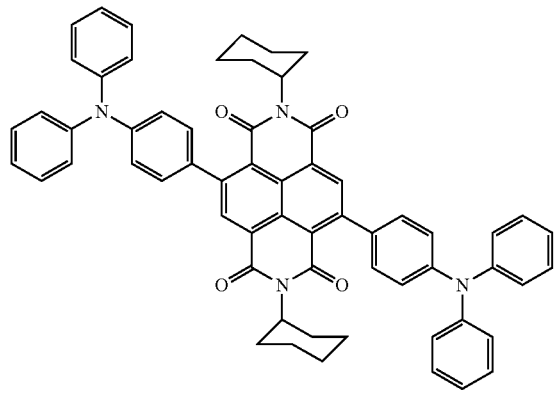
D-60
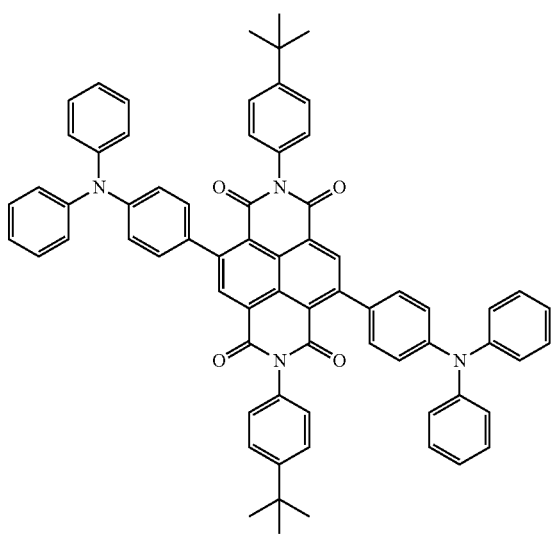

D-61
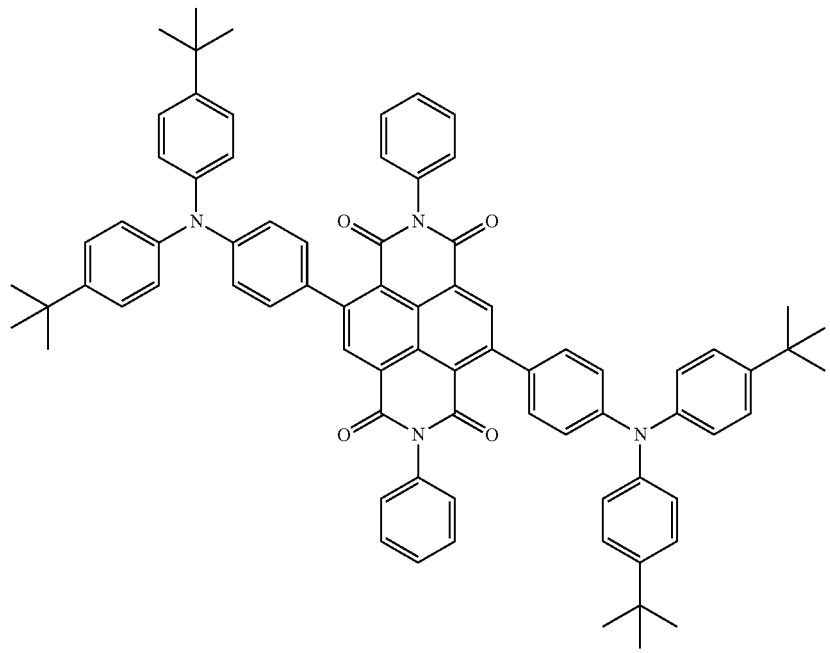
[Formula 18]
D-62
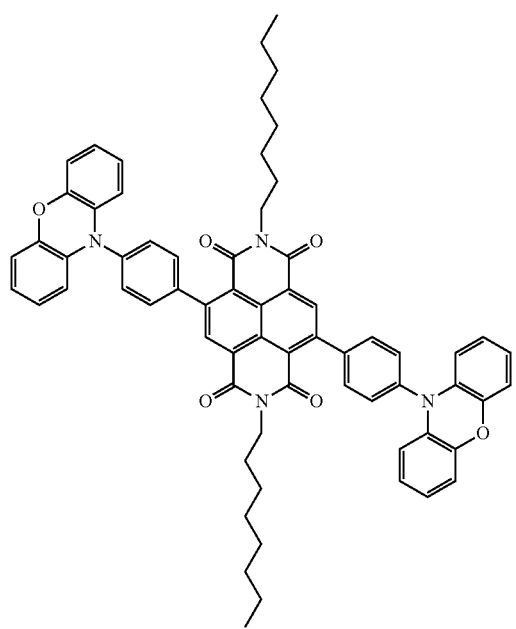
D-63
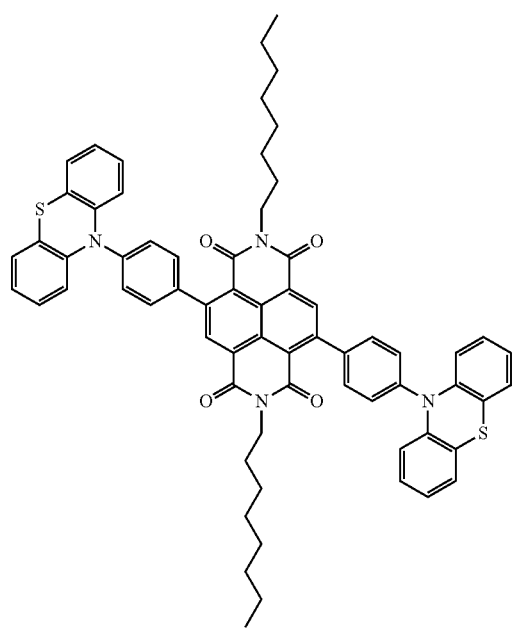

-continued
D-64
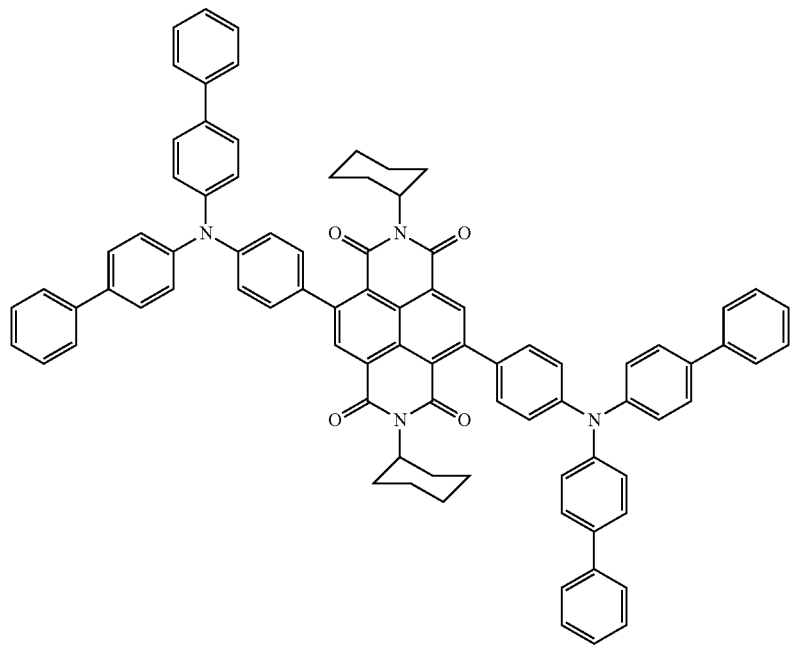
D-65 D-66
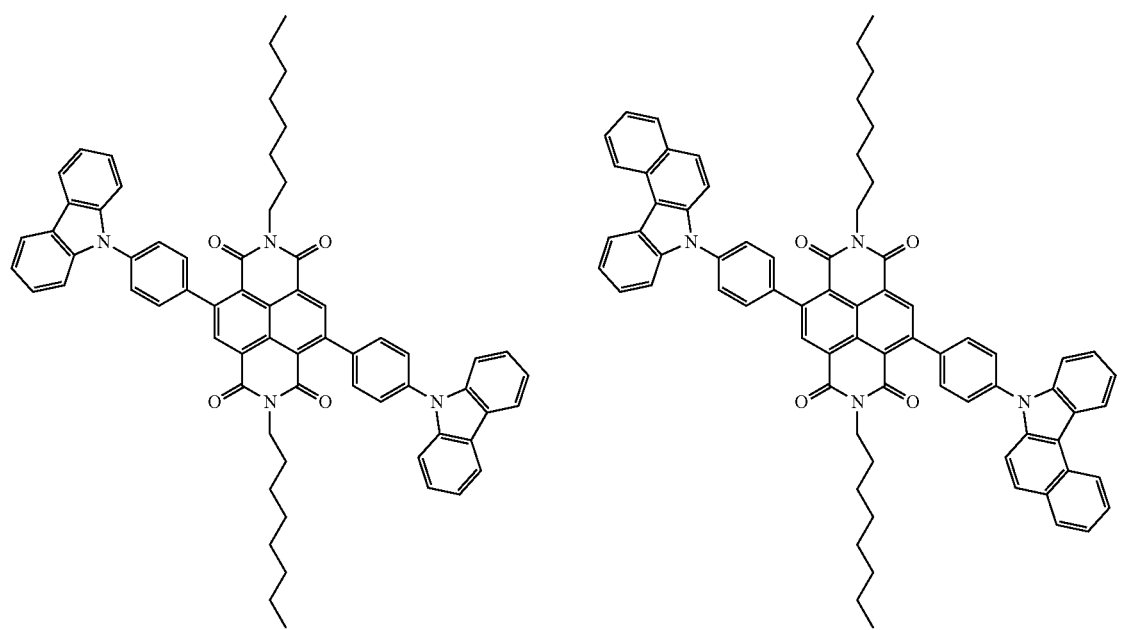

-continued
D-67
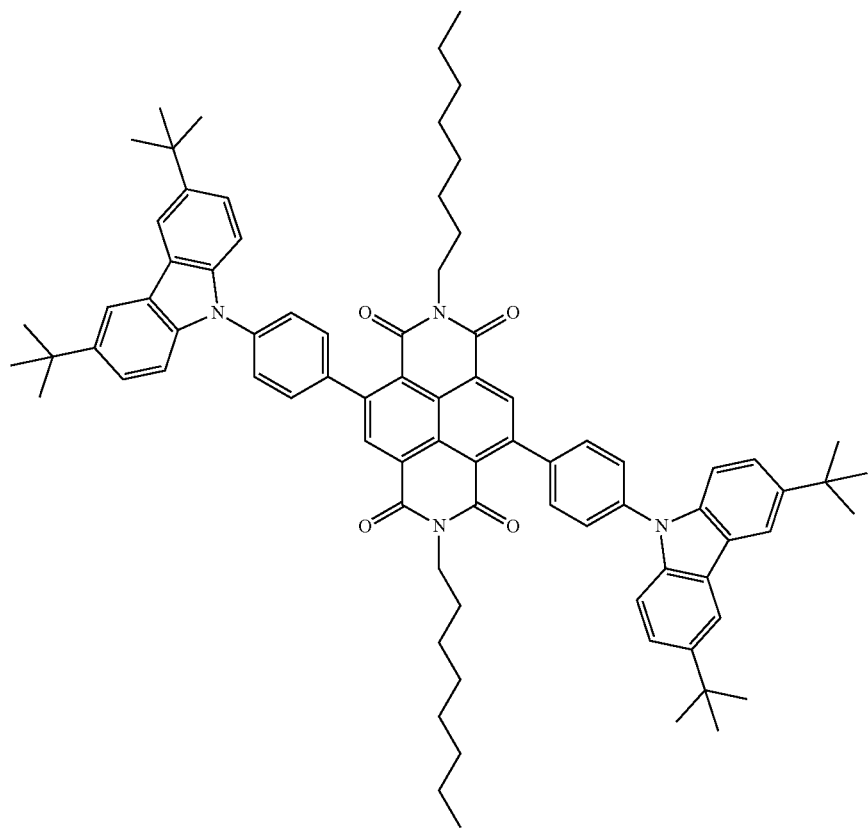
D-68
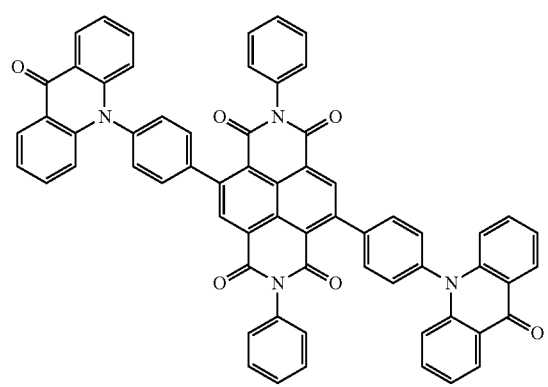
D-69

D-70
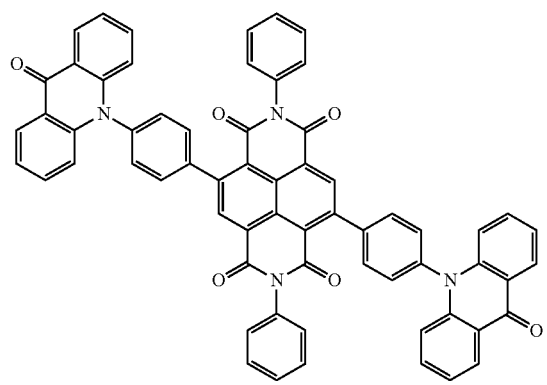
D-71
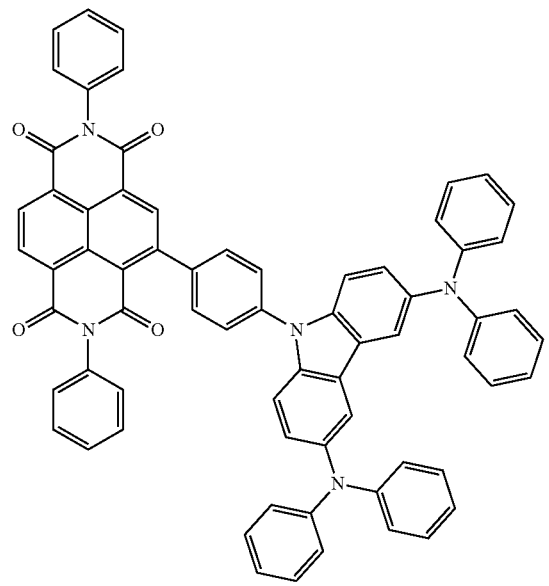
D-72
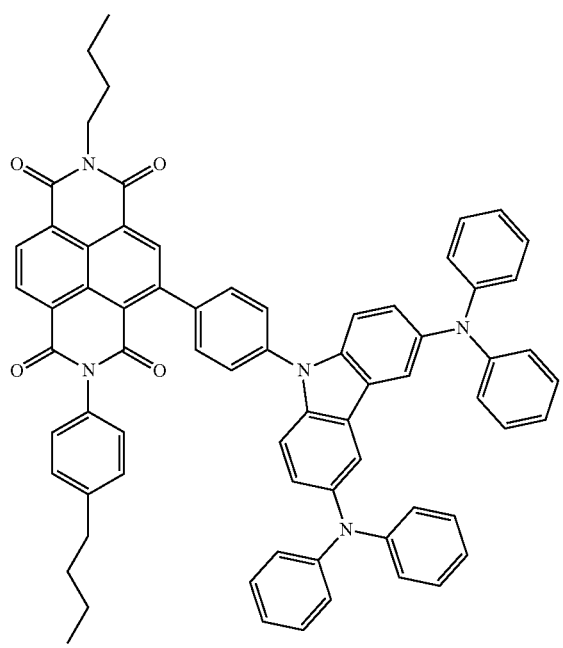

[Formula 19]
D-73
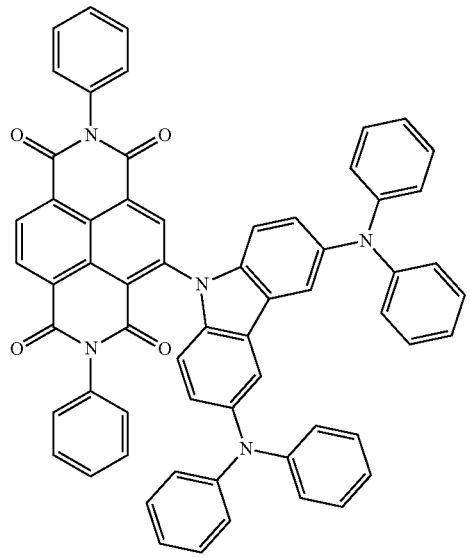
D-74
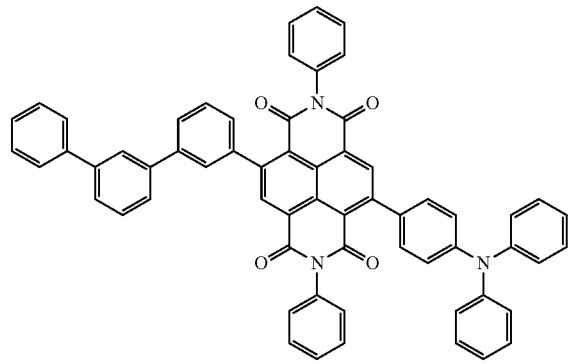
D-75
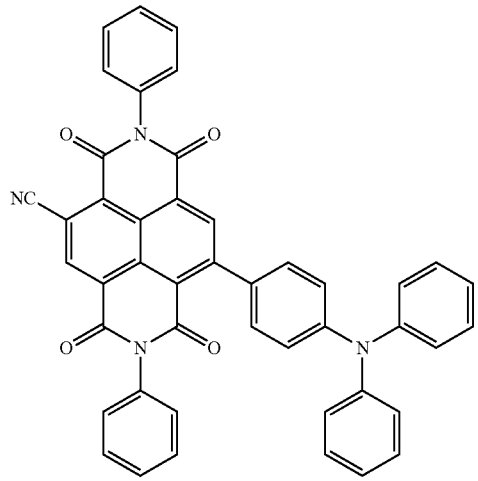
D-76
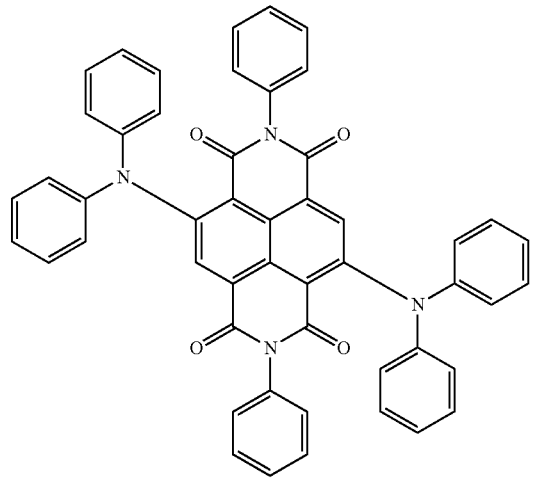
D-77
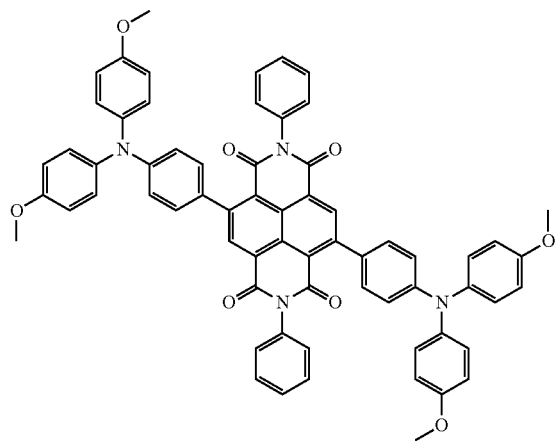
D-78
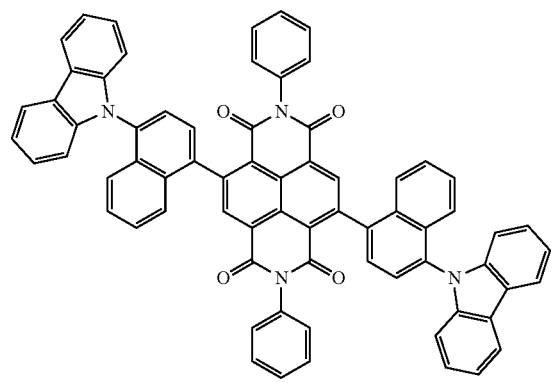

D-79
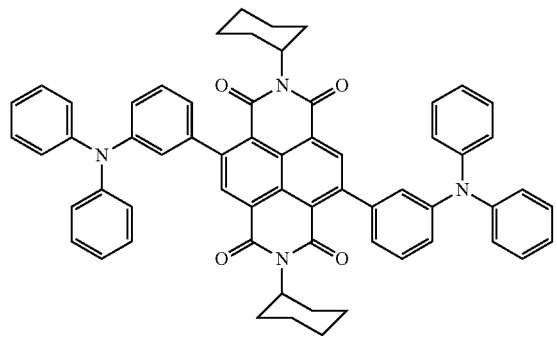
D-80
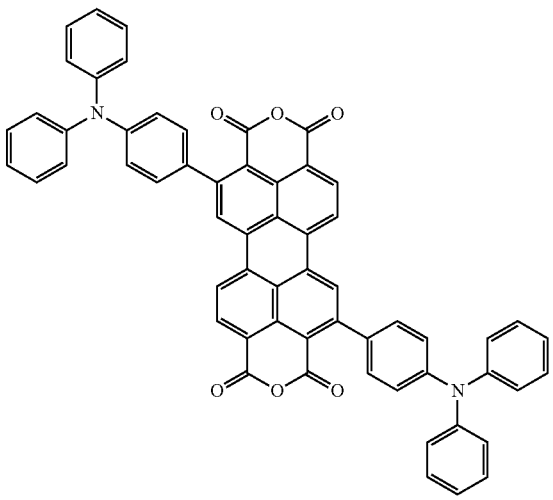
D-81
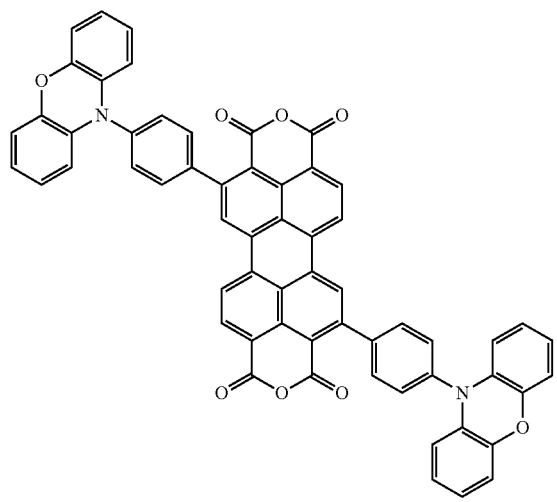
D-82
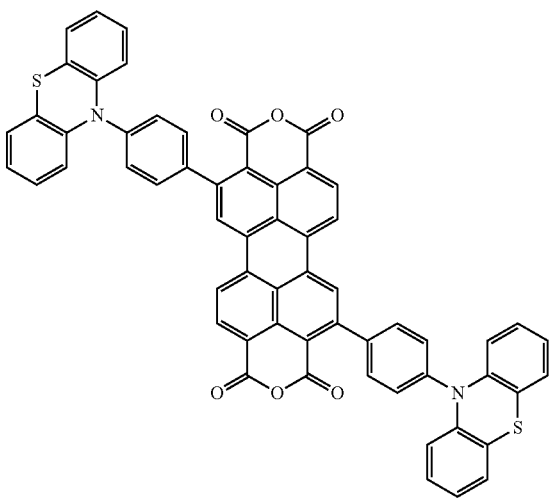
[Formula 20]
D-83
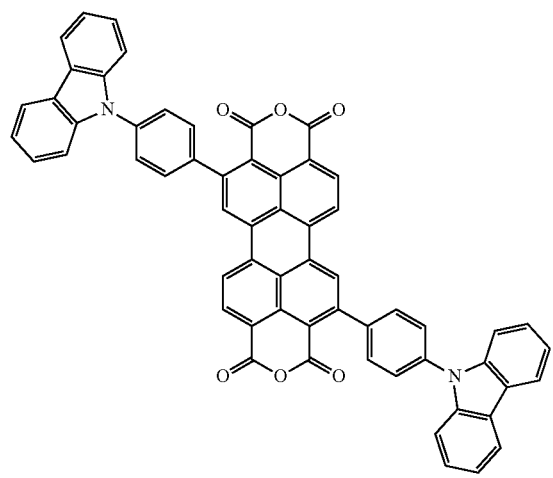
D-84
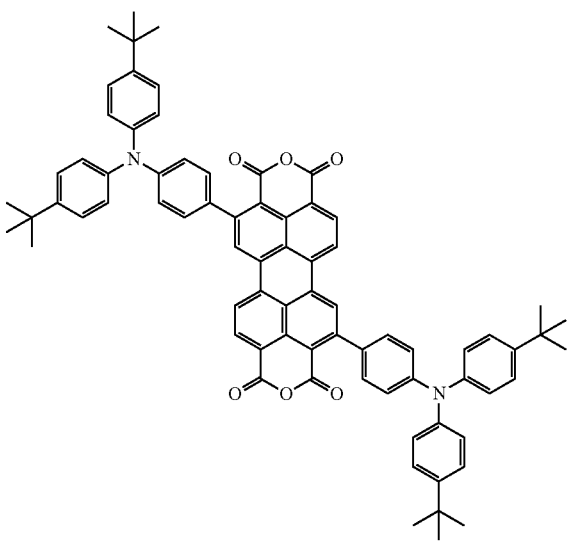

-continued
D-85
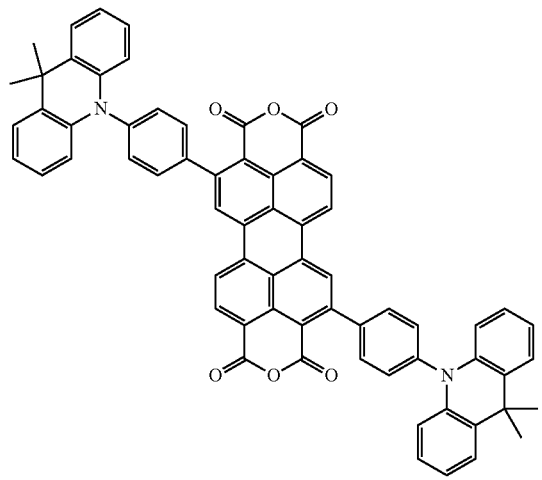
D-86
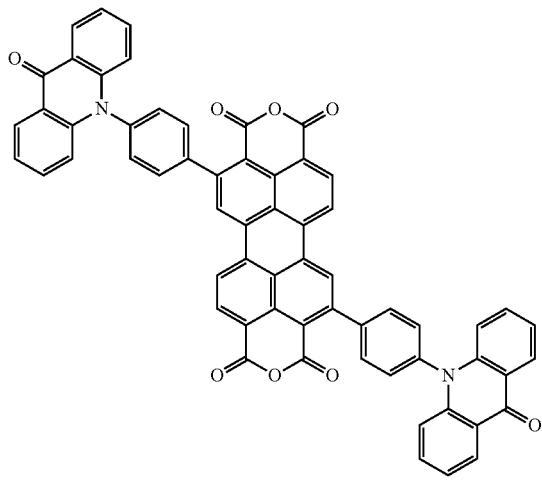
D-87
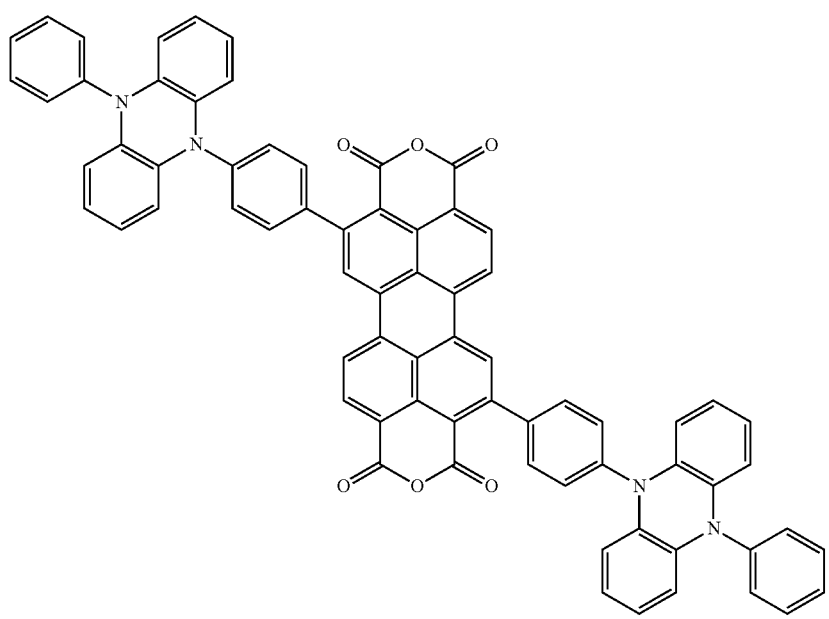

D-88
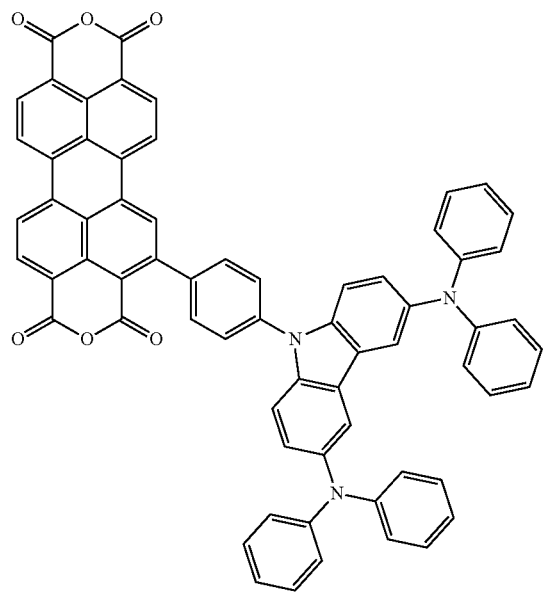
D-89
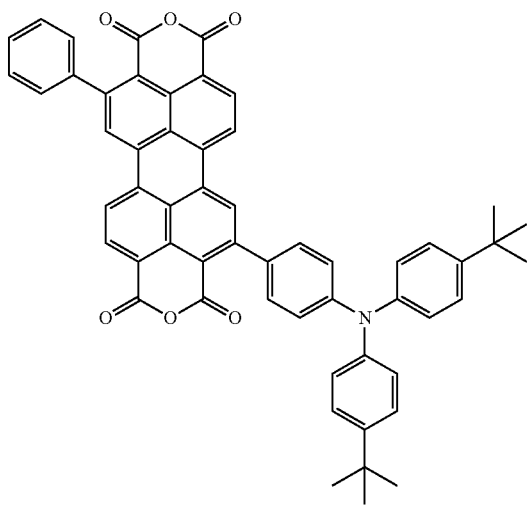
D-90
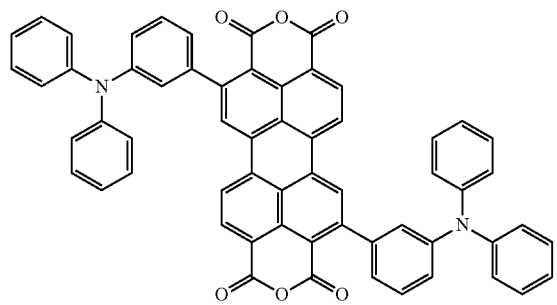
D-91
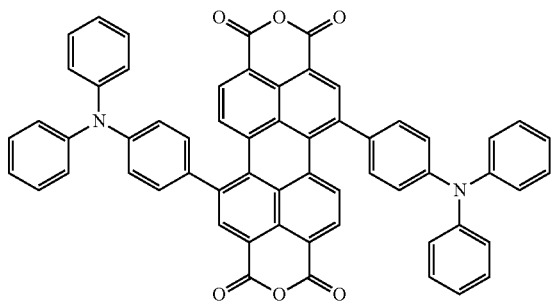
D-92
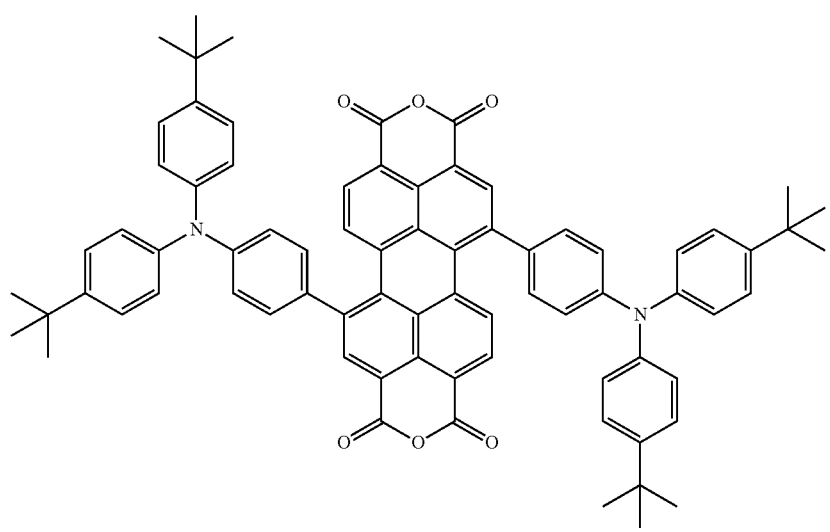

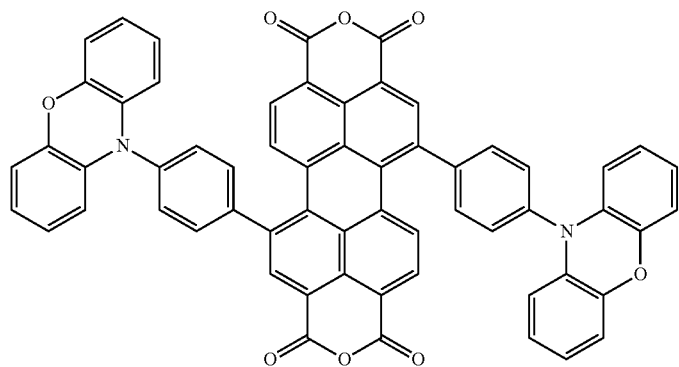
D-93
[Formula 21]
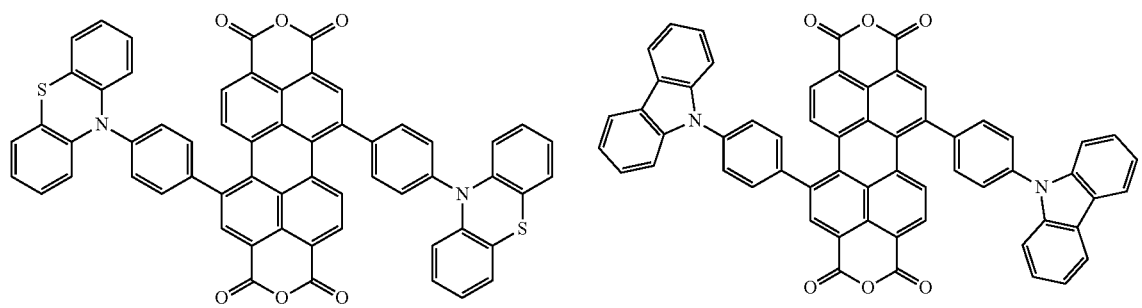
D-94  D-95
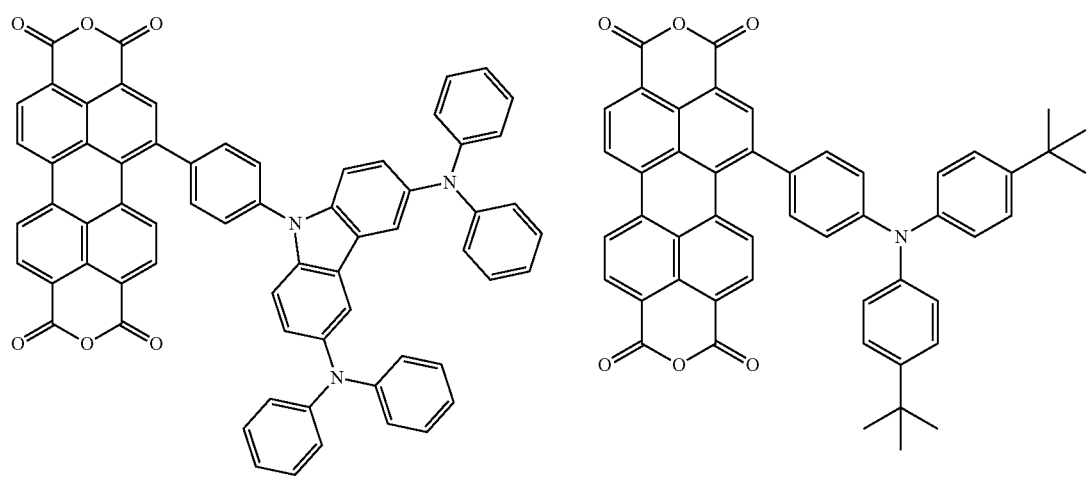
D-96  D-97

D-98
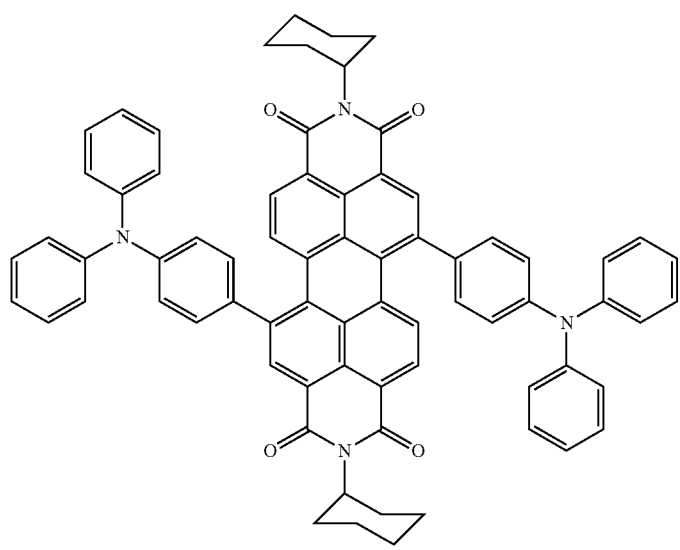
D-99
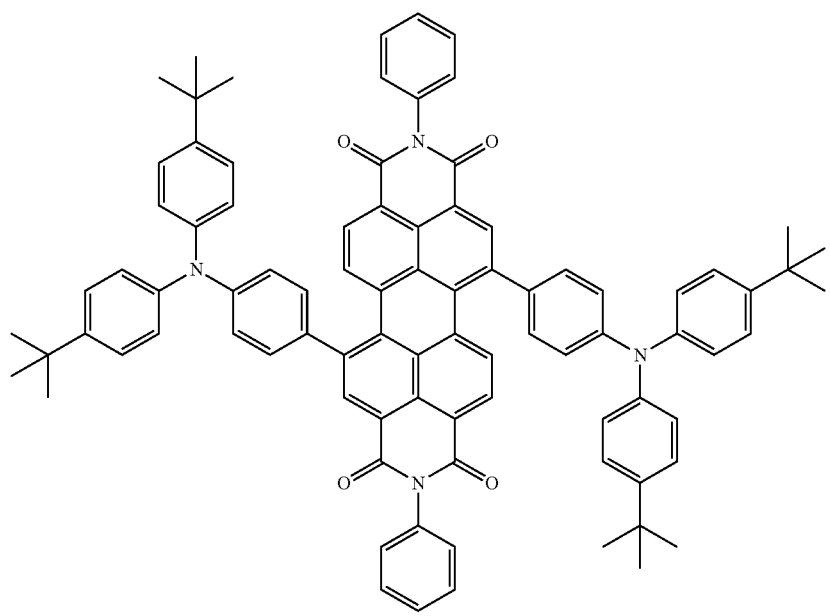

-continued
D-100
D-101
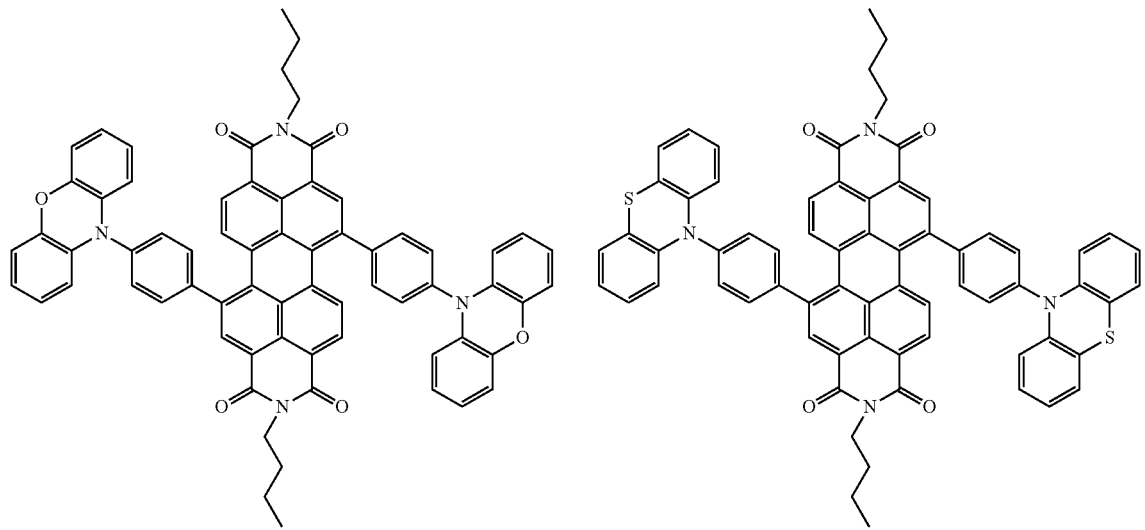
D-102
D-103
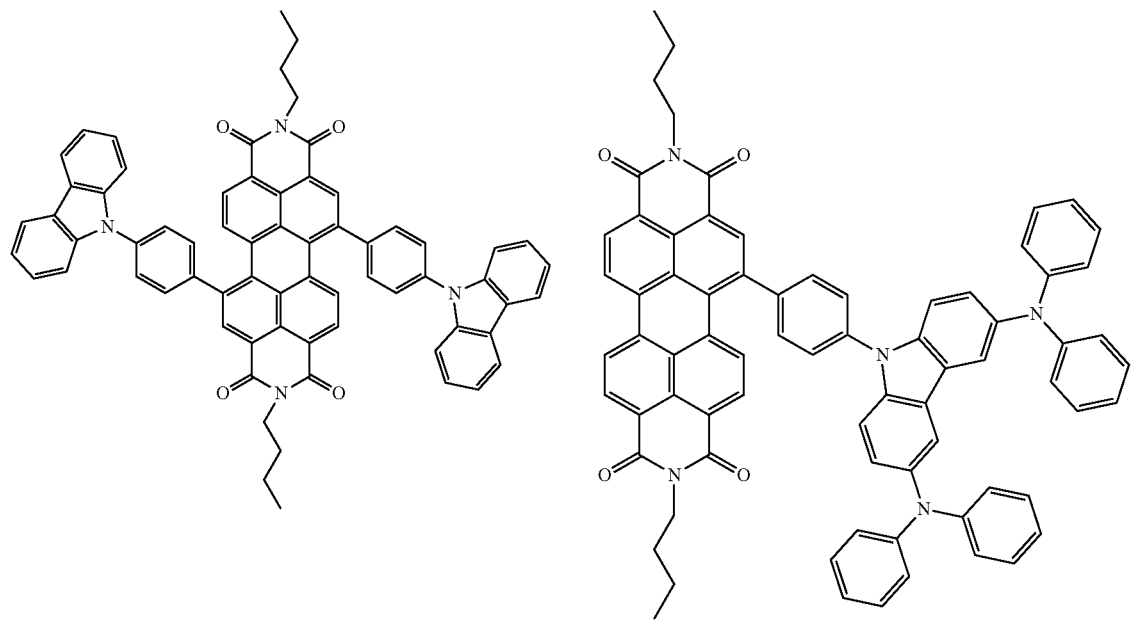

-continued
D-104
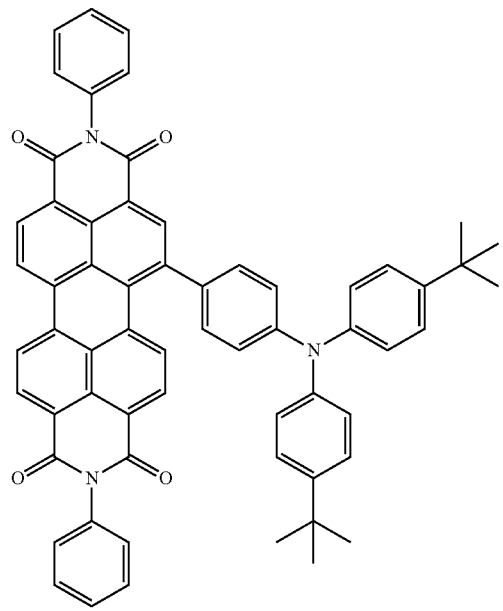
D-105
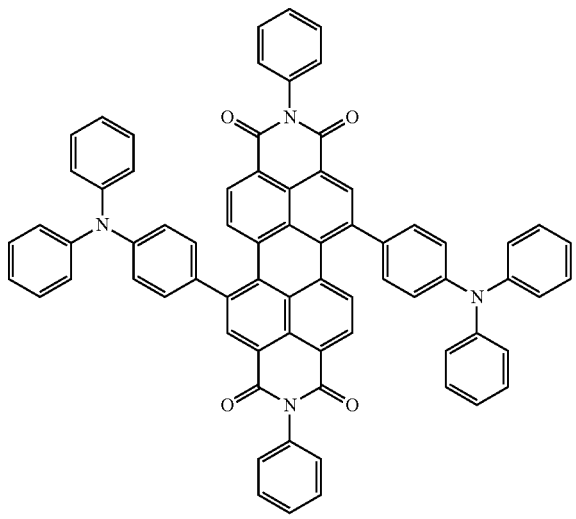
[Formula 22]
D-106
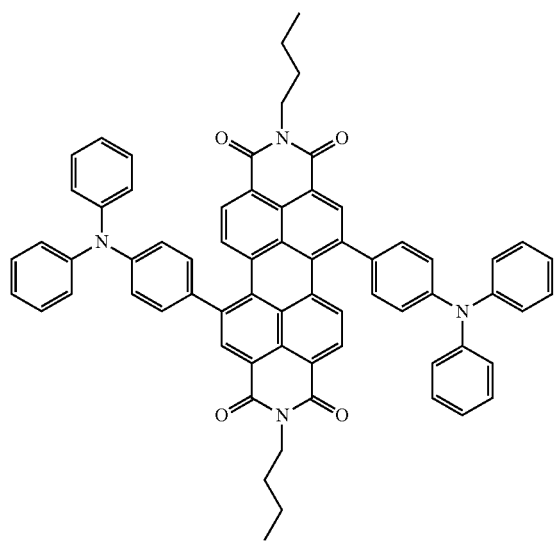
D-107
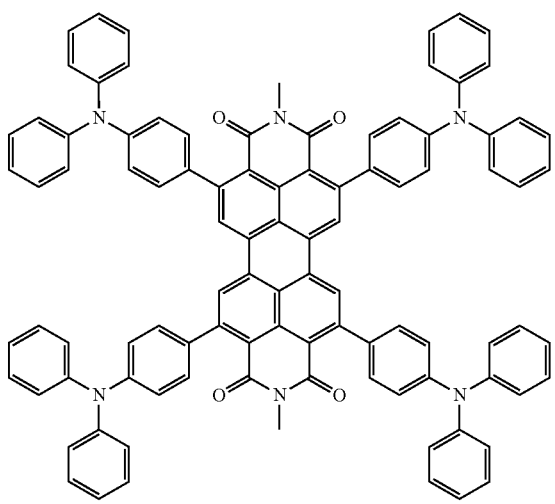

-continued
D-108
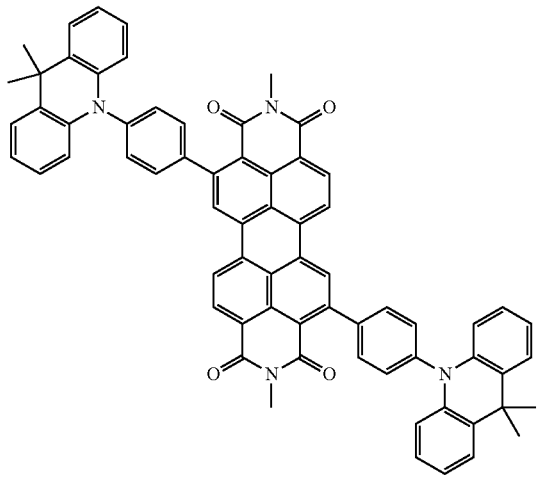
D-109
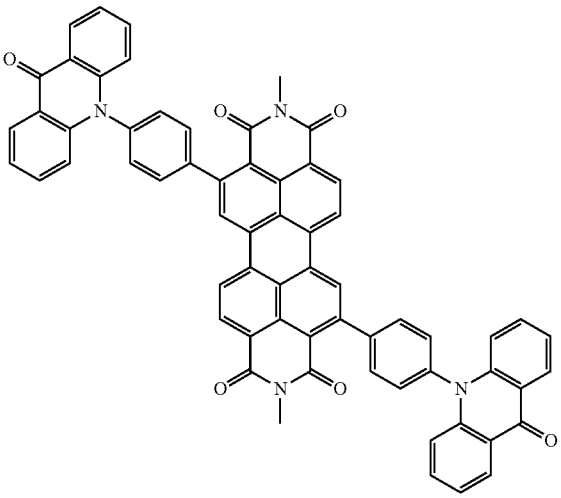
D-110
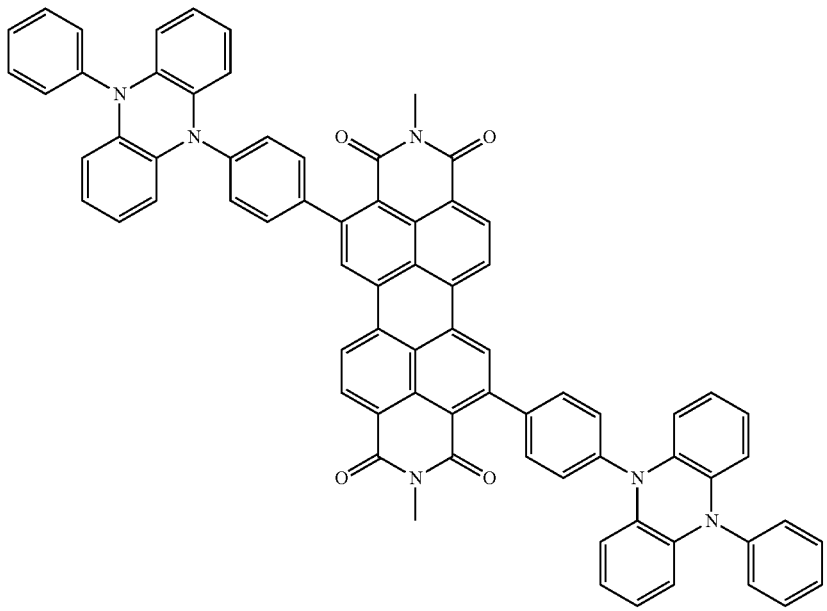
D-111
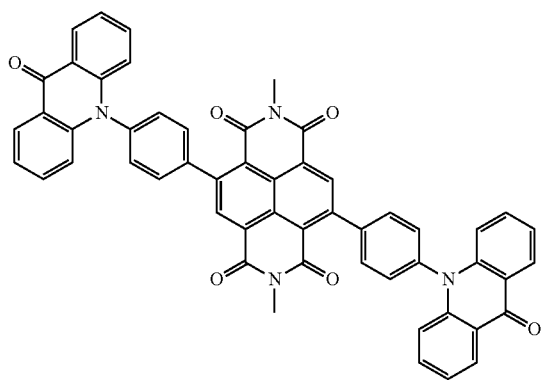
D-112
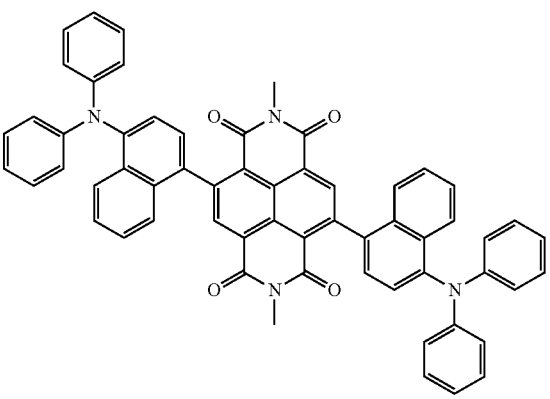

Materials having an absolute value of $\Delta E_{ST}$ of 0.50 eV or less among these compounds may exhibit the TADF property.

Furthermore, these compounds, which have a bipolar ability and can comply with various energy levels, can be used not only as a material for the light-emitting layer of organic EL elements but also used as a compound suitable for hole transport and electron transport. Accordingly, the π-conjugated compound is not limited to use in the light-emitting layer and may be used for a hole injection layer, hole transport layer, electron blocking layer, hole blocking layer, electron transport layer, electron injection layer, intermediate layer described below, or the like.

<Synthesis Method of π-Conjugated Compound Represented by General Formulas 1 to 3>

The π-conjugated compound represented by the general formulas 1 to 3 can be produced with reference to the methods described in, for example, J. Org. Chem, 2006, 71, 2107-2114., Organic Letters, 2011, 13, 3012-3015., Organic Letters, 2010, 12, 2374-2377., Dalton Transactions. 2013, 42, 9595-9605., J. Am. Chem. Soc. 2009, 131, 8-9., Angew. Chem. Int. Ed. 2005, 44, 4442-4489., and Angew. Chem. Int. Ed. 2010, 49, 2014-2017 or the methods described in reference literatures described in these literatures. The π-conjugated compound represented by general formulas 1 to 3 can be synthesized also by combining other known synthesis reactions.

Subsequently, will be described an emission mode of organic EL and luminescent compounds (phosphorescence-emitting compound, fluorescence-emitting compound, and delayed fluorescent compound), which relate to the technical concept of the present invention.

<Emission Mode of Organic EL>

Organic EL emits light based on either of the following two emission modes: "phosphorescence," which occurs during transfer of excitons from the triplet excited state to the ground state, and "fluorescence," which occurs during transfer of excitons from the singlet excited state to the ground state. In the case of electric-field excitation as in organic EL, triplet excitons are generated at a probability of 75% and singlet excitons are generated at a probability of 25%. Thus, "a phosphorescent" mode exhibits emission efficiency higher than that of the fluorescent mode, and is excellent for reducing power consumption.

Herein, also in the case of fluorescence, triplet excitons are generated at a probability of 75%. Then, the energy of the triplet excitons is usually converted into only heat due to non-radiative deactivation. In contrast, by increasing the density of such triplet excitons, one singlet exciton is generated from two triplet excitons to thereby improve the emission efficiency. A mode has been found in which this mechanism, called a triplet-triplet annihilation (TTA) (also called triplet-triplet fusion and abbreviated as TTF), is employed.

Adachi, et al. have more recently found that a reduced energy gap between the singlet excited state and the triplet excited state causes reverse intersystem crossing from the triplet excited state, which has a lower energy level, to the singlet excited state depending on the Joule heat during emission and/or the ambient temperature around a light-emitting element, resulting in a phenomenon that achieves fluorescence at substantially 100% (referred to as "thermally activated delayed fluorescence (TADF)"). They have also found a fluorescent substance that achieves this phenomenon (see NPL 1, NPL 3, NPL 4 and the like).

<Phosphorescence-Emitting Compound>

Theoretically, phosphorescence has emission efficiency three times higher that of fluorescence as described above. Unfortunately, energy deactivation from the triplet excited state to the singlet ground state (i.e., phosphorescence) is a forbidden transition. The intersystem crossing from the singlet excited state to the triplet excited state is also a forbidden transition, and thus, the rate constant of such a transition is generally small. Thus, since a transition is unlikely to occur, the lifetime of excitons is on the order of milliseconds to seconds, and intended emission is difficult to achieve.

In the case of emission of a complex containing a heavy metal, such as iridium or platinum, the rate constant of the aforementioned forbidden transition increases by three or more orders of magnitude by the heavy atom effect of the central metal, and a phosphorescent quantum efficiency of 100% may be achieved depending on the selection of a ligand.

However, in order to obtain an ideal emission, it is required to use a rare metal such as iridium or palladium, or a noble metal such as platinum. If a large amount of these metals are used, the reserves and the price of these metal will become problem.

<Fluorescence-Emitting Compound>

Unlike the phosphorescence-emitting compound, a common fluorescence-emitting compound is not necessarily a heavy metal complex, and may be an organic compound composed of a combination of common elements, such as carbon, oxygen, nitrogen, and hydrogen. In such a fluorescent compound, other non-metal elements, such as phosphorus, sulfur, or silicon can be used, and a complex of a typical metal, such as aluminum or zinc can also be employed. A wide variety of such elements may be used without substantial limitation.

Unfortunately, with a conventional fluorescent compound, in which only 25% of excitons is used for light emission as aforementioned, highly effective emission phosphorescence cannot be anticipated.

<Delayed Fluorescent Compound>

[Excited Triplet-Triplet Annihilation (TTA) Delayed Fluorescent Compound]

An emission mode utilizing delayed fluorescence has emerged for solving the problems involved in a fluorescence-emitting compound. The TTA mode, which is based on collision between triplet excitons, is described by the general formula as follows. That is, the TTA mode is advantageous in that a portion of triplet excitons, the energy of which would otherwise be converted into only heat by non-radiative deactivation, undergo reverse intersystem crossing, to generate singlet excitons that can contribute to luminescence. In an actual organic EL element, the TTA mode can achieve an external extraction quantum efficiency twice that achieved in a conventional fluorescent element.

$$T^*+T^*->S^*+S \qquad \text{General formula:}$$

wherein, T* represents a triplet exciton, S* represents a singlet exciton, and S represents a molecule in the ground state.

Unfortunately, the TTA mode fails to achieve 100% internal quantum efficiency in principle because two triplet excitons generate only one singlet exciton that contributes to luminescence, also as illustrated in the aforementioned formula.

[Thermally Activated Delayed Fluorescent (TADF) Compound]

The TADF mode, which is another highly efficient fluorescent mode, can solve problems involved in the TTA mode.

The fluorescence-emitting compound is advantageous in that the compound can be molecularly designed without limitation, as described above. In other words, of molecularly designed compounds, some compounds exhibit an extremely small difference between the energy level of a triplet excited state and the energy level of a singlet excited state.

Such a compound, although having no heavy atom in the molecule, undergoes reverse intersystem crossing from the triplet excited state to the singlet excited state, which cannot normally occur, because of small $\Delta E_{ST}$. Furthermore, since the rate constant of deactivation from the singlet excited state to the ground state (i.e., fluorescence) is extremely large, the transfer of triplet excitons to the ground state via the singlet excited state with emission of fluorescence is kinetically more advantageous than the transfer of the triplet excitons to the ground state with thermal deactivation (non-radiative deactivation). Thus, in the TADF mode, 100% fluorescence can be theoretically achieved.

<Molecular Designing Idea Concerning $\Delta E_{ST}$>

A molecular designing idea to reduce the $\Delta E_{ST}$ will be described.

In order to reduce the value of $\Delta E_{ST}$, in principle, reducing the spatial overlaps of the highest occupied molecular orbital (HOMO) and the lowest unoccupied molecular orbital (LUMO) in the molecule is most effective.

It is known that in the electronic orbitals of the molecule, the HOMO has a distribution to an electron donating position and the LUMO has a distribution to an electron withdrawing position, in general. By introducing an electron donating skeleton and electron withdrawing skeleton in the molecule, it is possible to keep apart the positions in which the HOMO and the LUMO exist.

In "An advanced stage of organic optoelectronics with the aim of commercialization" OYO BUTURI Vol. 82, No. 6, 2013, for example, by introducing an electron withdrawing skeleton such as a cyano group, a triazine group or the like, and an electron donating skeleton such as a carbazole group, a diphenylamino group or the like, the LUMO and HOMO are respectively made localized.

In addition, it is also effective to reduce the molecular structure change between the ground state and the triplet excited state of the compound. As a method of reducing the structure change, it is effective to allow a compound to be stiff. Stiffness referred to herein means that freely movable portions in the molecule are not abundant such as by prevention of a free rotation of the bond between the rings in the molecule, or by introduction of a condensed ring having a large $\pi$-conjugate plane, for example. In particular, by making the portion participating in the light emission stiffer, it is possible to reduce the molecular structure change in the excited state.

Figure 1B:
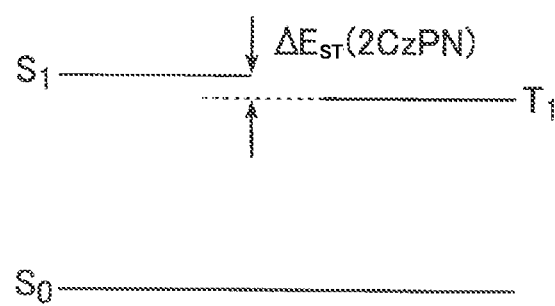
Figure 2A:
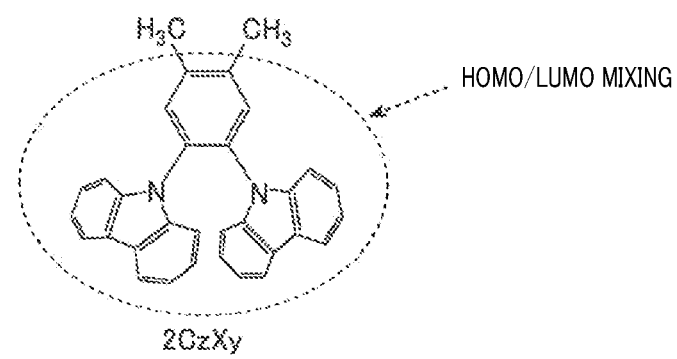
FIG. 2A is a chemical formula of a common fluorescent material and FIG. 2B is a schematic illustration of an energy diagram of the common fluorescent material.
Figure 2B:
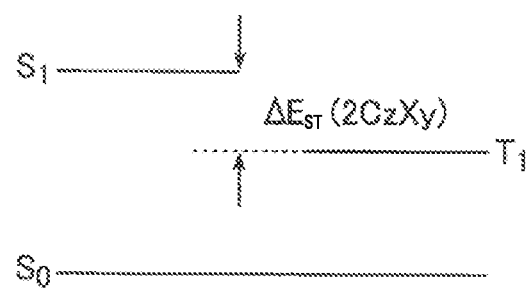

FIG. 1A is a chemical formula of a compound that develops the TADF phenomenon (TADF compound) and FIG. 1B is a schematic illustration of an energy diagram of the TADF compound, and FIG. 2A is a chemical formula of a common fluorescent material and FIG. 2B is a schematic illustration of an energy diagram of the common fluorescent material. For example, in 2CzPN illustrated in FIG. 1A, a HOMO is localized at a carbazolyl group at position 1 and position 2 of the benzene ring, and a LUMO is localized at cyano groups at position 4 and position 5. Thus, the HOMO and the LUMO of 2CzPN may be separated, and $\Delta E_{ST}$ becomes very small to produce the TADF phenomenon. Meanwhile, in 2CzXy, which is produced by substituting cyano groups at position 4 and position 5 of 2CzPN with methyl groups, the HOMO and the LUMO cannot be clearly separated as is seen in 2CzPN, despite of their similar structures. As a result, $\Delta E_{ST}$ cannot be made small, and a TADF phenomenon will not be produced.

A variety of measuring methods concerning a $\pi$-conjugated compound according to the present invention will be described hereinbelow.

[Electron Density Distribution]

In the $\pi$-conjugated compound according to the present invention, the HOMO and the LUMO are preferably substantially separated in the molecule, from the viewpoint of reducing $\Delta E_{ST}$. The distribution of the HOMO and the LUMO can be determined from the electron density distribution when the structure is optimized obtained by molecular orbital calculation.

The structure optimization and calculation of the electron density distribution by molecular orbital calculation of the $\pi$-conjugated compound in the present invention can be carried out by using, as a calculation technique, software for molecular orbital calculation including B3LYP as a functional and 6-31G (d) as a basis function. The software is not particularly limited, and the distribution can be determined similarly by using any software.

In the present invention, Gaussian 09 available from Gaussian Inc., USA (Revision C. 01, M. J. Frisch, et al., Gaussian, Inc., 2010.) was used as the software for molecular orbital calculation.

"The HOMO and the LUMO are substantially separated" means that the center of the HOMO orbital distribution and the center of the LUMO orbital distribution calculated by the molecular calculation described above are apart from each other and more preferably that the distribution of the HOMO orbit and the distribution of the LUMO orbit do not substantially overlap.

In respect of the separation state of the HOMO and the LUMO, from the aforementioned structure optimization calculation including B3LYP as the functional and 6-31G (d) as the basis function, excited state calculation by means of the time-dependent density functional theory (Time-Dependent DFT) is further carried out to determine energy levels of $S_1$ and $T_1$, ($E(S_1)$ and $E(T_1)$, respectively), and thus, the state can be calculated as $\Delta E_{ST}=|E(S_1)-E(T_1)|$. The smaller $\Delta E_{ST}$ calculated indicates that the HOMO and LUMO are more separate from each other. In the present invention, $\Delta E_{ST}$ calculated by using the calculation technique similar to that aforementioned is 0.50 eV or less, preferably 0.30 eV or less, more preferably 0.10 eV or less.

When $\Delta E_{ST}$ is 0.5 eV or less, the $\pi$-conjugated compound in the present invention exhibits thermally activated delayed fluorescence.

<<Constituent Layers of Organic EL Element>>

The organic EL element of the present invention is an organic EL element including an anode, a cathode, and an organic layer including a light-emitting layer sandwiched between the anode and the cathode, wherein the light-emitting layer contains a $\pi$-conjugated compound having a structure represented by any of the general formulas 1 to 3.

Representative element configurations in the organic EL element of the present invention are, but not limited to, as follows.

(1) Anode/Light-emitting layer//Cathode
(2) Anode/Light-emitting layer/Electron transport layer/Cathode (3) Anode/Hole transport layer/Light-emitting layer/Cathode (4) Anode/Hole transport layer/Light-emitting layer/Electron transport layer/Cathode (5) Anode/Hole transport layer/Light-emitting layer/Electron transport layer/Electron injection layer/Cathode (6) Anode/Hole injection layer/Hole transport layer/Light-emitting layer/Electron transport layer/Cathode (7) Anode/Hole injection layer/Hole transport layer/(Electron blocking layer/) Light-emitting layer/(Hole blocking layer/) Electron transport layer/Electron injection layer/Cathode Among the above, the configuration (7) is preferably used, but the structure is not limited thereto.

A light-emitting layer of the present invention is composed of a single layer or a plurality of layers. When the light-emitting layer is composed of a plurality of layers, a non-luminescent intermediate layer(s) may be disposed between light-emitting layers.

As required, a hole blocking layer (also referred to as a hole barrier layer) and/or an electron injection layer (also referred to as a cathode buffer layer) may be disposed between the light-emitting layer and a cathode. Further, an electron blocking layer (also referred to as an electron barrier layer) and/or a hole injection layer (also referred to as an anode buffer layer) may be disposed between the light-emitting layer and an anode. An electron transport layer used for the present invention is a layer having a function of transporting electrons. The electron injection layer and the hole blocking layer are types of the electron transport layer in a broad sense. The electron transport layer may be composed of a plurality of layers.

A hole transport layer of the present invention is a layer having a function of transporting holes. The hole injection layer and the electron blocking layer are types of the hole transport layer in a broad sense. The electron transport layer may be composed of a plurality of layers.

In the representative element configuration described above, the layer from which the anode and the cathode are removed is also referred to as an "organic layer".

(Tandem Structure)

An organic EL element of the present invention may be so-called a tandem structure element in which a plurality of light-emitting units each containing at least one light-emitting layer are layered.

A representative element configuration of the tandem structure is, for example, the following configuration.

Anode/First Light-Emitting Unit/Intermediate Layer/Second Light-Emitting Unit/Intermediate Layer/Third Light-Emitting Unit/Cathode All the first light-emitting unit, second light-emitting unit, and third light-emitting unit described above may be the same or different from each other. Alternatively, two light-emitting units may be the same with the remaining one light-emitting unit different therefrom.

The light-emitting units may be laminated directly or may be laminated through an intermediate layer, which may be referred to as an intermediate electrode, an intermediate conductive layer, a charge generating layer, an electron drawing layer, a connecting layer, or an intermediate insulating layer. Any known material configuration can be used as long as a layer has a function of supplying electrons to an adjacent layer on the anode side and holes to an adjacent layer on the cathode side.

Examples of the material used for the intermediate layer include conductive inorganic compound layers of indium tin oxide (ITO), indium zinc oxide (IZO), $ZnO_2$, TiN, ZrN, HfN, TiOx, VOx, CuI, InN, GaN, $CuAlO_2$, $CuGaO_2$, $SrCu_2O_2$, $LaB_6$, $RuO_2$, and Al, two-layer films of $Au/Bi_2O_3$, multilayer films of $SnO_2/Ag/SnO_2$, $ZnO/Ag/ZnO$, $Bi_2O_3/Au/Bi_2O_3$, $TiO_2/TiN/TiO_2$, and $TiO_2/ZrN/TiO_2$, conductive organic substance layers of fullerenes such as fullerene $C_{60}$ and oligothiophene, and conductive organic compound layers of metal phthalocyanines, metal-free phthalocyanines, metal porphyrins, and metal-free porphyrins. The present invention is not limited thereto.

Examples of a preferable configuration in the light-emitting unit include those formed by removing the anode and the cathode from the representative element configurations (1) to (7) listed above, but the present invention is not limited thereto.

Specific examples of the tandem structure organic EL elements include, for example, the element structure and constituent materials disclosed in the following literature: U.S. Pat. Nos. 6,337,492, 7,420,203, 7,473,923, 6,872,472, 6,107,734, 6,337,492, WO2005/009087, Japanese Patent Application Laid-Open No. 2006-228712, Japanese Patent Application Laid-Open No. 2006-24791, Japanese Patent Application Laid-Open No. 2006-49393, Japanese Patent Application Laid-Open No. 2006-49394, Japanese Patent Application Laid-Open No. 2006-49396, Japanese Patent Application Laid-Open No. 2011-96679, Japanese Patent Application Laid-Open No. 2005-340187, Japanese Patent No. 4711424, Japanese Patent No. 3496681, Japanese Patent No. 3884564, Japanese Patent No. 4213169, Japanese Patent Application Laid-Open No. 2010-192719, Japanese Patent Application Laid-Open No. 2009-076929, Japanese Patent Application Laid-Open No. 2008-078414, Japanese Patent Application Laid-Open No. 2007-059848, Japanese Patent Application Laid-Open No. 2003-272860, Japanese Patent Application Laid-Open No. 2003-045676, WO2005/094130 and the like, but the present invention is not limited thereto.

Hereinafter, the layers constituting the organic EL element of the present invention will be described.

<<Light-Emitting Layer>>

The light-emitting layer used for the present invention is a layer which provides a place of light emission via excitons produced by recombination of electrons and holes injected from the electrodes or the adjacent layers. The luminescent portion may be either in the light-emitting layer or at an interface between the light-emitting layer and the adjacent layer. The configuration of the light-emitting layer used for the present invention is not particularly limited as long as it satisfies the requirements defined by the present invention, that is, as long as it contains a π-conjugated compound having a structure represented by any of the general formulas 1 to 3.

The total thickness of the light-emitting layer(s) is not particularly limited, but is adjusted to be in preferably the range from 2 nm to 5 μm, more preferably the range from 2 nm to 500 nm, still more preferably the range from 5 nm to 200 nm from the viewpoints of homogeneity of layers formed, prevention of application of an unnecessarily high voltage during light emission, and increase in stability of emission colors against drive current.

The thickness of each light-emitting layer used for the present invention is adjusted to be in preferably the range from 2 nm to 1 μm, more preferably the range from 2 nm to 200 nm, still more preferably the range from 3 nm to 150 nm.

The light-emitting layer used for the present invention may be a single layer or may be constituted by a plurality of layers. The π-conjugated compound according to the present invention may be singly used or may be used in mixture with a host compound, a fluorescent material, a phosphorescent material or the like described below. At least one layer of the light-emitting layers preferably contains a luminescent compound (also referred to as a luminescent dopant, a light-emitting dopant, or simply a dopant) and further contains a host compound (also referred to as a matrix material, a luminescent host compound, or simply a host). That at least one layer of the light-emitting layers contains the π-conjugated compound according to the present invention and a host compound is preferred because the emission efficiency is improved. That at least one layer of the light-emitting layers contains the π-conjugated compound according to the present invention and at least one of a fluorescence-emitting compound and a phosphorescence-emitting compound is preferred because the emission efficiency is improved. That at least one layer of the light-emitting layers contains the π-conjugated compound according to the present invention, at least one of a fluorescence-emitting compound and a phosphorescence-emitting compound, and a host compound is preferred because the emission efficiency is improved.

Herein, in the case where the absolute value of the difference between the lowest singlet excited energy level and the lowest triplet excited energy level ($\Delta E_{ST}$) of the π-conjugated compound according to the present invention is 0.50 eV or less, when the π-conjugated compound of the present invention, a luminescent compound, and a host compound are included in the light-emitting layer, the π-conjugated compound according to the present invention serves as an assist dopant. Meanwhile, when the light-emitting layer contains the π-conjugated compound according to the present invention and a luminescent compound and contains no host compound, the π-conjugated compound according to the present invention serves as a host compound. When the light-emitting layer contains only the π-conjugated compound according to the present invention, the π-conjugated compound according to the present invention serves both as a host compound and a luminescent compound. The mechanism by which these effects are exerted is the same in any case and is based on conversion of triplet excitons generated on the π-conjugated compound according to the present invention into single excitons through reverse intersystem crossing (RISC).

Accordingly, the overall exciton energy generated on the π-conjugated compound according to the present invention can theoretically undergo energy transfer to a luminescent compound, resulting in high light emission efficiency.

Thus, when the light-emitting layer contains three components: the π-conjugated compound according to the present invention, a luminescent compound, and a host compound, the energy levels $S_1$ and $T_1$ of the π-conjugated compound are preferably lower than the energy levels $S_1$ and $T_1$ of the host compound and higher than the energy levels $S_1$ and $T_1$ of the luminescent compound.

Similarly, when the light-emitting layer contains two components: the π-conjugated compound according to the present invention and a luminescent compound, the energy levels $S_1$ and $T_1$ of the π-conjugated compound are preferably higher than the energy levels $S_1$ and $T_1$ of the luminescent compound.

Figure 3:
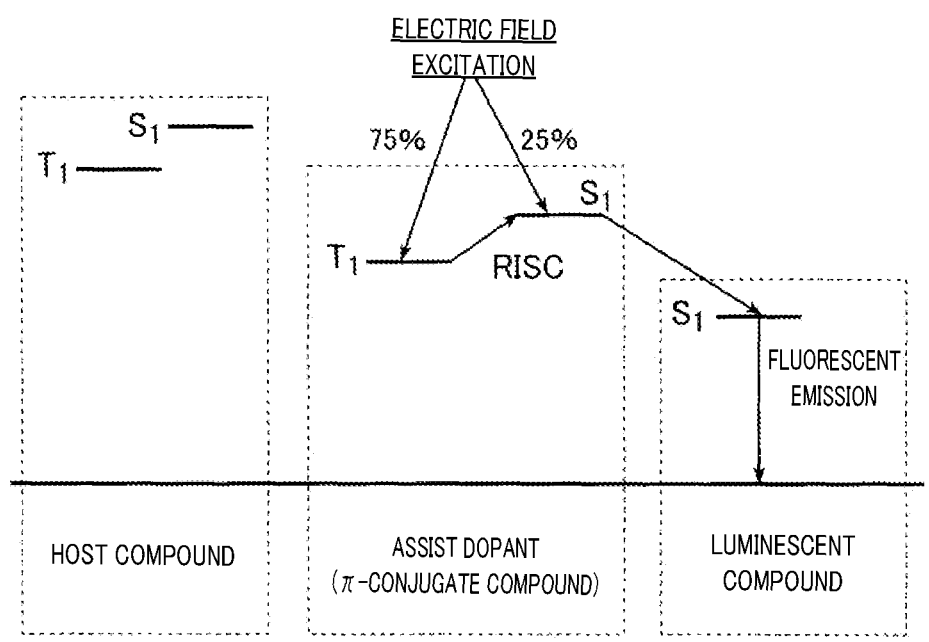
FIG. 3 is a schematic illustration of an energy diagram when a π-conjugated compound serves as an assist dopant material.
Figure 4:
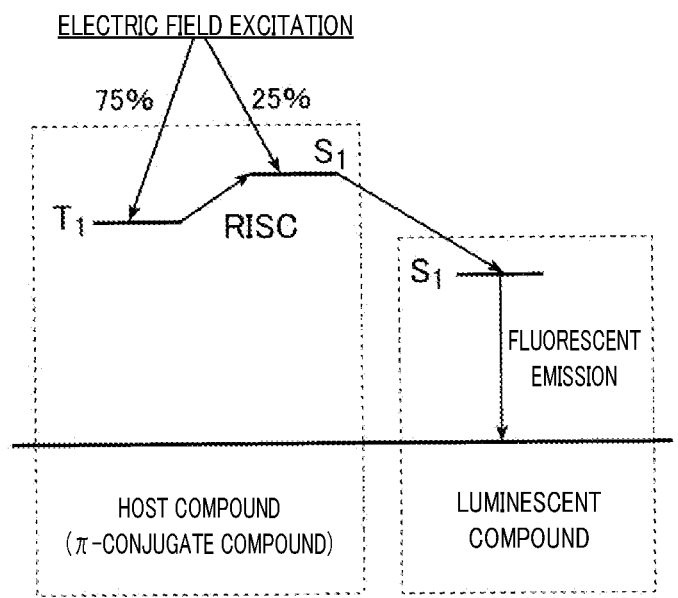
FIG. 4 is a schematic illustration of an energy diagram when the π-conjugated compound serves as a host compound.

FIG. 3 schematically illustrates the case where the π-conjugated compound of the present invention serves as an assist dopant, and FIG. 4 schematically illustrates the case where the compound serves as a host compound. FIGS. 3 and 4 are exemplary. The generation process of triplet excitons generating on the π-conjugated compound according to the present invention is not only through electric-field excitation but also through energy transfer or electron transfer in the light-emitting layer or from the interface between the light-emitting layer and a layer adjacent thereto.

Although FIGS. 3 and 4 illustrate the case where the luminescent compound is a fluorescence-emitting compound, the luminescent compound is not limited thereto. A phosphorescence-emitting compound may be used or both a fluorescence-emitting compound and a phosphorescence-emitting compound may be used.

When the π-conjugated compound according to the present invention is used as an assist dopant, the light-emitting layer preferably contains a host compound in an amount of 100% or more by mass ratio relative to the π-conjugated compound, and a fluorescence-emitting compound and/or a phosphorescence-emitting compound in an amount of 0.1 to 50% by mass ratio relative to the π-conjugated compound.

When the π-conjugated compound according to the present invention is used as a host compound, the light-emitting layer preferably contains a fluorescence-emitting compound and/or a phosphorescence-emitting compound in an amount of 0.1 to 50% by mass ratio relative to the π-conjugated compound.

When the π-conjugated compound according to the present invention is used as an assist dopant or a host compound, the emission spectrum of the π-conjugated compound according to the present invention and the absorption spectrum of the luminescent compound preferably overlap each other.

Emission colors of an organic EL element of the present invention or the compound used for the present invention are determined by applying results obtained with a CS-1000 Spectroradiometer (produced by Konica Minolta Inc.) to the CIE chromaticity coordinates in FIG. 3.16 on page 108 of "Shinpen Shikisai Kagaku Handobukku (New Edition Handbook of Color Science)" (edited by The Color Science Association of Japan, University of Tokyo Press, 1985).

In the present invention, one or more light-emitting layers preferably contain luminescent compounds having different emission colors so that white light is preferably emitted.

A combination of luminescent compounds emitting white light is not particularly limited, and examples thereof include combinations of: blue and orange; and blue, green and red or the like.

The "white" in an organic EL element of the present invention preferably shows chromaticity in the region of x=0.39±0.09 and y=0.38±0.08 in the CIE 1931 Color Specification System at 1,000 cd/m², when 2-degree viewing angle front luminance is measured by the method aforementioned.

(1) Luminescent Compound

As the luminescent compound, a fluorescence-emitting compound (also referred to as a fluorescence-emitting dopant or fluorescent dopant) and a phosphorescence-emitting compound (also referred to as a phosphorescence-emitting dopant and phosphorescent dopant) are preferably used. In the present invention, the light-emitting layer preferably contains the π-conjugated compound according to the present invention as a fluorescence-emitting compound or an assist dopant in the range of 0.1 to 50 mass %, particularly in the range of 1 to 30 mass %. Additionally, in the present invention, the light-emitting layer contains a luminescent compound in the range of 0.1 to 50 mass %, particularly in the range of 1 to 30 mass %.

The concentration of the luminescent compound in the light-emitting layer may be arbitrarily determined based on the specific luminescent compound employed and the requirements of the device. The concentration of the luminescent compound may be contained at a homogeneous concentration in the thickness direction of the light-emitting layer or may have any concentration distribution.

As the luminescent compound used for the present invention, a plurality of luminescent compounds may be used in combination. A combination of fluorescence-emitting compounds having different structures or a combination of a fluorescence-emitting compound and a phosphorescence-emitting compound may be used. Any emission color can be obtained thereby.

(1.1) Fluorescence-Emitting Compound

As the fluorescence-emitting compound (fluorescence-emitting dopant, fluorescent dopant) the π-conjugated compound of the present invention may be used. Alternatively, the fluorescence-emitting compound may be appropriately selected and used from known fluorescence-emitting compounds used for the light-emitting layer of organic EL elements and delayed fluorescent luminescent compounds.

Specific examples of the known fluorescence-emitting compounds that can be used for the present invention include anthracene derivatives, pyrene derivatives, chrysene derivatives, fluoranthene derivatives, perylene derivatives, fluorene derivatives, arylacetylene derivatives, styrylarylene derivatives, styrylamine derivatives, arylamine derivatives, boron complexes, coumarin derivatives, pyrane derivatives, cyanine derivatives, croconium derivatives, squarylium derivatives, oxobenzanthracene derivatives, fluorescein derivatives, rhodamine derivatives, pyrylium derivatives, perylene derivatives, polythiophene derivatives, rare earth complex-based compounds, and the like. In recent years, luminescent compounds making use of delayed fluorescence have been developed, and these may be used. Specific examples of the luminescent compound making use of delayed fluorescence are compounds described in WO2011/156793, Japanese Patent Application Laid-Open No. 2011-213643, Japanese Patent Application Laid-Open No. 2010-93181, Japanese Patent No. 5366106, and the like, but the present invention is not limited thereto.

(1.2) Phosphorescence-Emitting Compound

The phosphorescence-emitting compound used for the present invention will be described.

The phosphorescence-emitting compound used for the present invention is a compound in which the light emission from excited triplets can be observed and, specifically, a compound that emits phosphorescence at room temperature (25° C.). The compound is defined as a compound having a phosphorescence quantum efficiency of 0.01 or more at 25° C., and the phosphorescence quantum efficiency is preferably 0.1 or more.

The phosphorescence quantum efficiency described above can be measured by a method described on page 398 of Bunko II of Dai 4 Han Jikken Kagaku Koza 7 (Spectroscopy II of Lecture of Experimental Chemistry vol. 7, 4th edition) (1992, published by Maruzen Co., Ltd.). The phosphorescence quantum efficiency in a solution can be measured by using various solvents. It is only necessary for the phosphorescence-emitting compound used for the present invention to exhibit the above phosphorescence quantum efficiency (0.01 or more) in any of the solvents.

The phosphorescence-emitting compound can be appropriately selected and used from known phosphorescence-emitting compounds used for light-emitting layers of organic EL elements. Specific examples of the known phosphorescence-emitting compounds usable in the present invention include compounds described in the following literatures.

Nature 395, 151 (1998), Appl. Phys. Lett. 78, 1622 (2001), Adv. Mater. 19, 739 (2007), Chem. Mater. 17, 3532 (2005), Adv. Mater. 17, 1059 (2005), WO2009/100991, WO2008/101842, WO2003/040257, US Patent Application Laid-Open No. 2006-835469, US Patent Application Laid-Open No. 2006-0202194, US Patent Application Laid-Open No. 2007-0087321, US Patent Application Laid-Open No. 2005-0244673, Inorg. Chem. 40, 1704 (2001), Chem. Mater. 16, 2480 (2004), Adv. Mater. 16, 2003 (2004), Angew. Chem. Int. Ed. 2006, 45, 7800, Appl. Phys. Lett. 86, 153505 (2005), Chem. Lett. 34, 592 (2005), Chem. Commun. 2906 (2005), Inorg. Chem. 42, 1248 (2003), WO2009/050290, WO2002/015645, WO2009/000673, US Patent Application Laid-Open No. 2002-0034656, U.S. Pat. No. 7,332,232, US Patent Application Laid-Open No. 2009-0108737, US Patent Application Laid-Open No. 2009-0039776, U.S. Pat. Nos. 6,921,915, 6,687,266, US Patent Application Laid-Open No. 2007-0190359, US Patent Application Laid-Open No. 2006-0008670, US Patent Application Laid-Open No. 2009-0165846, US Patent Application Laid-Open No. 2008-0015355, U.S. Pat. Nos. 7,250,226, 7,396,598, US Patent Application Laid-Open No. 2006-0263635, US Patent Application Laid-Open No. 2003-0138657, US Patent Application Laid-Open No. 2003-0152802, U.S. Pat. No. 7,090,928, Angew. Chem. Int. Ed. 47, 1 (2008), Chem. Mater. 18, 5119 (2006), Inorg. Chem. 46, 4308 (2007), Organometallics 23, 3745 (2004), Appl. Phys. Lett. 74, 1361 (1999), WO2002/002714, WO2006/009024, WO2006/056418, WO2005/019373, WO2005/123873, WO2005/123873, WO2007/004380, WO2006/082742, US Patent Application Laid-Open No. 2006-0251923, US Patent Application Laid-Open No. 2005/0260441, U.S. Pat. Nos. 7,393,599, 7,534,505, 7,445,855, US Patent Application Laid-Open No. 2007/0190359, US Patent Application Laid-Open No. 2008/0297033, U.S. Pat. No. 7,338,722, US Patent Application Laid-Open No. 2002-0134984, U.S. Pat. No. 7,279,704, US Patent Application Laid-Open No. 2006-098120, US Patent Application Laid-Open No. 2006-103874, WO2005/076380, WO2010/032663, WO2008140115, WO2007/052431, WO2011/134013, WO2011/157339, WO2010/086089, WO2009/113646, WO2012/020327, WO2011/051404, WO2011/004639, WO2011/073149, US Patent Application Laid-Open No. 2012-228583, US Patent Application Laid-Open No. 2012-212126, Japanese Patent Application Laid-Open No. 2012-069737, Japanese Patent Application No. 2011-181303, Japanese Patent Application Laid-Open No. 2009-114086, Japanese Patent Application Laid-Open No. 2003-81988, Japanese Patent Application Laid-Open No. 2002-302671, Japanese Patent Application Laid-Open No. 2002-363552 and the like.

Of these, preferable phosphorescence-emitting compounds include an organic metal complex having Ir and Pt as central metal. More preferably, a complex containing at least one coordination mode of a metal-carbon bond, metal-nitrogen bond, metal-oxygen bond, or metal-sulfur bond.

(2) Host Compound

The host compound used for the present invention is a compound which is mainly responsible for injecting and transporting charges in the light-emitting layer. In an organic EL element, light emission from the host compound itself is not observed substantially.

The host compound in the layer preferably has a mass ratio of 20% or more relative to the compounds contained in the light-emitting layer.

The host compound may be singly used or two or more thereof may be used in combination. Use of a plurality of host compounds enables adjustment of charge transfer, thereby increasing the efficiency of the organic EL element.

A host compound preferably used for the present invention will be described hereinbelow.

As the host compound, the π-conjugated compound of the present invention as described above may be used, and the host compound is not particularly limited. From the viewpoint of a reverse energy transfer, those having excited energy higher than the excited singlet energy of the luminescent compound are preferred, and those having excited triplet energy higher than the excited triplet energy of the luminescent compound are more preferred.

The host compound, in a light-emitting layer, is responsible for transporting carriers and generating excitons. Thus, preferably, the host compound can exist stably in all of the active species of a cation radical state, anion radial state, and excited state and causes no chemical reactions such as decomposition and addition. Further, the host molecule preferably will not move in the layer at an Angstrom level when an electric current is applied.

In particular, when the luminescent compound to be used in combination exhibits TADF emission, due to the long lifetime of the triplet excited state of the TADF compound, an appropriate design of a molecular structure is required to prevent the host compound from having a lower $T_1$ level such that the host compound has a high $T_1$ energy level; that the host compounds will not form a low $T_1$ state when associated with each other; that the TADF compound and the host compound will not form an exciplex; and that the host compound will not form an electromer by applying an electric field, for example.

In order to satisfy such requirements, it is required that: the host compound itself have a high electron hopping mobility; the host compound have a high hole hopping mobility; and the host compound have small structural change when it is brought into a triplet excited state. Examples of a representative host compound satisfying these requirements preferably include compounds having a high $T_1$ energy level, such as compounds having a carbazole skeleton, azacarbazole skeleton, dibenzofuran skeleton, dibenzothiophene skeleton, or azadibenzofuran skeleton.

The host compound preferably has a high glass transition temperature (Tg) from the viewpoints of having a hole transporting ability and an electron transporting ability, preventing lengthening of an emission wavelength, and additionally stably operating an organic EL element when the element is driven at high temperature or against heat generated while the element is driven. The compound has a Tg of 90° C. or more, more preferably of 120° C. or more.

The glass transition temperature (Tg) herein is a value obtained using differential scanning colorimetry (DSC) by a method in conformity to JIS-K-7121-2012.

Also as the host compound used for the present invention, the π-conjugated compound according to the present invention may be suitably used as aforementioned. This is because the π-conjugated compound according to the present invention, which has high $T_1$, can be suitably used for light-emitting materials having a short emission wavelength (i.e., high energy levels $T_1$ and $S_1$).

When a known host compound is used for the organic EL element of the present invention, specific examples thereof include compounds described in the following literatures, but the present invention is not limited thereto.

Japanese Patent Application Laid-Open No. 2001-257076, Japanese Patent Application Laid-Open No. 2002-308855, Japanese Patent Application Laid-Open No. 2001-313179, Japanese Patent Application Laid-Open No. 2002-319491, Japanese Patent Application Laid-Open No. 2001-357977, Japanese Patent Application Laid-Open No. 2002-334786, Japanese Patent Application Laid-Open No. 2002-8860, Japanese Patent Application Laid-Open No. 2002-334787, Japanese Patent Application Laid-Open No. 2002-15871, Japanese Patent Application Laid-Open No. 2002-334788, Japanese Patent Application Laid-Open No. 2002-43056, Japanese Patent Application Laid-Open No. 2002-334789, Japanese Patent Application Laid-Open No. 2002-75645, Japanese Patent Application Laid-Open No. 2002-338579, Japanese Patent Application Laid-Open No. 2002-105445, Japanese Patent Application Laid-Open No. 2002-343568, Japanese Patent Application Laid-Open No. 2002-141173, Japanese Patent Application Laid-Open No. 2002-352957, Japanese Patent Application Laid-Open No. 2002-203683, Japanese Patent Application Laid-Open No. 2002-363227, Japanese Patent Application Laid-Open No. 2002-231453, Japanese Patent Application Laid-Open No. 2003-3165, Japanese Patent Application Laid-Open No. 2002-234888, Japanese Patent Application Laid-Open No. 2003-27048, Japanese Patent Application Laid-Open No. 2002-255934, Japanese Patent Application Laid-Open No. 2002-260861, Japanese Patent Application Laid-Open No. 2002-280183, Japanese Patent Application Laid-Open No. 2002-299060, Japanese Patent Application Laid-Open No. 2002-302516, Japanese Patent Application Laid-Open No. 2002-305083, Japanese Patent Application Laid-Open No. 2002-305084, Japanese Patent Application Laid-Open No. 2002-308837, US Patent Application Laid-Open No. 2003/0175553, US Patent Application Laid-Open No. 2006/0280965, US Patent Application Laid-Open No. 2005/0112407, US Patent Application Laid-Open No. 2009/0017330, US Patent Application Laid-Open No. 2009/0030202, US Patent Application Laid-Open No. 2005/0238919, WO2001/039234, WO2009/021126, WO2008/056746, WO2004/093207, WO2005/089025, WO2007/063796, WO2007/063754, WO2004/107822, WO2005/030900, WO2006/114966, WO2009/086028, WO2009/003898, WO2012/023947, Japanese Patent Application Laid-Open No. 2008-074939, Japanese Patent Application Laid-Open No. 2007-254297, European Patent No. 2034538, WO2011/055933, WO2012/035853, Japanese Patent Application Laid-Open No. 2015-38941, and the like.

Hereinafter, as the host compound used in the present invention, specific examples of the host compound will be listed, but the host compounds are not limited thereto.

[Formula 23]

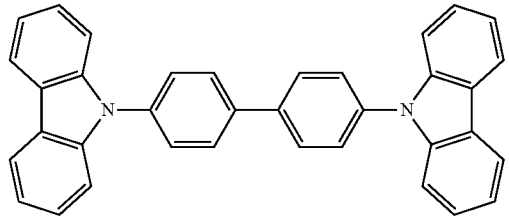

CBP

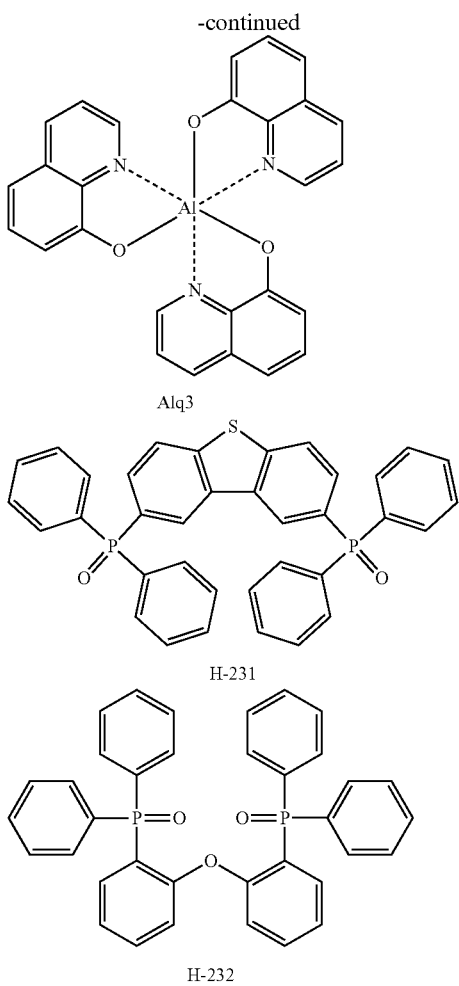

Alq3

H-231

H-232

<<Electron Transport Layer>>

An electron transport layer in the present invention is only required to be composed of a material having a function of transporting an electron and have a function of transferring an injected electron from a cathode to a light-emitting layer.

A total layer thickness of the electron transport layer according to the present invention is not particularly limited. The total thickness is usually in the range of 2 nm to 5 μm, preferably in the range of 2 to 500 nm, more preferably in the range of 5 to 200 nm.

In an organic EL element, it is known that, at the moment of extracting light produced in the light-emitting layer from the electrode, there occurs interference between light directly extracted from the light-emitting layer and light extracted after reflected at the electrode located at the opposite side of the electrode from which the light is extracted. When light is reflected at the cathode, it is possible to use effectively this interference effect by suitably adjusting the total thickness of the electron transport layer in the range of several nm to several μm.

On the other hand, the voltage will be increased when the layer thickness of the electron transport layer is made thick. Therefore, especially when the layer thickness is large, the electron mobility in the electron transport layer is preferably $10^{-5}$ cm$^2$/Vs or more.

As a material used for an electron transport layer (hereinafter, referred to as an electron transport material), it is only required to have either a property of injecting or transporting electrons or a barrier property against holes. Any of the conventionally known compounds can be selected and used.

Examples of the material include nitrogen-containing aromatic heterocycle derivatives (carbazole derivatives, azacarbazole derivatives (formed such that one or more carbon atoms of a carbazole ring are substituted by a nitrogen atom(s)), pyridine derivatives, pyrimidine derivatives, pyrazine derivatives, pyridazine derivatives, triazine derivatives, quinoline derivatives, quinoxaline derivatives, phenanthroline derivatives, azatriphenylene derivatives, oxazole derivatives, thiazole derivatives, oxadiazole derivatives, thiadiazole derivatives, triazole derivatives, benzimidazole derivatives, benzoxazole derivatives, and benzothiazole derivatives), dibenzofuran derivatives, dibenzothiophene derivatives, silole derivatives, and aromatic hydrocarbon ring derivatives (naphthalene derivatives, anthracene derivatives, and triphenylene derivatives).

Further, metal complexes each having a ligand of a quinolinol skeleton or dibnenzoquinolinol skeleton such as tris(8-quinolinol)aluminum (Alq), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum, bis(8-quinolinol)zinc (Znq) and the like; and metal complexes each formed such that central metal of each of the above metal complexes is substituted by In, Mg, Cu, Ca, Sn, Ga, or Pb can also be used as an electron transport material.

Further, metal-free or metal phthalocyanine, or a phthalocyanine derivative whose terminal is substituted by an alkyl group, sulfonic acid group or the like can be preferably utilized as an electron transport material. In addition, a distyrylpyradine derivative which was cited as a light emitting material can be used as an electron transport material. Similarly to the case of a hole injection layer and to the case of a hole transfer layer, an inorganic semiconductor such as an n-type-Si and n-type-SiC can be also utilized as an electron transport material.

Polymer materials, in which these materials are introduced in a polymer chain or these materials form the main chain of a polymer, can be also utilized.

In the electron transport layer according to the present invention, the electron transport layer may be doped with a doping material as a guest material so as to form an (electron-rich) electron transport layer having a high n property. Examples of the doping material include n-type dopants, for example, metal compounds such as a metal complex and a metal halide. Specific examples of the electron transport layer having such a configuration include those described in literatures such as Japanese Patent Application Laid-Open Nos. 4-297076, 10-270172, 2000-196140, and 2001-102175; and J. Appl. Phys., 95, 5773 (2004).

Specific examples of the known electron transport materials preferably used for an organic EL element of the present invention include compounds described in the following literatures, but the present invention is not limited thereto.

U.S. Pat. Nos. 6,528,187, 7,230,107, US Patent Application Laid-Open No. 2005-0025993, US Patent Application Laid-Open No. 2004-0036077, US Patent Application Laid-Open No. 2009-0115316, US Patent Application Laid-Open No. 2009-0101870, US Patent Application Laid-Open No. 2009-0179554, WO2003/060956, WO2008/132085, Appl. Phys. Lett. 75, 4 (1999), Appl. Phys. Lett. 79, 449 (2001), Appl. Phys. Lett. 81, 162 (2002), Appl. Phys. Lett. 81, 162 (2002), Appl. Phys. Lett. 79, 156 (2001), U.S. Pat. No. 7,964,293, US Patent Application Laid-Open No. 2009-

030202, WO2004/080975, WO2004/063159, WO2005/085387, WO2006/067931, WO2007/086552, WO2008/114690, WO2009/069442, WO2009/066779, WO2009/054253, WO2011/086935, WO2010/150593, WO2010/047707, European Patent No. 2311826, Japanese Patent Application Laid-Open No. 2010-251675, Japanese Patent Application Laid-Open No. 2009-209133, Japanese Patent Application Laid-Open No. 2009-124114, Japanese Patent Application Laid-Open No. 2008-277810, Japanese Patent Application Laid-Open No. 2006-156445, Japanese Patent Application Laid-Open No. 2005-340122, Japanese Patent Application Laid-Open No. 2003-45662, Japanese Patent Application Laid-Open No. 2003-31367, Japanese Patent Application Laid-Open No. 2003-282270, WO2012/115034 and the like.

Examples of a more preferably known electron transport material in the present invention include aromatic heterocyclic compounds containing at least one nitrogen atom and compounds containing a phosphorous atom, such as pyridine derivatives, pyrimidine derivatives, pyrazine derivatives, triazine derivatives, dibenzofuran derivatives, dibenzothiophene derivatives, azadibenzofuran derivatives, azadibenzothiophene derivatives, carbazole derivatives, azacarbazole derivatives, benzimidazole derivatives, and arylphosphine oxide derivatives.

The electron transport material may be singly used or two or more thereof may be used in combination.

<<Hole Blocking Layer>>

The hole blocking layer is a layer having a function of the electron transport layer in a broad sense. The hole blocking layer is preferably composed of a material having a function of transporting electrons with a small ability of transporting holes and can increase the recombination probability of electrons and holes by blocking holes while transporting electrons.

The configuration of the electron transport layer described above can be used for the hole blocking layer of the present invention as required.

The hole blocking layer disposed in an organic EL element of the present invention is preferably disposed adjacent to the light-emitting layer on the cathode side.

The thickness of the hole blocking layer according to the present invention is preferably in the range of 3 nm to 100 nm, more preferably in the range of 5 nm to 30 nm.

As the material used for the hole blocking layer, the materials used for the electron transport layer aforementioned are preferably used, and the materials used as the host compound aforementioned are also preferably used for the hole blocking layer.

<<Electron Injection Layer>>

The electron injection layer (also referred to as a "cathode buffer layer") of the present invention is a layer disposed between the cathode and the light-emitting layer for reduction in drive voltage and increase in emission luminance, which is detailed in Part 2, Chapter 2 "Denkyoku Zairyo (Electrode Material)" (pp. 123-166) of "Yuki EL Soshi To Sono Kogyoka Saizensen (Organic EL Element and Front of Industrialization thereof) (Nov. 30, 1998, published by N.T.S Co., Ltd.)".

In the present invention, the electron injection layer may be provided as required and, as described above, may be present between the cathode and the light-emitting layer or between the cathode and the electron transport layer.

The electron injection layer is preferably a very thin film. The thickness thereof is preferably in the range of 0.1 nm to 5 nm depending on the material thereof. The layer may be an inhomogeneous layer (film) in which the constituent material intermittently exists.

The electron injection layer is also detailed in Japanese Patent Application Laid-Open Nos. 6-325871, 9-17574, 10-74586 and the like, and specific examples of a material preferably used for the electron injection layer include metals represented by strontium and aluminum, alkali metal compounds represented by lithium fluoride, sodium fluoride, and potassium fluoride, alkali earth metal compounds represented by magnesium fluoride and calcium fluoride, metal oxides represented by aluminum oxide, and metal complexes represented by lithium 8-hydroxyquinolinate (Liq). The electron transport materials aforementioned may also be used therefor.

The materials used for the electron injection layer described above may be singly used or two or more thereof may be used in combination.

<<Hole Transport Layer>>

The hole transport layer in the present invention is composed of a material having a function of transporting holes and is only required to have a function of transmitting holes injected from the anode to the light-emitting layer.

The total thickness of the hole transport layer according to the present invention is not particularly limited and usually in the range of 5 nm to 5 μm, more preferably in the range 2 nm to 500 nm, still more preferably in the range of 5 nm to 200 nm.

The material used for the hole transport layer (hereinafter, referred to as the hole transport material) is only required to have either a property of injecting or transporting holes or a barrier property against electrons. Any of conventionally known compounds can be selected and used.

Examples thereof include porphyrin derivatives, phthalocyanine derivatives, oxazole derivatives, oxadiazole derivatives, triazole derivatives, imidazole derivatives, pyrazoline derivatives, pyrazolone derivatives, phenylenediamine derivatives, hydrazone derivatives, stilbene derivatives, polyarylalkane derivatives, triarylalkane derivatives, carbazole derivatives, indolocarbazole derivatives, isoindole derivatives, acene-based derivatives such as anthracene and naphthalene, fluorene derivatives, fluorenone derivatives, polyvinyl carbazole, polymers or oligomers in which aromatic amine is introduced to a main chain or a side chain, polysilane, and conductive polymers or oligomers (such as PEDOT/PSS, aniline-based copolymers, polyaniline, and polythiophene).

Examples of the triarylamine derivative include benzidine types represented by α-NPD (4,4'-bis[N-(1-naphthyl)-N-phenylamino]biphenyl), star-burst types represented by MTDATA, compounds having fluorenone or anthracene at a triarylamine linking core portion.

Hexaazatriphenylene derivatives described in Japanese Unexamined Patent Application Publication (Translation of PCT Application) No. 2003-519432, Japanese Patent Application Laid-Open No. 2006-135145 and the like can also be used as the hole transport material.

The hole transport layer doped with impurities, thereby having a high p property can also be used. Examples thereof include those described in Japanese Patent Application Laid-Open Nos. 4-297076, 2000-196140, and 2001-102175, and J. Appl. Phys., 95, 5773 (2004) and the like.

It is also possible to use so-called p-type hole transport materials described in literatures such as Japanese Patent Application Laid-Open No. 11-251067 and Appl. Phys. Lett. 80 (2002), p. 139 by J. Huang et al., and inorganic compounds such as a p-type-Si and a p-type-SiC. Further, an ortho-metalated organic metal complex having Ir or Pt as central metal, represented by Ir(ppy)3, is also preferably used.

The materials described above can be used as the hole transport material, and preferably used are triarylamine derivatives, carbazole derivatives, indolocarbazole derivatives, azatriphenylene derivatives, organic metal complexes, polymer materials or oligomers in which aromatic amine is introduced to a main chain or a side chain and the like.

Specific examples of the known hole transport materials preferably used in an organic EL element of the present invention also include compounds described in the following literatures in addition to the above literatures, but the present invention is not limited thereto.

For example, Appl. Phys. Lett. 69, 2160 (1996), J. Lumin. 72-74, 985 (1997), Appl. Phys. Lett. 78, 673 (2001), Appl. Phys. Lett. 90, 183503 (2007), Appl. Phys. Lett. 51, 913 (1987), Synth. Met. 87, 171 (1997), Synth. Met. 91, 209 (1997), Synth. Met. 111, 421 (2000), SID Symposium Digest, 37, 923 (2006), J. Mater. Chem. 3, 319 (1993), Adv. Mater. 6, 677 (1994), Chem. Mater. 15, 3148 (2003), US Patent Application Laid-Open No. 2003-0162053, US Patent Application Laid-Open No. 2002-0158242, US Patent Application Laid-Open No. 2006-0240279, US Patent Application Laid-Open No. 2008-0220265, U.S. Pat. No. 5,061,569, WO2007/002683, WO2009/018009, EP No. 650955, US Patent Application Laid-Open No. 2008-0124572, US Patent Application Laid-Open No. 2007-0278938, US Patent Application Laid-Open No. 2008-0106190, US Patent Application Laid-Open No. 2008-0018221, WO2012/115034, Japanese Unexamined Patent Application Publication (Translation of PCT Application) No. 2003-519432, Japanese Patent Application Laid-Open No. 2006-135145, Japanese Patent Application No. 13-585981 and the like.

The hole transport materials may be singly used or two or more thereof may be used in combination.

<<Electron Blocking Layer>>

The electron blocking layer is a layer having a function of the hole transport layer in a broad sense. The electron blocking layer is preferably composed of a material having a function of transporting holes with a small ability of transporting electrons and can increase the recombination probability of electrons and holes by blocking electrons while transporting holes.

The configuration of the hole transport layer described above can be used for the electron blocking layer of the present invention as required.

The electron blocking layer disposed in an organic EL element of the present invention is preferably disposed adjacent to the light-emitting layer on the anode side.

The thickness of the electron blocking layer according to the present invention is preferably in the range of 3 nm to 100 nm, more preferably in the range of 5 nm to 30 nm.

As the material used for the electron blocking layer, the materials used for the hole transport layer aforementioned are preferably used, and the host compound aforementioned is also preferably used for the electron blocking layer.

<<Hole Injection Layer>>

The hole injection layer (also referred to as the "anode buffer layer") according to the present invention is a layer disposed between the anode and the light-emitting layer for reduction in drive voltage and increase in emission luminance, which is detailed in Part 2, Chapter 2 "Denkyoku Zairyo (Electrode Material)" (pp. 123-166) of "Yuki EL Soshi To Sono Kogyoka Saizensen (Organic EL Element and Front of Industrialization thereof) (Nov. 30, 1998, published by N.T.S Co., Ltd.)".

In the present invention, the hole injection layer may be provided as required and, as described above, may be present between the anode and the light-emitting layer or between the anode and the hole transport layer.

The hole injection layer is also detailed in documents such as Japanese Patent Application Laid-Open Nos. 9-45479, 9-260062, and 8-288069, and examples of a material used for the hole injection layer include the materials used for the hole transport layer aforementioned.

Of these, preferable are phthalocyanine derivatives represented by copper phthalocyanine, hexaazatriphenylene derivatives described in Japanese Unexamined Patent Application Publication (Translation of PCT Application) No. 2003-519432 and Japanese Patent Application Laid-Open No. 2006-135145 and the like, metal oxides represented by vanadium oxide, amorphous carbon, conductive polymers such as polyaniline (emeraldine) and polythiophene, ortho-metalated complexes represented by a tris(2-phenylpyridine) iridium complex, triarylamine derivatives and the like.

The materials used for the hole injection layer aforementioned may be singly used or two or more thereof may be used in combination.

<<Additives>>

The organic layers aforementioned in the present invention may further include other additives.

Examples of the additives include halogen elements such as bromine, iodine, and chlorine, halogenated compounds, and compounds, complexes, and salts of alkali metals, alkali earth metals, and transition metals such as Pd, Ca, and Na.

The content of the additives can be optionally determined, and is preferably 1,000 ppm or less, more preferably 500 ppm or less, still more preferably 50 ppm or less based on the total mass % of the layer in which the additives are included.

Depending on the purpose of improving the property of transporting electrons or holes or the purpose of facilitating energy transfer of excitons, other ranges may be used.

<<Method for Forming Organic Layers>>

A method for forming organic layers according to the present invention (hole injection layer, hole transport layer, light-emitting layer, hole blocking layer, electron transport layer, electron injection layer, intermediate layer, and the like) will be described.

The method for forming organic layers according to the present invention is not specifically limited. There can be employed conventionally known forming methods such as a vacuum vapor deposition method, wet method (also referred to as a wet process) and the like.

Examples of the wet method include a spin coating method, cast method, ink jetting method, printing method, die coating method, blade coating method, roll coating method, spray coating method, curtain coating method, and LB method (Langmuir Blodgett method). Preferred are processes highly suitable for a roll-to-roll system, such as a die coating method, roll coating method, ink jetting method, spray coating method and the like, from the viewpoint of easy formation of a homogeneous thin film and high productivity.

Examples of the liquid medium that can be used for dissolving or dispersing of the organic EL materials used for the present invention include ketones such as methyl ethyl ketone and cyclohexanone, fatty acid esters such as ethyl acetate, halogenated hydrocarbons such as dichlorobenzene, aromatic hydrocarbons such as toluene, xylene, mesitylene, and cyclohexylbenzene, aliphatic hydrocarbons such as cyclohexane, decalin, and dodecane, and organic solvents such as DMF and DMSO.

Examples of the usable dispersion technique include ultrasonic dispersion, high shearing force dispersion, and medium dispersion.

Further, different layers may be formed through different processes. If a layer is formed by a deposition process, appropriate deposition conditions, which may vary depending on the type of a compound used, are preferably selected as appropriate from generally the following ranges: a boat heating temperature of 50 to 450° C., a vacuum of $10^{-6}$ to $10^{-2}$ Pa, a deposition rate of 0.01 to 50 nm/second, a substrate temperature of −50 to 300° C., and a layer thickness of 0.1 nm to 5 µm, preferably 5 to 200 nm.

Formation of organic layers according to the present invention is preferably continuously carried out from a hole injection layer to a cathode with one time vacuuming. The layers may be taken out on the way, and a different layer forming method may be employed. In this case, the operation is preferably done under a dry inert gas atmosphere.

<<Anode>>

The anode of the organic EL element is preferably formed of, as an electrode material, metal, alloy or conductive compound each having a large work function (4 eV or more, preferably 4.5 eV or more), or a mixture thereof. Specific examples of such an electrode material include metals such as Au, and transparent electroconductive materials such as CuI, indium tin oxide (ITO), $SnO_2$, and ZnO. A material that is amorphous and capable of forming a transparent conductive layer such as IDIXO ($In_2O_3$—ZnO) or the like may be used.

The anode may be formed in such a manner that the electrode material is formed into a thin film by a method as vapor deposition or sputtering, and the film is patterned into a desired pattern by a photolithography method. Alternatively, in the case where the pattern may not require high accuracy (for example, approximately 100 µm or more), the pattern may be formed with a mask having a desired shape on vapor deposition or sputtering of the electrode material.

In the case of using a material capable of being applied as a coating, such as an organic electroconductive compound, a wet film forming method, such as a printing method and coating method, may be used. In the case where emitted light is to be taken out through the anode, the anode preferably has a transmittance of more than 10%, and preferably has a sheet resistance of several hundred Ohms per square or less.

The thickness thereof may be generally selected from the range of 10 nm to 1 µm, preferably of 10 to 200 nm, while depending on the material used.

<<Cathode>>

The cathode is preferably formed of, as an electrode material, a metal (referred to as an electron injection metal), an alloy or a conductive compound each having a small work function (4 eV or less), or a mixture thereof. Specific examples of the electrode material include sodium, sodium-potassium alloys, magnesium, lithium, magnesium-copper mixtures, magnesium-silver mixtures, magnesium-aluminum mixtures, magnesium-indium mixtures, aluminum/aluminum oxide ($Al_2O_3$) mixtures, indium, lithium/aluminum mixtures, aluminum, and rare earth metals. Of these, mixtures of an electron injection metal and a second metal that is a stable metal having a larger work function than the electron injection metal, for example, magnesium/silver mixtures, magnesium/aluminum mixtures, magnesium/indium mixtures, aluminum/aluminum oxide ($Al_2O_3$) mixtures, lithium/aluminum mixtures, aluminum and the like are preferred in respect of the electron injection property and the durability against oxidation and the like.

The cathode can be produced by forming the electrode material into a thin film by a method such as vapor deposition or sputtering. The cathode preferably has a sheet resistance of several hundred Ohms per square or less, and the thickness thereof may be usually selected from the range of from 10 nm to 5 µm, preferably of 50 to 200 nm.

For transmitting the emitted light, any one of the anode and the cathode of the organic EL element is preferably transparent or translucent, thereby enhancing the emission luminance.

After the metal described above has been formed into a film having a thickness of from 1 nm to 20 nm as a cathode, the conductive transparent material mentioned in the description of the anode is formed into a film on the cathode, thereby being able to produce a transparent or translucent cathode. Through the application of this method, an element in which both the anode and cathode have transparency can be produced.

[Supporting Substrate]

The supporting substrate (also referred to as a substrate or a base material hereinafter) that can be used for the organic EL element of the present invention may be composed of glass or plastic, which may be of any type and may be transparent or opaque. For extraction of light from the supporting substrate side, the supporting substrate is preferably transparent. Examples of the transparent supporting substrate preferably used include glass, quartz, and transparent resin films. A particularly preferred supporting substrate is a resin film capable of imparting flexibility to the organic EL element.

Examples of the resin film include films of polyesters such as polyethylene terephthalate (PET) and polyethylene naphthalate (PEN), polyethylene, polypropylene, cellophane, cellulose esters and their derivatives such as cellulose diacetate, cellulose triacetate (TAC), cellulose acetate butyrate, cellulose acetate propionate (CAP), cellulose acetate phthalate, and cellulose nitrate, polyvinylidene chloride, polyvinyl alcohol, poly(ethylene-vinyl alcohol), syndiotactic polystyrene, polycarbonate, norbornene resin, polymethylpentene, polyether ketone, polyimide, polyether sulfone (PES), polyphenylene sulfide, polysulfones, polyether imide, polyether ketone imide, polyamide, fluorine resin, Nylon, poly(methyl methacrylate), acrylic and polyarylates and cycloolefin resins such as ARTON (trade name, manufactured by JSR Corp.), and APEL (trade name, manufactured by Mitsui Chemicals Inc.).

On the surface of the resin film, an inorganic or organic coating film or hybrid coating film composed of the both may be formed. The coating film is preferably a barrier film having a water vapor transmittance (permeability) of 0.01 $g/m^2 \cdot 24$ h or less (at 25±0.5° C. and 90±2% relative humidity (RH)) measured by a method in accordance with JIS K 7129-1992, and more preferably a high barrier film having an oxygen transmittance of $1 \times 10^{-3}$ $mL/m^2 \cdot 24$ h·atm·or less measured by a method in accordance with JIS K 7126-1987 and a water vapor transmittance of $1 \times 10^{-5}$ $g/m^2 \cdot 24$ h or less.

As for the material for forming the barrier film, any material that can block infiltration of substances such as moisture and oxygen causing degradation of the element can be used, and examples of the material that can be used include silicon oxide, silicon dioxide, and silicon nitride. In order to improve the fragility of the film, a barrier film is more preferably allowed to have a laminate structure composed of the inorganic layer and organic material layer. The inorganic layer and the organic layer may be laminated in any order, and the both layers are preferably alternately laminated multiple times.

The method for forming the barrier film is not particularly limited, and examples thereof include vacuum deposition, sputtering, reactive sputtering, molecular beam epitaxy, cluster ion-beam deposition, ion plating, plasma polymerization, atmospheric pressure plasma polymerization, plasma CVD, laser CVD, thermal CVD, and coating methods. A particularly preferred method is atmospheric pressure plasma polymerization as described in Japanese Patent Application Laid-Open No. 2004-68143A.

Examples of the opaque supporting substrate include sheets and films of metal such as aluminum and stainless steel, opaque resin substrates, and substrates of ceramic.

The external extraction quantum efficiency of emission of the organic EL element of the present invention at room temperature (25° C.) is preferably 1% or more, more preferably 5% or more.

Herein, the external extraction quantum efficiency (%)= (number of photons emitted from the organic EL element to the exterior)/(number of electrons supplied to the organic EL element)×100.

A hue improving filter such as a color filter or a color conversion filter that converts the color of light emitted by the organic EL element to many colors using a fluorescent compound may be used in combination.

[Sealing]

Examples of the sealing means used in the organic EL element of the present invention include a method in which a sealing member, electrodes, and a supporting substrate are bonded with an adhesive. It is only required to dispose the sealing member so as to cover a displaying area of the organic EL element, and the sealing member may be in the form of a recess or flat plate. Further, the sealing member may have any transparency and electrical insulation.

Examples of the sealing member include glass plates, polymer plates and films, and metal plates and films. Examples of the glass plate include soda-lime glass, barium·strontium-containing glass, lead glass, aluminosilicate glass, borosilicate glass, barium borosilicate glass, and quartz plates. Examples of the polymer plate include polycarbonate, acryl, polyethylene terephthalate, polyether sulfide, and polysulfone plates. The metal plate may be composed of at one or more metals or alloys selected from the group consisting of stainless steel, iron, copper, aluminum, magnesium, nickel, zinc, chromium, titanium, molybdenum, silicon, germanium, and tantalum.

In the present invention, a polymer film or metal film is preferably used, from the viewpoint of reduction in the film thickness of the organic EL element. The polymer film preferably has an oxygen transmittance of $1\times10^{-3}$ mL/m$^2$·24 h·atm or less measured by a method in compliance with JIS K 7126-1987 and a water vapor transmittance of $1\times10^{-3}$ mL/m$^2$·24 h·atm or less (at 25±0.5° C. and 90±2% relative humidity) measured by a method in compliance with JIS K 7129-1992.

The sealing member is formed into a recessed form by, for example, sand blasting or chemical etching.

Specific examples of the adhesive include photo-curable or thermo-curable adhesives having reactive vinyl groups, such as acrylic acid oligomers and methacrylic acid oligomers and moisture curable adhesives such as 2-cyanoacrylate. Examples thereof also include thermally or chemically curable (two-liquid mixing type) adhesives, such as epoxy adhesives. Examples thereof also include hot-melt polyamide, polyester, and polyolefin adhesives. Examples thereof also include UV curable epoxy resin adhesives of cation curing type.

Since the organic EL element may be degraded by heat treatment, the adhesive can be cured preferably at a temperature from room temperature up to 80° C. A drying agent may be dispersed in the adhesive. The adhesive may be applied to the sealing portion with a commercially available dispenser or by printing such as screen printing.

A sealing film can be preferably prepared as a layer of an inorganic or organic compound. The sealing film is formed on outer side of the electrode opposed to the supporting substrate via an organic layer so as to cover the electrode and the organic layer and to be in contact with the supporting substrate. In this case, the sealing film may be formed of any material that can block infiltration of substances such as water and oxygen that causes degradation of the element, and examples of the material that can be used include silicon oxide, silicon dioxide, and silicon nitride.

In order to further improve the fragility of the film, a sealing film is preferably allowed to have a laminate structure composed of the inorganic layer and organic material. The method for forming these films is not particularly limited, and examples thereof include vacuum deposition, sputtering, reactive sputtering, molecular beam epitaxy, cluster ion-beam deposition, ion plating, plasma polymerization, atmospheric pressure plasma polymerization, plasma CVD, laser CVD, thermal CVD, and coating methods.

The gap between the sealing member and the displaying portion of the organic EL element is preferably filled with, in the case of the form of a gas or liquid phase, an inert gas such as nitrogen or argon or an inactive liquid such as fluorinated hydrocarbon or silicone oil. The gap can be in a vacuum state. Alternatively, the gap may be filled with a hygroscopic compound.

Examples of the hygroscopic compound include metal oxides (such as sodium oxide, potassium oxide, calcium oxide, barium oxide, magnesium oxide, and aluminum oxide), sulfates (such as sodium sulfate, calcium sulfate, magnesium sulfate, and cobalt sulfate), metal halides (such as calcium chloride, magnesium chloride, cesium fluoride, tantalum fluoride, cerium bromide, magnesium bromide, barium iodide, and magnesium iodide), and perchlorates (such as barium perchlorate and magnesium perchlorate). The sulfates, metal halides, and perchlorates are suitably used in the form of anhydride.

[Protective Film, Protective Plate]

In order to enhance the mechanical strength of the element, a protective film or plate may be provided on the outer side of the sealing layer or film opposed to the supporting substrate via the organic layer. Particularly when sealing is achieved by the sealing film, the mechanical strength of the sealing film is not sufficiently high. Thus, such a protective film or plate is preferably provided. Examples of the material used for the protective film or plate include glass plates, polymer plates and films, and metal plates and films similar to those used for sealing. From the viewpoint of reduction in the weight and the film thickness, polymer films are preferably used.

[Technique for Improving Light Extraction]

It is generally said that an organic EL element generates light in a layer having a refractive index higher than air (within the refractive index range of about 1.6 to 2.1) and only about 15% to 20% of the light generated in the light-emitting layer can be extracted. This is because incident light on the interface (interface between a transparent substrate and the air) at an angle θ larger than a critical angle is totally reflected and cannot be extracted from the element, or because light is totally reflected at the interface between the transparent electrode or light-emitting layer and the transparent substrate and is guided to the transparent electrode or the light-emitting layer to escape the light to the side surface of the element.

Examples of techniques for improving the light extraction efficiency include a process of forming irregularities on a surface of a transparent substrate to prevent total reflection at the interface between the transparent substrate and the air (e.g., U.S. Pat. No. 4,774,435); a process of providing light-condensing properties to a substrate to improve the efficiency (e.g., Japanese Patent Application Laid-Open No. 63-314795 A); a process of forming a reflection surfaces on the side surfaces of an element (e.g., Japanese Patent Application Laid-Open No. 1-220394 A); a process of introducing a flat layer between a substrate and a luminescent material to form an anti-reflection layer, wherein the flat layer has a refractive index between the substrate and the luminescent material (e.g., Japanese Patent Application Laid-Open No. 62-172691 A); a process of introducing a flat layer between a substrate and a luminescent material, wherein the flat layer has a refractive index lower than that of the substrate (e.g., Japanese Patent Application Laid-Open No. 2001-202827 A); and a process of forming a diffraction grating between any layers of a substrate, transparent electrode layer, and light-emitting layer (including on the substrate surface facing the exterior) (e.g., Japanese Patent Application Laid-Open No. 11-283751 A).

In the present invention, these processes can be used in combination with the organic EL element of the present invention. The process of introducing a flat layer between a substrate and a luminescent material, wherein the flat layer has a refractive index lower than that of the substrate or the luminescent material or the process of forming a diffraction grating between any layers of a substrate, transparent electrode layer, and light-emitting layer (including on the substrate surface facing the exterior) can be suitably employed.

The present invention can provide an element exhibiting higher luminance or more excellent durability by combining those means.

When a low refractive index medium is allowed to have a thickness greater than light wavelength between a transparent electrode and a transparent substrate, the extraction efficiency of light from the transparent electrode to the exterior increases with decrease in the refractive index of the medium. Examples of materials for the low refractive index layer include aero gel, porous silica, magnesium fluoride, and fluorinated polymer. The refractive index of a transparent substrate usually ranges about 1.5 to 1.7, and thus the refractive index of the low refractive index layer is preferably about 1.5 or less, more preferably 1.35 or less.

The low refractive index medium desirably has a thickness twice or more the wavelength of the light in the medium. This is because when the low refractive index medium has a thickness similar to the wavelength of the light, the electromagnetic waves exuding as evanescent waves penetrate into the substrate, resulting in a reduction in the effect of the low refractive index layer.

The process of introducing a diffraction grating onto the interface at which total reflection occurs or into any media is characterized by being highly effective of improving the light extraction efficiency. In this method, a diffraction grating is introduced between any two layers or in any medium (in the transparent substrate or the transparent electrode) to extract the light generated in the light-emitting layer that cannot exit due to total reflection between the layers and the like, by the use of the property of the diffraction gratings that can change the direction of light to a specific direction different from that of refraction by Bragg diffraction such as primary diffraction or secondary diffraction.

The diffraction grating to be introduced desirably has two-dimensional periodic refractive indices. Because light generated in a light-emitting layer is emitted randomly in all the directions, a general one-dimensional diffraction grating having a periodic refractive index distribution only in the specific direction can diffract only the light traveling in a specific direction and cannot greatly increase the light extraction efficiency.

When the refractive index distribution is allowed to be two-dimensional, light traveling in all directions are diffracted to thereby result in an increase in light extraction efficiency.

The diffraction grating may be introduced between any two layers or in any medium (in the transparent substrate or the transparent electrode), but is desirably introduced near the organic light-emitting layer, which is a site generating light. The period of the diffraction grating is preferably about a half to three times the wavelength of light in the medium. The array of the diffraction grating is preferably two-dimensionally repeated such as a square lattice shape, triangular lattice shape, or honeycomb lattice shape.

[Light-Condensing Sheet]

The organic EL element of the present invention can enhance the luminance in a specific direction by condensing light in this specific direction, for example, in the front direction with respect to the light emitting plane of the element by providing, for example, a micro-lens array structure on the light extraction side of the supporting substrate (substrate) of the element or combining with a so-called light-condensing sheet.

In an example of a micro-lens array, quadrangular pyramids having a side of 30 μm and having a vertex angle of 90 degrees are two-dimensionally arranged on the light extraction side of the substrate. The quadrangular pyramid preferably has a side in the range of 10 μm to 100 μm. A side shorter than this range causes coloration due to the effect of diffraction, while a side longer than this range makes the thickness unfavorably large.

A light-condensing sheet that can be used is one practically used for an LED backlight of a liquid crystal display apparatus, for example. A typical example of the sheet is a brightness enhancing film (BEF) manufactured by SUMITOMO 3M Limited. A prism sheet may have, for example, a shape having triangular stripes with a vertex angle of 90 degrees and a pitch of 50 μm, a shape having a round apex, a shape having randomly changed pitches, or other shapes, formed on a base material.

In order to control the emission angle of light from the organic EL element, a light diffusion plate or film may be used in combination with the light-condensing sheet. For example, a diffusion film (Light-Up) manufactured by KIMOTO Co., Ltd. can be used.

[Applications]

The organic EL element of the present invention can be used as an electronic apparatus, such as a display apparatus, a display, or various light-emitting apparatuses.

Examples of the light-emitting apparatus include, but not limited to, lighting apparatuses (lamps for household use, car room lamps, car external lamps, and light sources for infrared cameras), backlights for watches and liquid crystals, light sources for board advertisements, traffic lights, and optical memory media, light sources for electrophotographic copiers, light sources for optical communication instruments, and light sources for optical sensors. In particular, the organic EL element can be effectively used as a backlight for a liquid crystal display apparatus or a lighting source.

In the organic EL element of the present invention, films may be patterned with a metal mask, by ink-jet printing or the like during film deposition. The patterning may be performed on only the electrodes, on the electrodes and the light-emitting layer, or on all layers of the element. In the production of the element, conventionally known methods can be employed.

<Display Apparatus>

The display apparatus including the organic EL element of the present invention may be monochromatic or multichromatic. Herein, a multichromatic display apparatus will now be described.

In the case of a multichromatic display apparatus, a shadow mask is provided only during formation of the light-emitting layer. The film can be formed on one side by a vacuum deposition method, casting method, spin coating method, ink jetting method, printing method or the like.

In the case of patterning only the light-emitting layer, patterning may be performed by any method. The method is preferably a vacuum deposition method, ink jetting method, spin coating method, or printing method.

The configuration of the organic EL element included in the display apparatus is selected from the exemplary configurations of the organic EL element mentioned above as required.

The method of producing the organic EL element is as shown in one embodiment of the production of the organic EL element of the present invention which has been described above.

When a direct current voltage is applied to the multichromatic display apparatus thus obtained, light emission can be observed by allowing the anode to have a positive (+) polarity and the cathode to have a negative (−) polarity and applying an voltage of about 2 V to 40 V. Application of a voltage of the reverse polarity causes no current to flow and generates no light emission. Alternatively, when an alternating current voltage is applied, light is emitted only in the state of the anode being positive (+) and cathode being negative (−). Meanwhile, the alternating current to be applied may have any wave shape.

The multichromatic display apparatus can be used as a display device, display, or various light emission sources. In a display device or display, full color display can be achieved with three types of organic EL elements that emit blue, red, and green light.

Examples of the display device or display include television sets, personal computers, mobile equipment, AV equipment, teletext displays, and information displays in automobiles. In particular, the display apparatus may be used for displaying still images or moving images. The driving system in the case of using the display apparatus used for playback of moving images may be either a simple matrix (passive matrix) system or an active matrix system.

Examples of the light-emitting apparatus include lamps for household use, car room lamps, car external lamps, light sources for infrared cameras, backlights for watches and liquid crystals, light sources for board advertisements, traffic lights, and optical memory media, light sources for electrophotographic copiers, light sources for optical communication instruments, light sources for optical sensors, and the like, but the present invention is not limited thereto.

Hereinbelow, an example of the display device having the organic EL element of the present invention will be described with reference to accompanying drawings.

Figure 5:
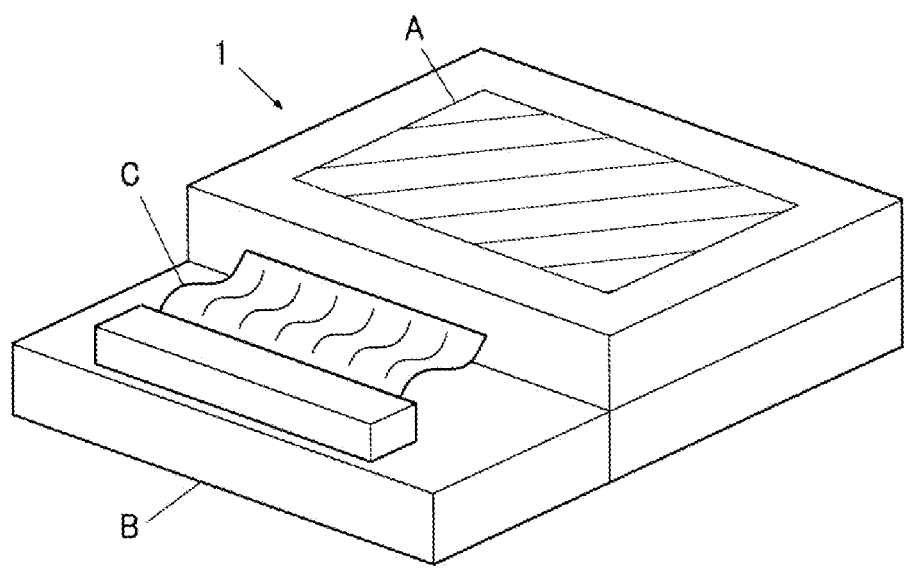
FIG. 5 is a schematic illustration of one exemplary display apparatus constituted by the organic EL element.

FIG. 5 is a schematic illustration of one exemplary display apparatus constituted by the organic EL element. FIG. 5 is a schematic illustration illustrating a display for, for example, a mobile phone to display image information through light emission of the organic EL element.

Display 1 has display part A having a plurality of pixels, control part B to perform image scanning of display part A based on image information, wiring portion C electrically connecting display part A and control part B and the like.

Control part B is electrically connected to display part A via wiring portion C and sends scanning signals and image data signals to each of pixels based on external image information. The pixels of each scanning line sequentially emit light by the scanning signals and in response to the image data signal to perform image scanning, displaying the image information on display part A.

Figure 6:
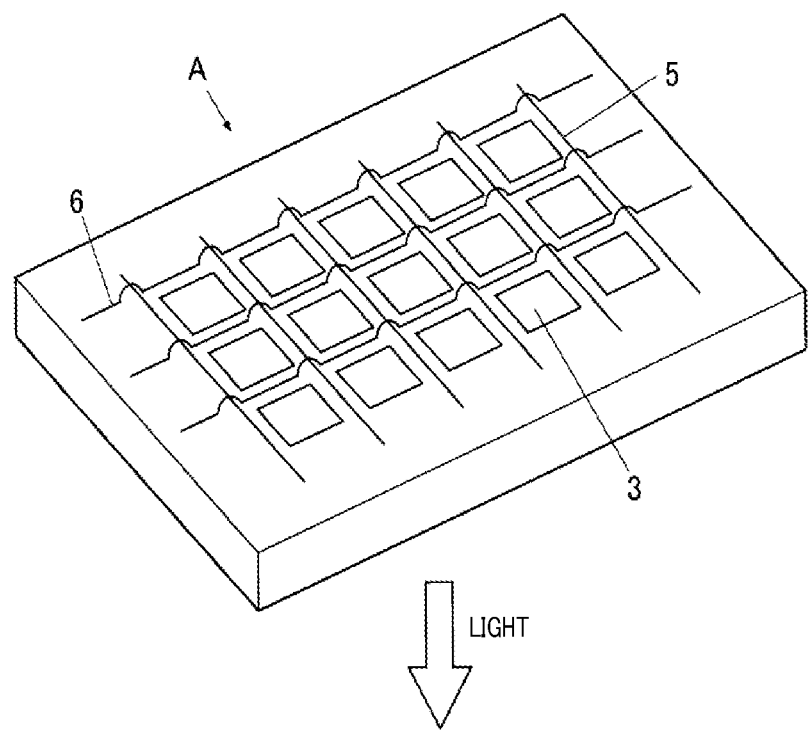
FIG. 6 is a schematic illustration of an active matrix display apparatus.

FIG. 6 is a schematic illustration of an active matrix display apparatus.

Display part A includes wiring portion C including a plurality of scanning lines 5 and data lines 6, and a plurality of pixels 3 on a substrate. The main members of display part A will be described hereinafter.

FIG. 6 illustrates a case in which light emitted from pixels 3 is extracted to the direction shown by the white arrow (downward direction).

Scanning lines 5 and plural data lines 6 in the wiring portion are each made of an electrically conductive material. Scanning lines 5 and data lines 6 intersect at right angles in a grid pattern and are connected to pixels 3 at the intersections (details are not shown).

When a scanning signal is applied from scanning line 5, pixels 3 receive an image data signal from data line 6 and emit light in response to the image data received.

Full color display can be achieved by appropriately disposing pixels that emit light in a red region, pixels that emit light in a green region, and pixels that emit light in a blue region in parallel on the same substrate.

Figure 7:
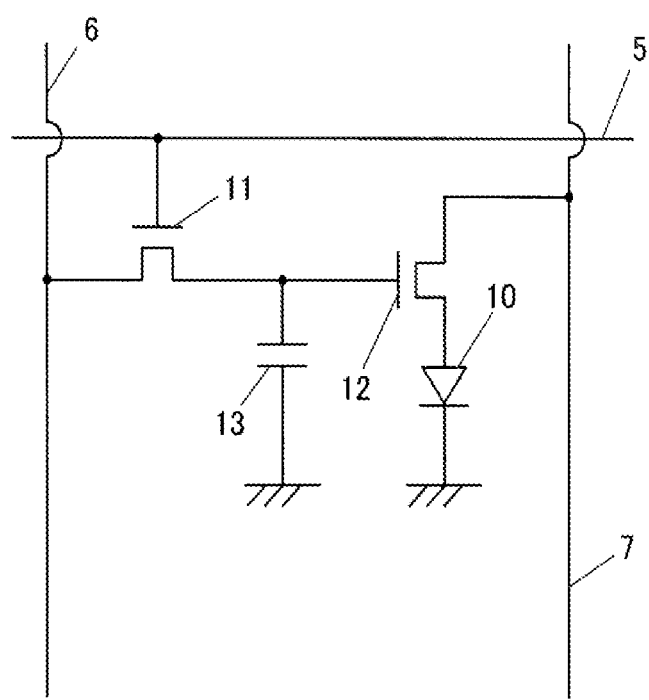
FIG. 7 is a schematic view of a pixel circuit.

Next, the light-emitting process by a pixel will now be described. FIG. 7 is a schematic illustration of a pixel circuit.

The pixel includes organic EL element 10, switching transistor 11, driving transistor 12, condenser 13 and the like. Full color display can be performed by using, as organic EL element 10 for plural pixels, organic EL elements emitting red light, green light, and blue light and disposing the elements in parallel on the same substrate.

In FIG. 7, an image data signal from control part B is applied to the drain of switching transistor 11 via data line 6. A scanning signal from control part B is then applied to the gate of switching transistor 11 via scanning line 5 to turn on driving of switching transistor 11, and the image data signal applied to the drain is transmitted to condenser 13 and gate of driving transistor 12.

Condenser 13 is charged through the transmission of the image data signal depending on the potential of the image data signal, and driving of driving transistor 12 is turned on. In driving transistor 12, the drain is connected to power source line 7 and a source is connected to the electrode of organic EL element 10 to supply a current to organic EL element 10 from power source line 7 depending on the potential of the image data signal applied to the gate.

The scanning signal is transmitted to next scanning line 5 by sequential scanning by control part B to turn off driving of switching transistor 11. However, condenser 13 maintains the charged potential of the image data signal even after the turning-off of driving of switching transistor 11, and thereby the driving state of driving transistor 12 is maintained to continue the light emission by organic EL element 10 until the next scanning signal is applied. Driving transistor 12 is driven in response to the potential of the subsequent image data signal in synchronization with the subsequent scanning signal applied by sequential scanning, resulting in light emission by organic EL element 10.

That is, light emission by organic EL element 10 is performed by providing switching transistor 11 and driving transistor 12 serving as active elements to organic EL element 10 of each of the plurality of pixels and allowing each of organic EL elements 10 of plural pixels 3 to emit light. Such a light emitting process is called an active matrix system.

Light emission from organic EL element 10 herein may have multiple gradations according to multi-valued image data signals having different gradation potentials, or a predetermined intensity of on-off light according to a binary image data signal. The electric potential of condenser 13 may be maintained until the subsequent scanning signal is applied, or may be discharged immediately before the subsequent scanning signal is applied.

In the present invention, the light emitting process is not limited to the active matrix system described above, and may be a passive matrix system, in which light is emitted from the organic EL element in response to the data signal only during scanning of the scanning signals.

Figure 8:
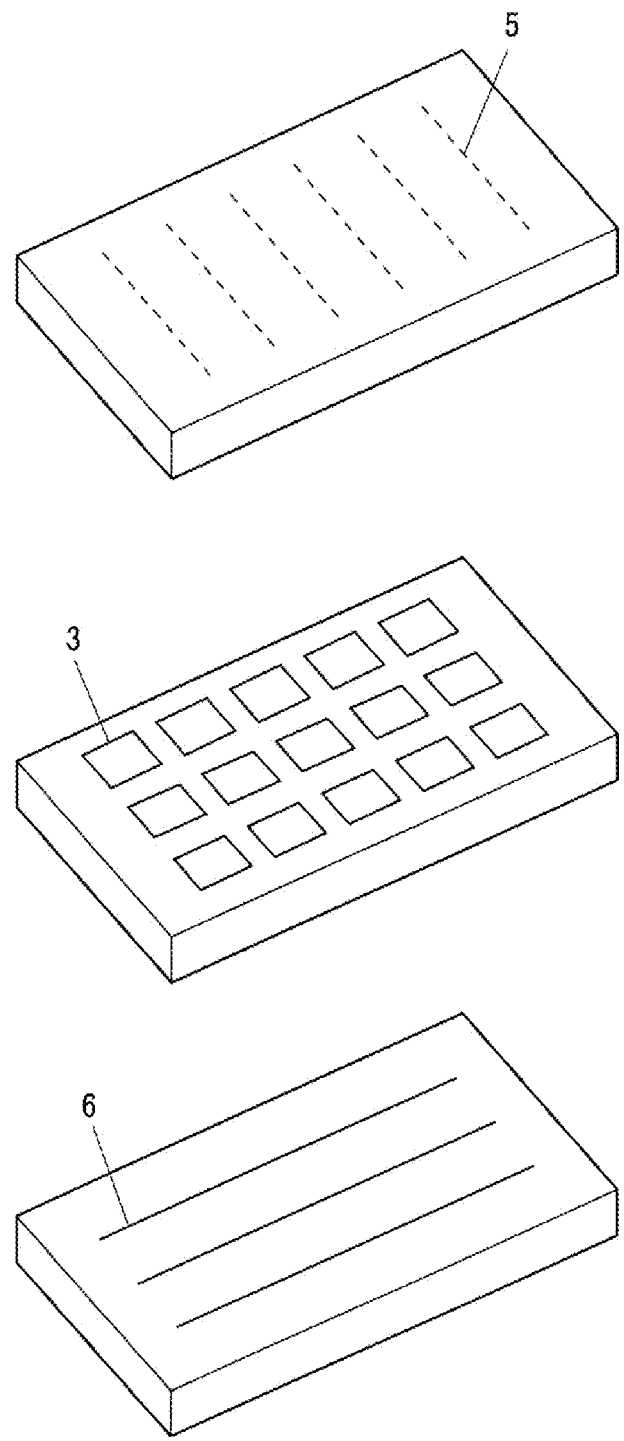
FIG. 8 is a schematic illustration of a passive matrix display apparatus.

FIG. 8 is a schematic illustration of a passive matrix display apparatus. In FIG. 8, a plurality of scanning lines 5 and a plurality of image data lines 6 are provided opposingly via pixels 3 in a grid pattern. When a scanning signal is applied to scanning line 5 by sequential scanning, pixel 3 connected to applied scanning line 5 emits light in response to the image data signal.

The passive matrix system does not have any active element in pixels 3, resulting in a reduction in manufacturing cost.

Use of the organic EL element of the present invention can provide a display apparatus having improved emission efficiency.

<Lighting Apparatus>

The organic EL element of the present invention can be used also for a lighting apparatus.

The organic EL element of the present invention may be used also as an organic EL element having a resonator configuration. The organic EL element having such a resonator configuration may be intended to be used for, but not limited to, a light source for an optical memory medium, light source for an electrophotographic copier, light source for an optical communication instrument, light source for an optical sensor or the like. Alternatively, the organic EL element may be used for the above-mentioned purposes by laser oscillation.

The organic EL element of the present invention may be used as a lamp such as a lighting source or an exposure light source or may be used as a projector for projecting images or a display apparatus (display) for direct view of still or moving images.

The driving system of the display apparatus used for playback of moving images may be either a passive matrix system or an active matrix system. Furthermore, a full-color display apparatus can be produced by employing two or more organic EL elements of the present invention that emit light of different colors.

The π-conjugated compound used for the present invention can be applied to a lighting apparatus including an organic EL element that emits substantially white light. For example, when a plurality of light-emitting materials are used, a plurality of emitted light colors are emitted simultaneously. Mixing the colors can provide white light emission. The combination of the emitted light colors may be a combination containing three maximum light emission wavelengths of three primary colors of blue, green, and red or a combination containing two maximum light emission wavelengths utilizing a relationship of complementary colors such as blue and yellow or bluish green and orange.

In the method of forming the organic EL element of the present invention, a mask is disposed only during formation of a light-emitting layer, hole transport layer, electron transport layer or the like. It is only required that the mask be simply disposed for separate coating by use of the mask, for example. Patterning with the mask or the like is not necessary because the other layers are common. A film, such as an electrode film, can be formed on the entire surface by a vapor deposition method, casting method, spin coating method, ink jetting method, printing method or the like. The productivity is thereby enhanced.

According to this method, the organic EL element itself emits white light, unlike a white light-emitting organic EL apparatus including an array of multiple light-emitting elements disposed in parallel.

[One Embodiment of Lighting Apparatus of Present Invention]

One embodiment of the lighting device including the organic EL element of the present invention will now be described.

The non-light emitting surface of the organic EL element of the present invention is covered with a glass case, and a glass substrate having a thickness of 300 μm is used as a sealing substrate. As a sealing material, an epoxy photocurable adhesive (LUXTRACK LC0629B manufactured by Toagosei Co., Ltd.) is applied to the periphery, and the product is placed onto the cathode and is attached to the transparent supporting substrate, followed by curing the adhesive by irradiation with UV light through the glass substrate for sealing. Accordingly, a lighting apparatus shown in FIGS. 9 and 10 can be formed.

Figure 9:
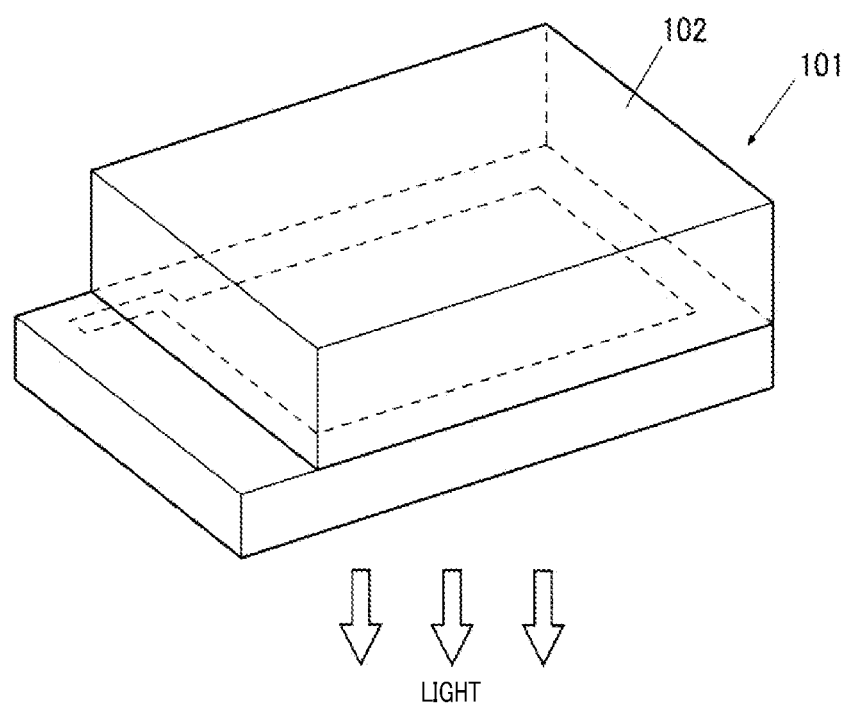
FIG. 9 is a schematic view of a lighting apparatus.

FIG. 9 is a schematic view of the lighting apparatus. The organic EL element of the present invention (organic EL element 101 in the lighting apparatus) is covered with glass cover 102 (sealing with the glass cover was performed in a glove box under a nitrogen atmosphere (an atmosphere of high purity nitrogen gas having a purity of at least 99.999%) to avoid contact of organic EL element 101 in the lighting apparatus with air).

Figure 10:
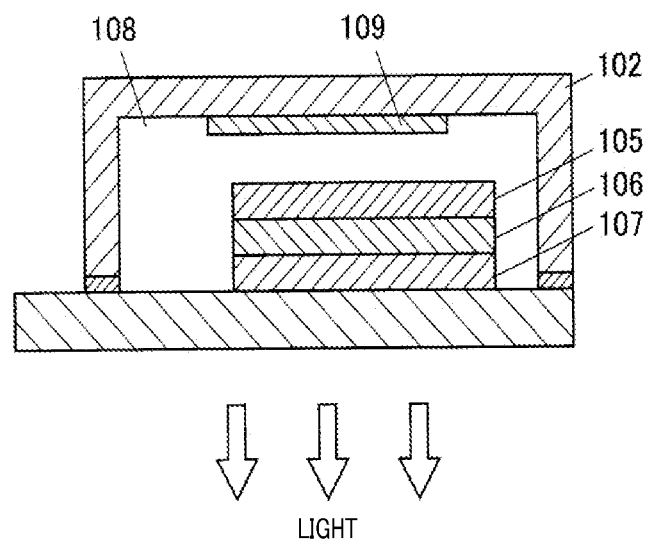
FIG. 10 is a schematic illustration of the lighting apparatus.

FIG. 10 is a cross-sectional view of the lighting apparatus, wherein 105 indicates a cathode, 106 indicates an organic layer, and 107 indicates a glass substrate provided with a transparent electrode. Meanwhile, the inside of glass cover 102 is filled with nitrogen gas 108 and is provided with water absorbent 109.

Use of the organic EL element of the present invention can provide a lighting apparatus having improved emission efficiency.

EXAMPLES

The present invention will now be described specifically by way of examples, but the present invention is not limited thereto. In Examples, the symbol "%" is used and meant by "mass %" unless otherwise stated.

Compounds used in Examples and Comparative Examples are shown below.

[Formula 24]
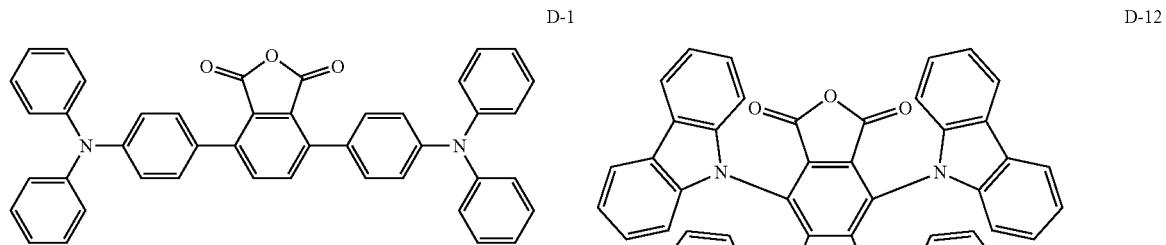
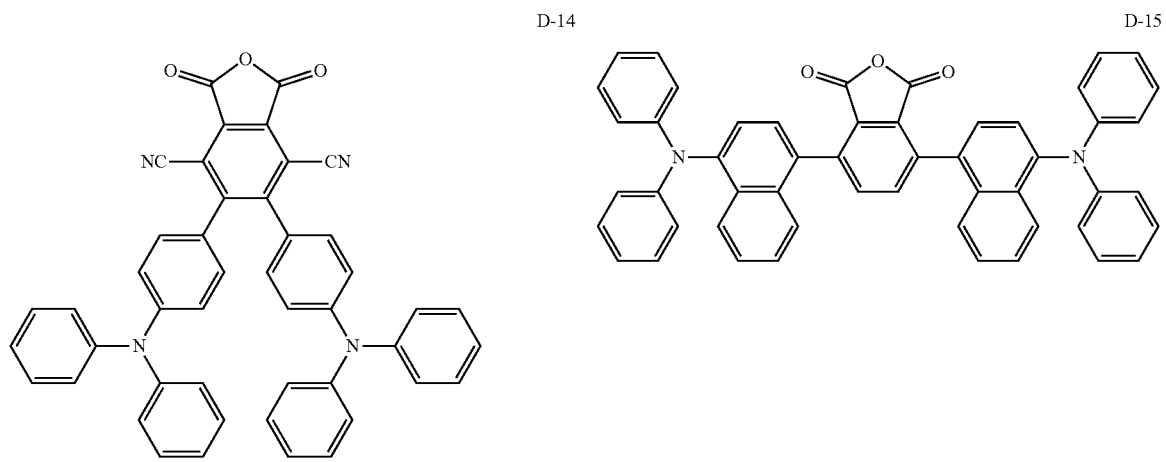
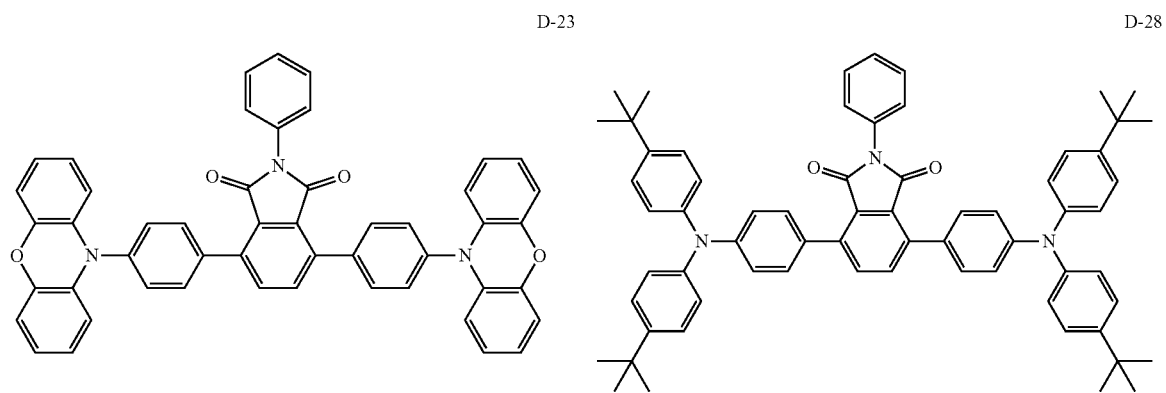 [SMILES: O=C1c2c(-c3ccc(N4c5ccccc5Oc5ccccc54)cc3)ccc(-c3ccc(N4c5ccccc5Oc5ccccc54)cc3)c2C(=O)N1c1ccccc1 ; CC(C)(C)c1ccc(N(c2ccc(-c3ccc(-c4ccc(N(c5ccc(C(C)(C)C)cc5)c5ccc(C(C)(C)C)cc5)cc4)c4c3C(=O)N(c3ccccc3)C4=O)cc2)c2ccc(C(C)(C)C)cc2)cc1]

-continued
D-29
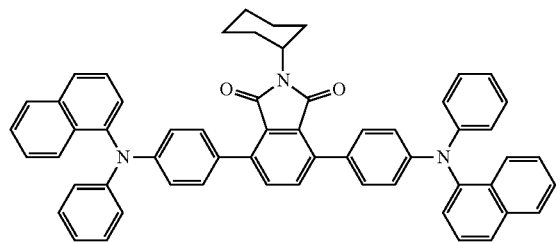
D-35
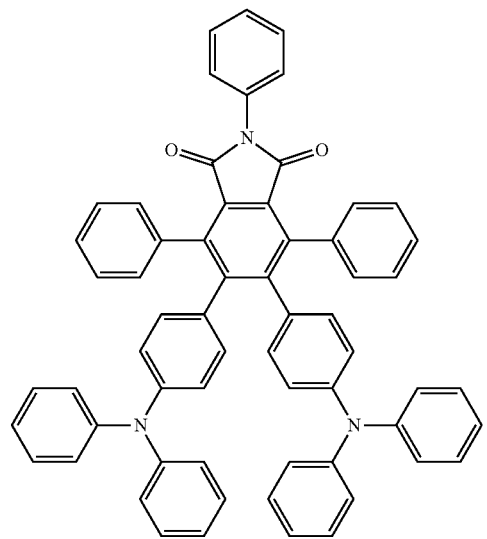
D-36
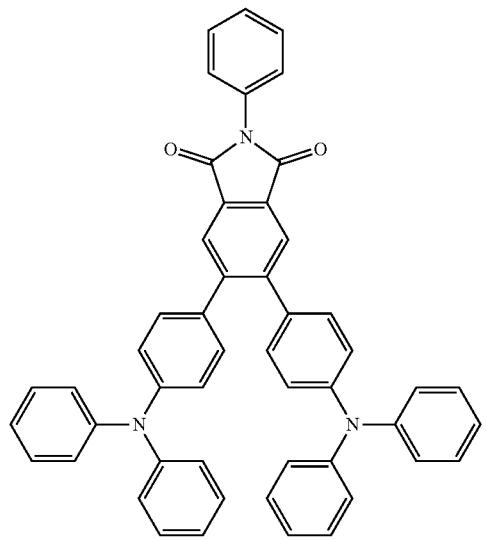
D-37
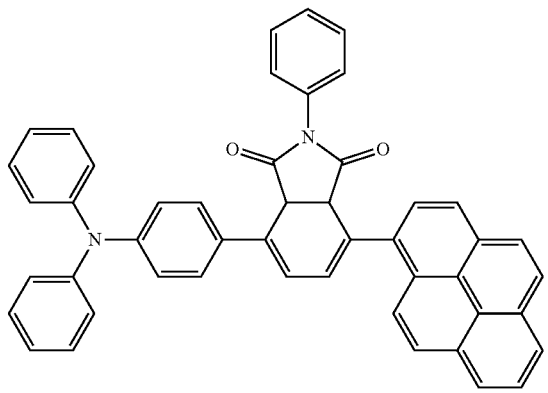
D-42
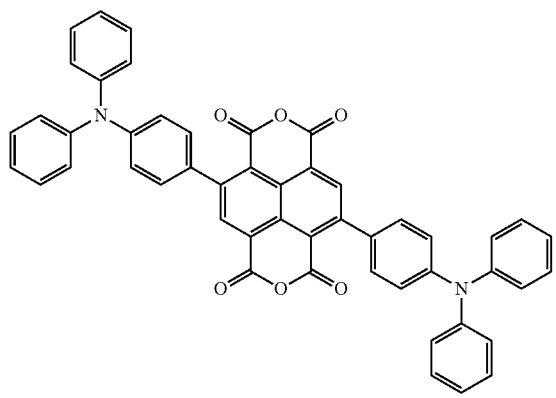
D-43
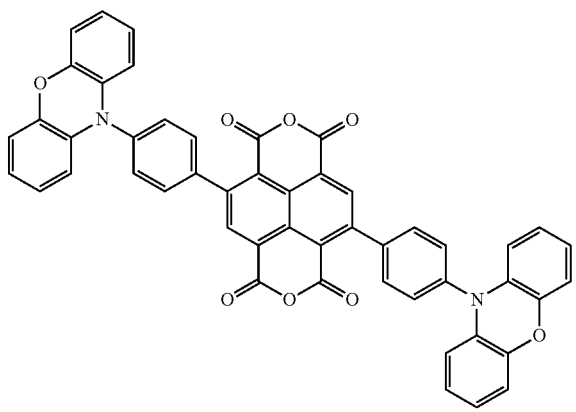

-continued
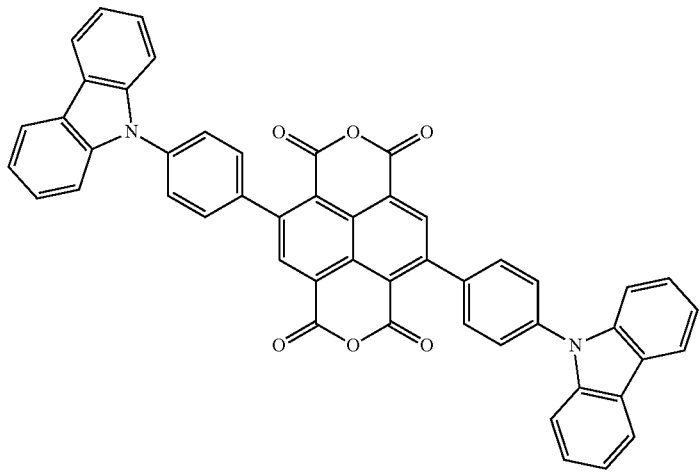
D-45
[Formula 25]
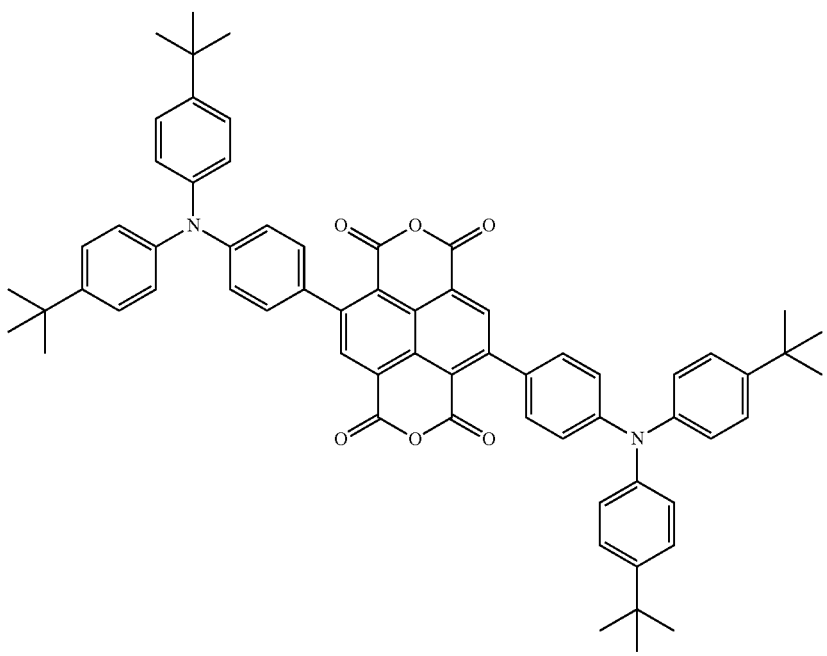
D-47
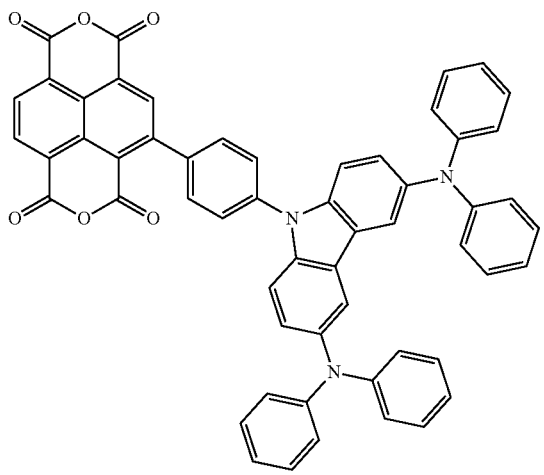
D-51
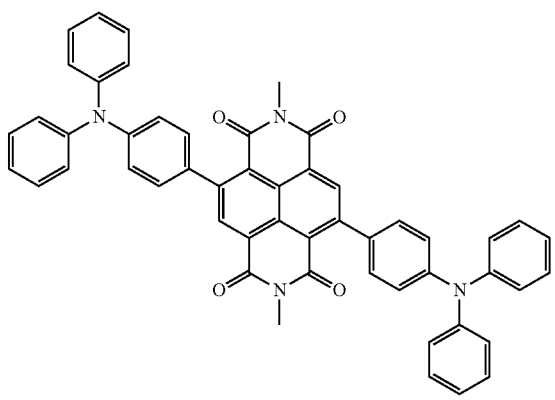
D-56

-continued
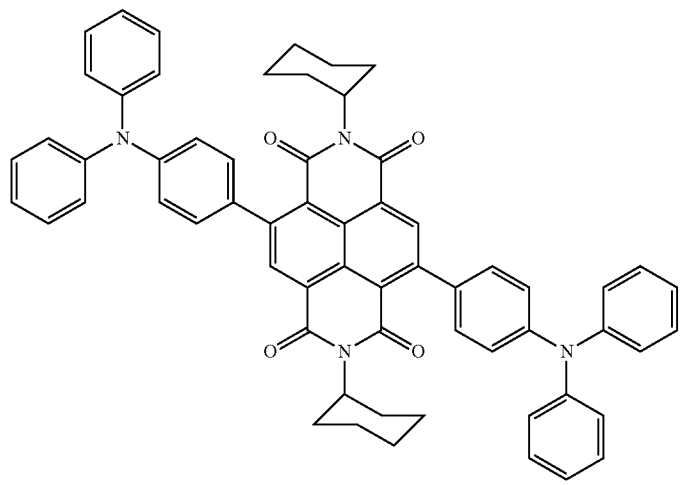
D-59
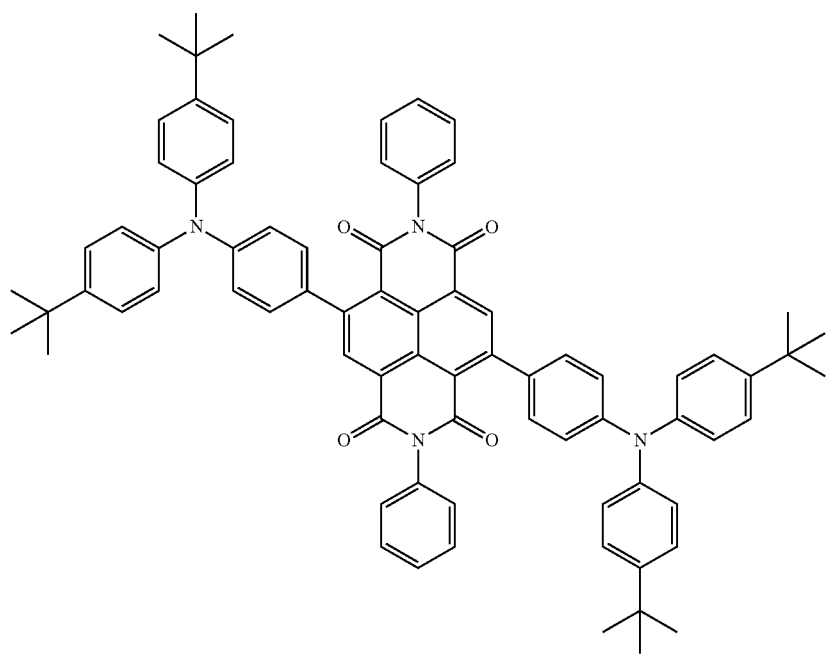
D-61

-continued
D-63
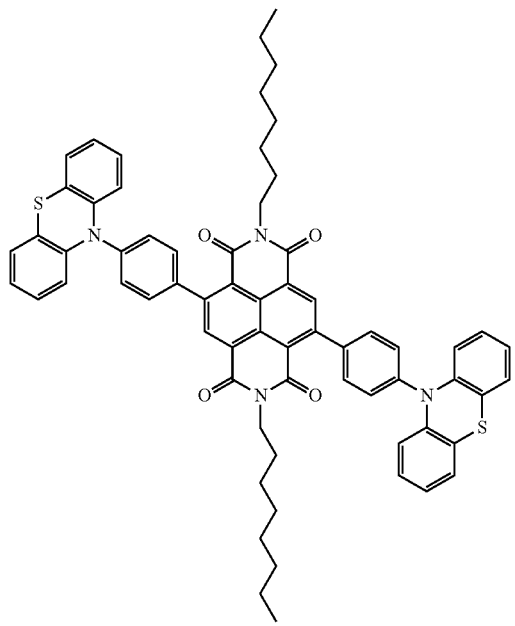
D-76
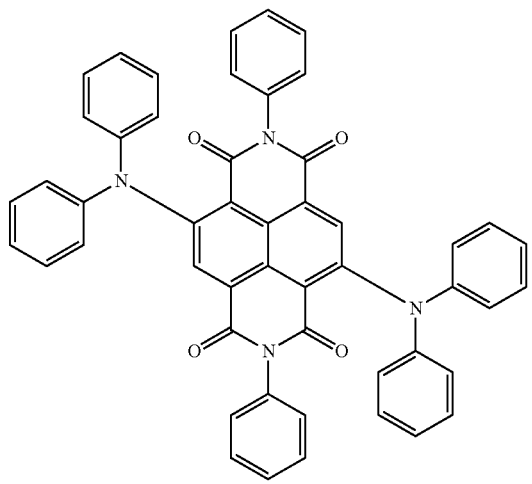
D-77
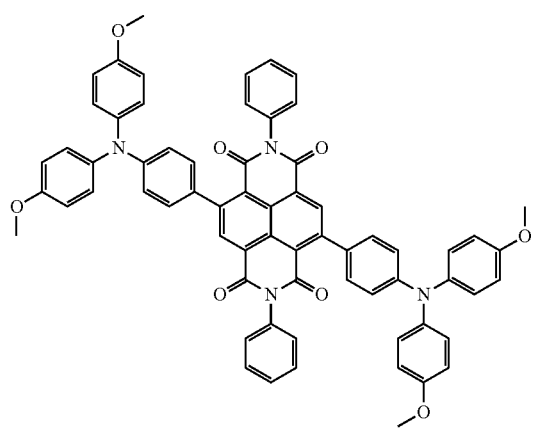
D-78
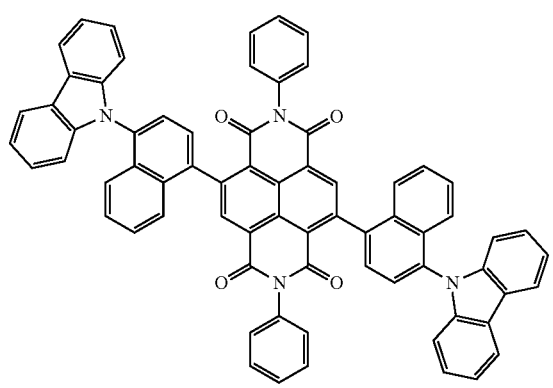
[Formula 26]
D-80
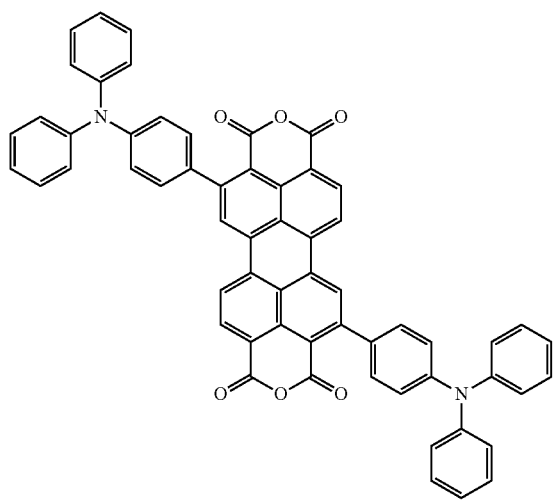
D-83
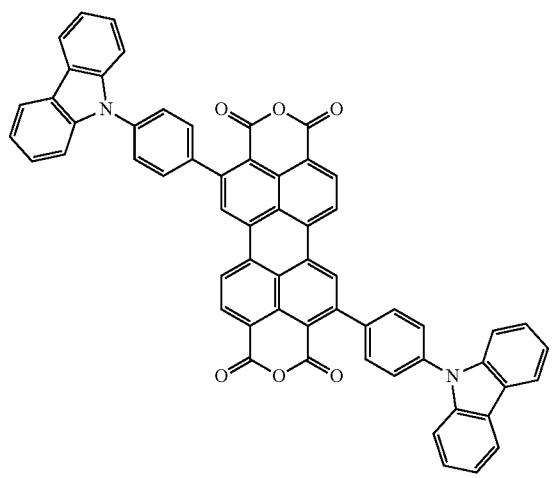

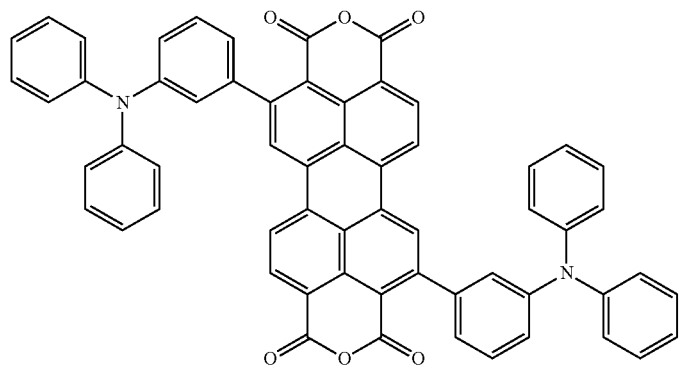
D-90
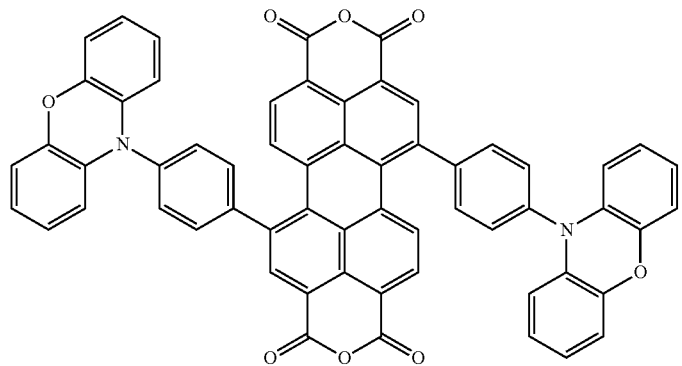
D-93
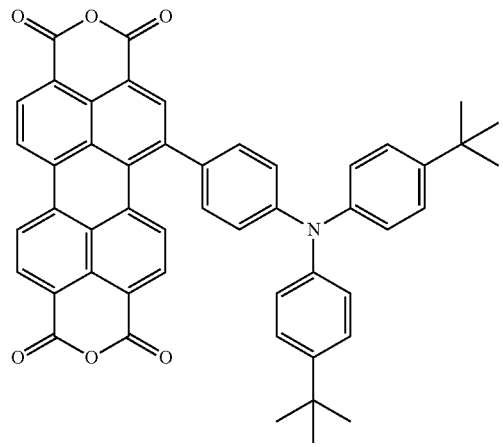
D-97
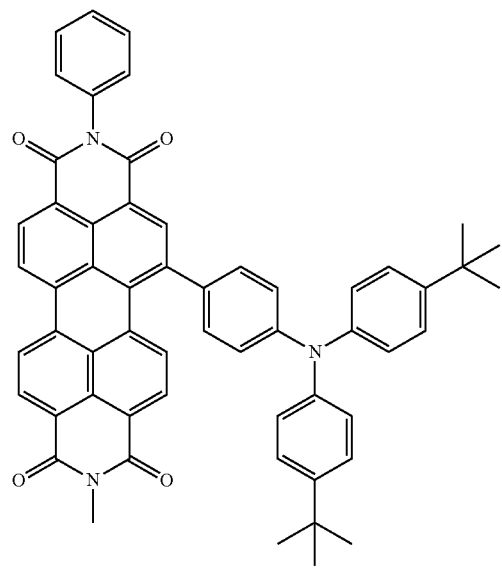
D-104

-continued
D-106
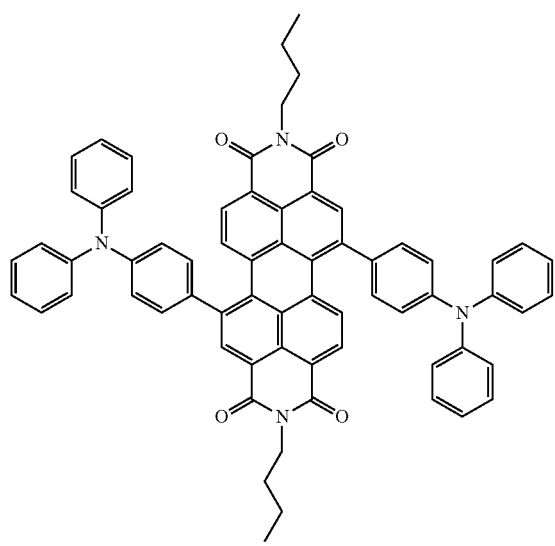
D-111
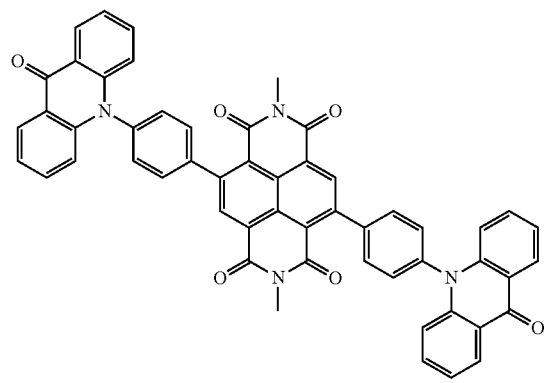
D-112
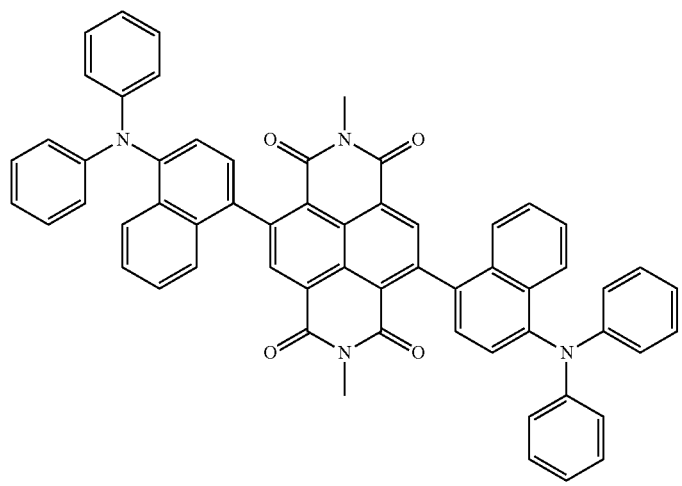

[Formula 27]
Comparative compound 1
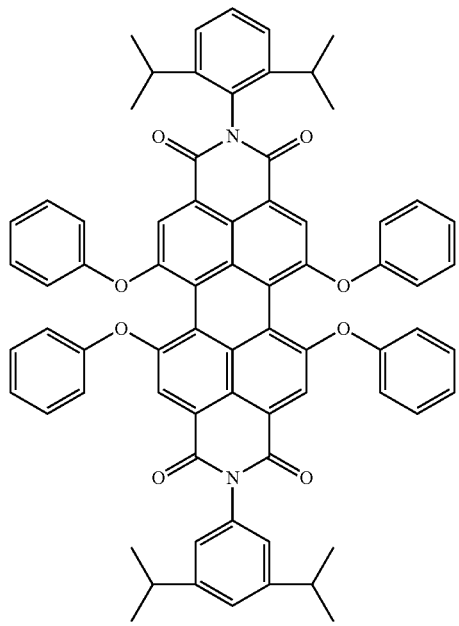
Comparative compound 2
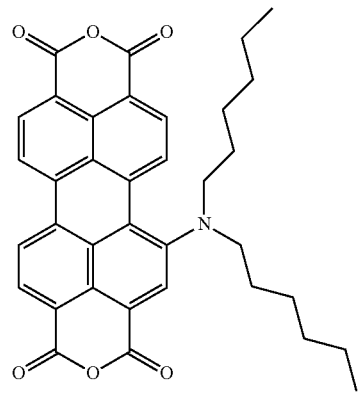
Comparative compound 3
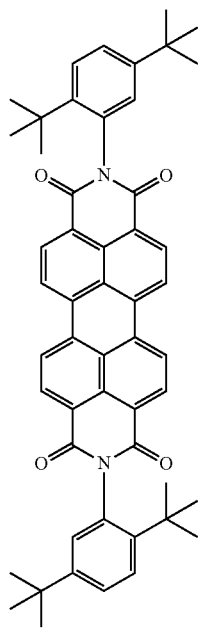
Comparative compound 4
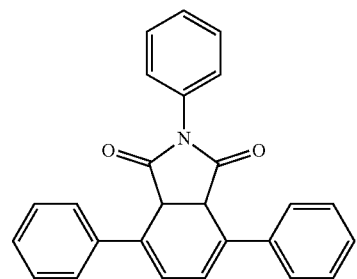

-continued

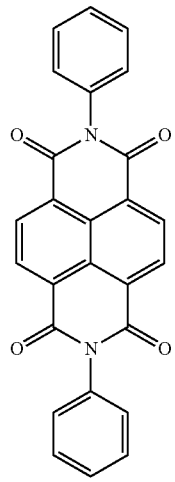
Comparative compound 5

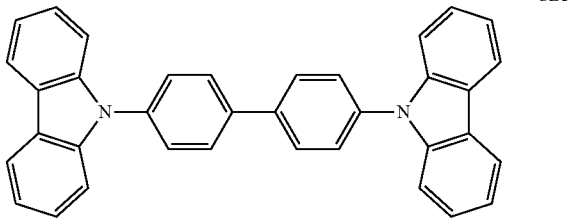
CBP

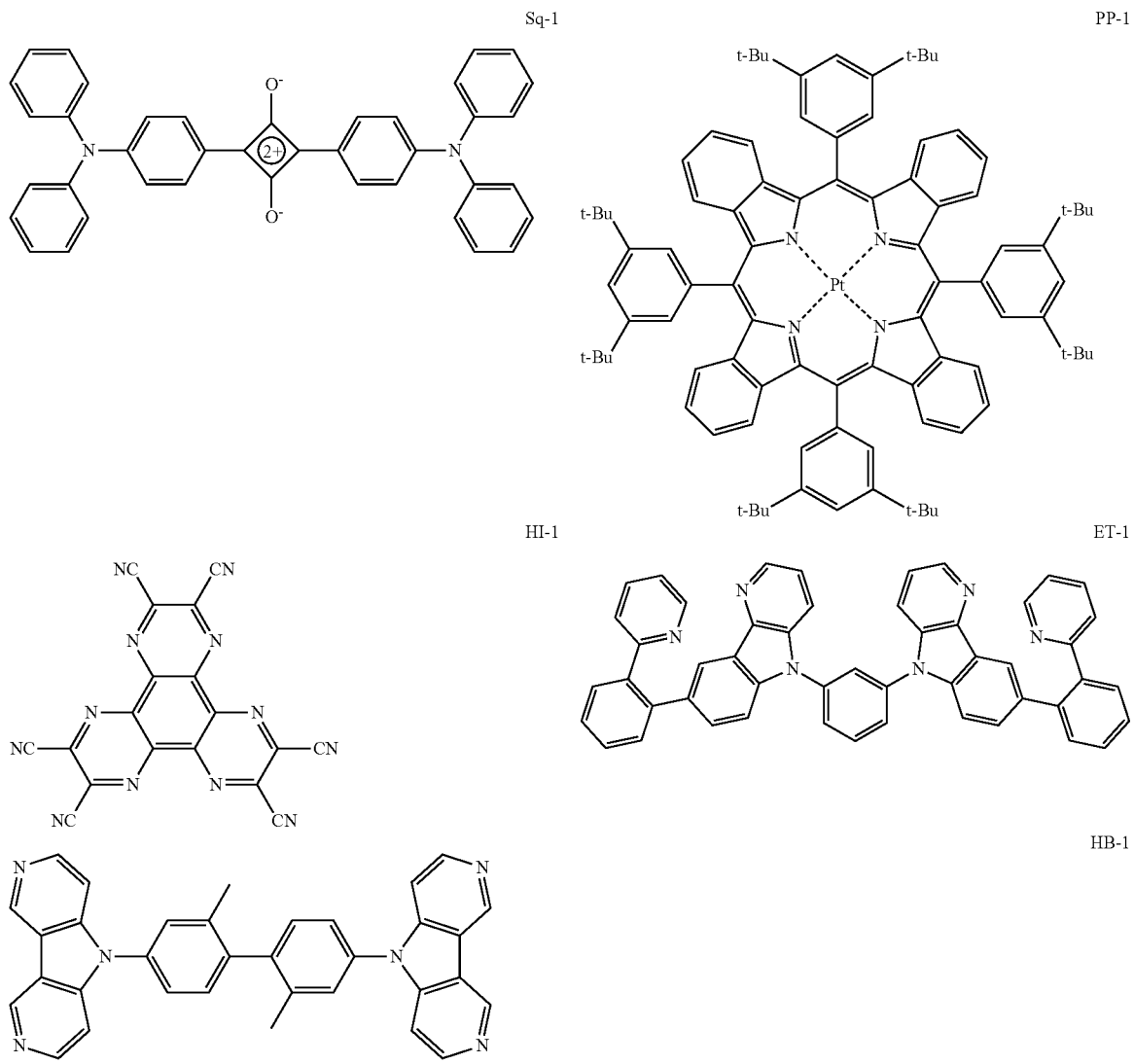

(Synthesis of Compound D-56)

Compound D-56 was synthesized by using the method described in J. Am. Chem. Soc. 2009, 131, 8-9., Angew. Chem. Int. Ed. 2005, 44, 4442-4489. Specifically, bromination reaction of naphthalene carboxylic dianhydride (compound 1) was performed as shown in the following chemical formula to obtain a dibromonaphthalene tetracarboxylic dianhydride intermediate (compound 2). Then, imidation reaction of the dibromonaphthalene tetracarboxylic dianhydride intermediate (compound 2) was performed to obtain a dibromonaphthalene tetracarboxylic diimide intermediate (compound 3). Subsequently, the dibromonaphthalene tetracarboxylic diimide intermediate (compound 3) was allowed to react with 4-(diphenylamino) phenylboronic acid in the presence of a palladium catalyst to obtain a crude product of compound D-56. Thereafter, column chromatography, recrystallization, and sublimation purification were performed to obtain a highly pure product of compound D-56.

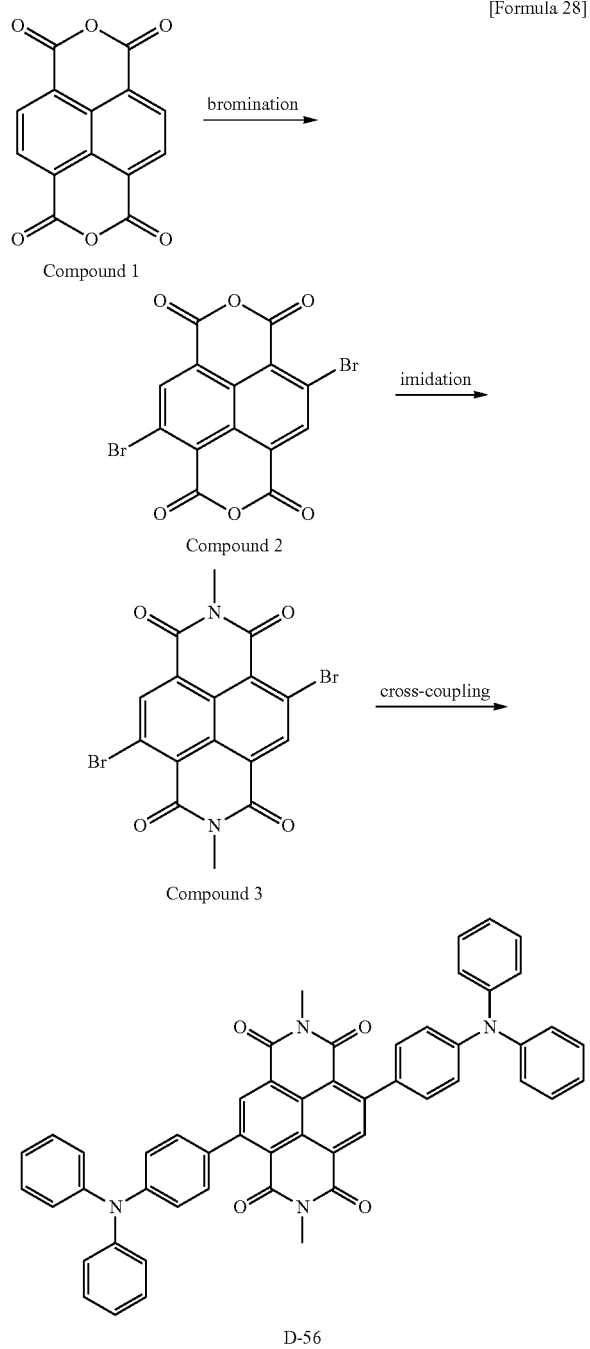

[Formula 28]

Compound 1 → bromination → Compound 2 → imidation → Compound 3 → cross-coupling → D-56

(Synthesis of Other Compounds)

Compounds D-1, D-12, D-14, D-15, D-23, D-28, D-29, D-35, D-36, D-37, D-42, D-43, D-45, D-47, D-51, D-56, D-59, D-61, D-63, D-76, D-77, D-78, D-80, D-83, D-90, D-93, D-97, D-104, D-106, D-111, and D-112 were synthesized in the same manner as the production method of compound D-56 mentioned above. $\Delta E_{ST}$ of each of the obtained compounds and comparative compounds 1 to 5 was determined by calculation by the following method.

(Calculation of $\Delta E_{ST}$)

The structure optimization and calculation of the electron density distribution by molecular orbital calculation of the compounds can be carried out by using, as a calculation technique, software for molecular orbital calculation including B3LYP as a functional and 6-31G (d) as a basis function. As the software for molecular orbital calculation, Gaussian 09 (Revision C.01, M. J. Frisch, et al, Gaussian, Inc., 2010.) manufactured by Gaussian Co. (USA) was used.

From the structure optimization calculation including B3LYP as the functional and 6-31G (d) as the basis function, excited state calculation by means of the time-dependent density functional theory (Time-Dependent DFT) was further carried out to determine energy levels of S1 and T1, (E(S1) and E(T1), respectively), and thus, the state was calculated as $\Delta E_{ST}=|E(S1)-E(T1)|$.

[Example 1]

(Production of Organic EL Element 1-1)

Onto a glass substrate having a size of 50 mm×50 mm×a thickness of 0.7 mm, indium tin oxide (ITO) was deposited as an anode into a thickness of 150 nm, and the substrate obtained was subjected to patterning. Thereafter, the transparent substrate provided with this ITO transparent electrode was ultrasonic cleaned in isopropyl alcohol, was dried with dry nitrogen gas, and was cleaned with UV ozone for 5 minutes. This transparent substrate was then fixed to a substrate holder of a commercially available vacuum evaporation apparatus.

Materials for individual layers, in optimum amounts for producing an element, were placed into individual crucibles for vacuum evaporation in the vacuum evaporation apparatus. The crucibles for vacuum evaporation used were composed of a material for resistance heating, such as molybdenum or tungsten.

After evacuation to a degree of vacuum of 1×10⁻⁴ Pa, a crucible for vacuum evaporation containing 1,4,5,8,9,12-hexaazatriphenylene hexacarbonitrile (HAT-CN) was energized and heated to deposit HAT-CN onto the ITO transparent electrode at a deposition rate of 0.1 nm/s, thereby forming a hole injection layer having a thickness of 10 nm.

Subsequently, 4,4'-bis[N-(1-naphthyl)-N-phenylamino]biphenyl (α-NPD) was deposited on the hole injection layer at a deposition rate of 0.1 nm/s, thereby forming a hole transport layer having a thickness of 40 nm. Then, a host compound (CBP) and a luminescent compound (comparative compound 1) were co-deposited at a deposition rate of 0.1 nm/s so as to achieve 99 vol % and 1 vol %, respectively, thereby forming a light-emitting layer having a thickness of 30 nm.

Thereafter, 2,9-dimethyl-4,7-diphenyl-1,10-phenanthroline (BCP) was deposited at a deposition rate of 0.1 nm/s, thereby forming an electron transport layer having a thickness of 30 nm.

Additionally, lithium fluoride was deposited into a thickness of 0.5 nm, and then aluminum was further deposited to 100 nm thereon, thereby forming a cathode.

The non-light emitting surface side of the above element was covered with a can-shaped glass case under an atmosphere of high purity nitrogen gas having a purity of at least 99.999% and electrode extraction wiring was installed thereto, thereby producing organic EL element 1-1.

(Production of Organic EL Elements 1-2 to 1-36)

Organic EL elements 1-2 to 1-36 were produced in the same manner as organic EL element 1-1 except that comparative compound 1 as the luminescent compound was changed as shown in Table 1.

TABLE 1

| Organic EL element | Luminescent compound | $\Delta E_{ST}$ (eV) | Relative emission efficiency (%) | Half lifetime (%) | Remarks |
|---|---|---|---|---|---|
| 1-1 | Comparative compound 1 | 0.95 | 100 | 100 | Comparative example |
| 1-2 | Comparative compound 2 | 0.88 | 87 | 85 | Comparative example |
| 1-3 | Comparative compound 3 | 1.16 | 99 | 96 | Comparative example |
| 1-4 | Comparative compound 4 | 0.48 | 43 | 32 | Comparative example |
| 1-5 | Comparative compound 5 | 1.06 | 79 | 82 | Comparative example |
| 1-6 | D-1 | 0.19 | 130 | 132 | Present invention |
| 1-7 | D-12 | 0.11 | 129 | 126 | Present invention |
| 1-8 | D-14 | 0.13 | 121 | 124 | Present invention |
| 1-9 | D-15 | 0.13 | 120 | 118 | Present invention |
| 1-10 | D-23 | 0.00 | 138 | 141 | Present invention |
| 1-11 | D-28 | 0.16 | 142 | 138 | Present invention |
| 1-12 | D-29 | 0.18 | 141 | 131 | Present invention |
| 1-13 | D-35 | 0.10 | 135 | 130 | Present invention |
| 1-14 | D-36 | 0.23 | 132 | 130 | Present invention |
| 1-15 | D-37 | 0.40 | 119 | 115 | Present invention |
| 1-16 | D-42 | 0.36 | 148 | 134 | Present invention |
| 1-17 | D-43 | 0.03 | 132 | 135 | Present invention |
| 1-18 | D-45 | 0.08 | 150 | 148 | Present invention |
| 1-19 | D-47 | 0.23 | 146 | 134 | Present invention |
| 1-20 | D-51 | 0.09 | 142 | 133 | Present invention |
| 1-21 | D-56 | 0.18 | 175 | 142 | Present invention |
| 1-22 | D-59 | 0.16 | 176 | 155 | Present invention |
| 1-23 | D-61 | 0.17 | 182 | 156 | Present invention |
| 1-24 | D-63 | 0.00 | 162 | 148 | Present invention |
| 1-25 | D-76 | 0.51 | 119 | 110 | Present invention |
| 1-26 | D-77 | 0.19 | 145 | 129 | Present invention |
| 1-27 | D-78 | 0.00 | 120 | 127 | Present invention |
| 1-28 | D-80 | 0.36 | 160 | 124 | Present invention |
| 1-29 | D-83 | 0.07 | 150 | 136 | Present invention |
| 1-30 | D-90 | 0.01 | 152 | 131 | Present invention |
| 1-31 | D-93 | 0.01 | 152 | 140 | Present invention |
| 1-32 | D-97 | 0.24 | 132 | 128 | Present invention |
| 1-33 | D-104 | 0.32 | 135 | 129 | Present invention |
| 1-34 | D-106 | 0.45 | 140 | 130 | Present invention |
| 1-35 | D-111 | 0.00 | 115 | 115 | Present invention |
| 1-36 | D-112 | 0.02 | 134 | 126 | Present invention |

[Evaluation]

The emission efficiency and half lifetime of the organic EL elements each produced in Examples and Comparative Examples were measured by the following methods.

(Measurement of Relative Emission Efficiency)

The emission efficiency of each sample during operation of the organic EL element was evaluated by performing the following measurement. Each organic EL element produced as described above was allowed to emit light with a constant electric current of 2.5 mA/cm² at room temperature (about 25° C.). The emission luminance immediately after the light emission started was measured by using a spectroradiometer CS-2000 (manufactured by Konica Minolta, Inc.).

The emission efficiency obtained (relative values to the emission luminance of organic EL element 1-1) is shown in Table 1.

(Evaluation of Half Lifetime)

The half lifetime of each sample during operation of the organic EL element was evaluated by performing the following measurement. While each sample was continuously operated at an initial luminance of 1,000 cd/m², the luminance was measured by using the spectroradiometer CS-2000 to determine the time period until the luminance decreased by half (LT50). The relative LT50 values obtained (relative values to LT50 of organic EL element 1-1) are shown in Table 1.

(Results)

As shown in Table 1, the organic EL elements in which a π-conjugated compound having the structure represented by any of the general formulas 1 to 3 mentioned above was used as the luminescent compound exhibited emission efficiency higher than that of the organic EL elements in which the comparative compound was used as the luminescent compound. The organic EL elements of Examples also had an increase in the lifetime. Additionally, the elements containing the π-conjugated compound each had a decrease in the $\Delta E_{ST}$ value, compared with those each containing a comparative compound having a similar skeleton.

In comparing a case where only one group represented by general formula 4 was bonded (organic EL element 1-15) with a case where two groups represented by general formula 4 were bonded (e.g., organic EL element 1-6) herein, the case where two groups represented by general formula 4 were bonded had smaller $\Delta E_{ST}$, and additionally had satisfactory relative emission efficiency and a longer half lifetime.

In comparing a case where L in general formula 4 was a phenylene group (e.g., organic EL element 1-6) with a case where L was a naphthalenylene group (e.g., organic EL element 1-9), the case where L was a phenylene group had higher relative emission efficiency and also had a longer half lifetime. It is conceived that this is because the planarity of the molecule of the π-conjugated compound has enhanced.

[Example 2]

(Production of Organic EL Element 2-1)

A substrate obtained by depositing indium tin oxide (ITO) as an anode into 100 nm on a glass substrate having a size of 100 mm×100 mm×1.1 mm (manufactured by NH Techno Glass Corporation, NA45) was subjected to patterning. Thereafter, the transparent supporting substrate provided with this ITO transparent electrode was ultrasonic cleaned in isopropyl alcohol, was dried with dry nitrogen gas, and was cleaned with UV ozone for 5 minutes.

On this transparent supporting substrate, a thin film was formed by the spin coating method by using a solution of poly(3,4-ethylenedioxythiophene)-polystyrenesulfonate (PEDOT/PSS, manufactured by Bayer AG, Baytron P Al 4083) diluted with pure water to 70% under conditions of 3,000 rpm and 30 seconds. Then, the thin film was dried at 200° C. for an hour, providing a hole injection layer having a thickness of 20 nm. This transparent substrate was then fixed to a substrate holder of a commercially available vacuum evaporation apparatus. Materials for individual layers, in optimum amounts for producing an element, were placed into individual crucibles for vacuum evaporation in the vacuum evaporation apparatus. The crucibles for vacuum evaporation used were composed of a material for resistance heating, such as molybdenum or tungsten.

After evacuation to a degree of vacuum of 1×10⁻⁴ Pa, α-NPD was deposited on the hole injection layer at a deposition rate of 0.1 nm/s, thereby forming a hole transport layer having a thickness of 40 nm. Then, a host compound (CBP) and a luminescent compound (Sq-1) were co-deposited at a deposition rate of 0.1 nm/s so as to achieve 99 vol % and 1 vol %, respectively, thereby forming a light-emitting layer having a thickness of 30 nm.

Thereafter, 1,3,5-tris(N-phenylbenzimidazol-2-yl) benzene (TPBi) was deposited at a deposition rate of 0.1 nm/s, thereby forming an electron transport layer having a thickness of 30 nm.

Additionally, sodium fluoride was deposited into a thickness of 1 nm, and then aluminum was further deposited to 100 nm thereon, thereby forming a cathode.

The non-light emitting surface side of the above element was covered with a can-shaped glass case under an atmosphere of high purity nitrogen gas having a purity of at least 99.999% and electrode extraction wiring was installed thereto, thereby producing organic EL element 2-1.

(Production of Organic EL Element 2-2)

A light-emitting layer was formed such that the content of a host compound (CBP), a luminescent compound (Sq-1), and a third component (assist dopant: comparative compound 1) were 89 vol %, 1 vol %, and 10 vol %, respectively. Organic EL element 2-2 was produced in the same manner as organic EL element 2-1 except for the light-emitting layer.

(Production of Organic EL Elements 2-3 to 2-13)

Organic EL elements 2-3 to 2-13 were produced in the same manner as organic EL element 2-2 except that the third component (assist dopant) was changed as shown in Table 2.

TABLE 2

| Organic EL element | Third component | $\Delta E_{ST}$ (eV) | Relative emission efficiency (%) | Half lifetime (%) | Remarks |
|---|---|---|---|---|---|
| 2-1 | None | — | 100 | 100 | Comparative example |
| 2-2 | Comparative compound 1 | 0.95 | 83 | 92 | Comparative example |
| 2-3 | Comparative compound 2 | 0.87 | 86 | 81 | Comparative example |
| 2-4 | Comparative compound 3 | 1.16 | 71 | 98 | Comparative example |
| 2-5 | Comparative compound 4 | 0.48 | 79 | 82 | Comparative example |
| 2-6 | Comparative compound 5 | 1.06 | 81 | 85 | Comparative example |
| 2-7 | D-14 | 0.13 | 141 | 136 | Present invention |
| 2-8 | D-23 | 0.00 | 129 | 133 | Present invention |
| 2-9 | D-47 | 0.23 | 150 | 157 | Present invention |
| 2-10 | D-59 | 0.16 | 155 | 144 | Present invention |
| 2-11 | D-76 | 0.51 | 118 | 114 | Present invention |
| 2-12 | D-78 | 0.00 | 128 | 116 | Present invention |
| 2-13 | D-106 | 0.45 | 125 | 127 | Present invention |

[Evaluation]

The emission efficiency and half lifetime of the organic EL elements each produced in Examples and Comparative Examples were measured in the same manner as in Example 1. The emission efficiency obtained (relative values to the emission luminance of organic EL element 2-1) is shown in Table 2. Additionally, the relative LT50 values obtained (relative values to LT50 of organic EL element 2-1) are shown.

(Results)

As shown in Table 2, the organic EL elements in which a π-conjugated compound having the structure represented by any of the general formulas 1 to 3 mentioned above was used as the assist dopant exhibited emission efficiency higher than that of the organic EL elements in which the comparative compound was used as the assist dopant and the organic EL element containing no assist dopant. The organic EL elements of Examples also had an increase in the lifetime.

[Example 3]

(Production of Organic EL Element 3-1)

Onto a glass substrate having a size of 50 mm×50 mm×a thickness of 0.7 mm, indium tin oxide (ITO) was deposited as an anode into a thickness of 150 nm, and the substrate obtained was subjected to patterning. Thereafter, the transparent substrate provided with this ITO transparent electrode was ultrasonic cleaned in isopropyl alcohol, was dried with dry nitrogen gas, and was cleaned with UV ozone for 5 minutes. This transparent substrate was then fixed to a substrate holder of a commercially available vacuum evaporation apparatus.

Materials for individual layers, in optimum amounts for producing an element, were placed into individual resistive-heating boats for vacuum evaporation in the vacuum evaporation apparatus. The resistive-heating boats used were composed of molybdenum or tungsten.

After evacuation to a degree of vacuum of $1\times10^{-4}$ Pa, a resistive-heating boat containing HI-1 was energized and heated to deposit HI-1 onto the ITO transparent electrode at a deposition rate of 0.1 nm/s, thereby forming a hole injection layer having a thickness of 15 nm.

Subsequently, 4,4'-bis[N-(1-naphthyl)-N-phenylamino]biphenyl (α-NPD), was deposited thereon at a deposition rate of 0.1 nm/s, thereby forming a hole transport layer having a thickness of 30 nm.

Then, resistive-heating boats each containing a host compound (comparative compound 1) and a luminescent compound (PP-1) were energized and heated to co-deposit comparative compound 1 at a deposition rate of 0.1 nm/s and PP-1 at a deposition rate of 0.010 nm/s onto the hole transport layer, thereby forming a light-emitting layer having a thickness of 40 nm.

Then, HB-1 was deposited thereon at a deposition rate of 0.1 nm/s, thereby forming a first electron transport layer having a thickness of 5 nm. Additionally, thereon, ET-1 was deposited thereon at a deposition rate of 0.1 nm/s, thereby forming a second electron transport layer having a thickness of 45 nm. Thereafter, lithium fluoride was deposited into a thickness of 0.5 nm, and then aluminum was further deposited to 100 nm thereon to form a cathode, thereby producing organic EL element 3-1.

(Production of Organic EL Elements 3-2 to 3-10)

Organic EL elements 3-2 to 3-10 were produced in the same manner as organic EL element 3-1 except that comparative compound 1 as the host compound was changed as shown in Table 3.

TABLE 3

| Organic EL element | Host compound | $\Delta E_{ST}$ (eV) | Relative emission efficiency (%) | Half lifetime (%) | Remarks |
|---|---|---|---|---|---|
| 3-1 | Comparative compound 1 | 0.95 | 100 | 100 | Comparative example |
| 3-2 | Comparative compound 2 | 0.87 | 113 | 76 | Comparative example |
| 3-3 | Comparative compound 3 | 1.16 | 66 | 72 | Comparative example |
| 3-4 | Comparative compound 4 | 0.46 | 106 | 90 | Comparative example |
| 3-5 | Comparative compound 5 | 1.06 | 116 | 78 | Comparative example |
| 3-6 | D-14 | 0.13 | 126 | 116 | Present invention |
| 3-7 | D-23 | 0.00 | 129 | 127 | Present invention |

TABLE 3-continued

| Organic EL element | Host compound | $\Delta E_{ST}$ (eV) | Relative emission efficiency (%) | Half lifetime (%) | Remarks |
|---|---|---|---|---|---|
| 3-8 | D-47 | 0.23 | 138 | 124 | Present invention |
| 3-9 | D-59 | 0.16 | 134 | 141 | Present invention |
| 3-10 | D-78 | 0.00 | 122 | 115 | Present invention |

[Evaluation]

The emission efficiency and half lifetime of the organic EL elements each produced in Examples and Comparative Examples were measured in the same manner as in Example 1. The emission efficiency obtained (relative values to the emission luminance of organic EL element 3-1) is shown in Table 3. Additionally, the relative LT50 values obtained (relative values to LT50 of organic EL element 3-1) are shown.

(Results)

As shown in Table 3, the organic EL elements in which the π-conjugated compound having the structure represented by any of general formulas 1 to 3 mentioned above was used as the host compound exhibited emission efficiency higher than that of the organic EL elements in which the comparative compound was used as the host compound. The organic EL elements of Examples also had an increase in the lifetime.

This application claims the benefit of Japanese Patent Application No. 2016-135999 filed on Jul. 8, 2016, the disclosure of which including the specification and drawings is incorporated herein by reference in its entirety.

INDUSTRIAL APPLICABILITY

According to the above aspects of the present invention, a novel organic EL element of which emission efficiency and lifetime, for example, have been improved can be provided. A display apparatus and a lighting apparatus including the organic EL element can be provided. A light-emitting material having excellent emission characteristics also can be provided.

REFERENCE SIGNS LIST

1 Display
3 Pixel
5 Scanning line
6 Data lines
7 Power source line
10 Organic EL element
11 Switching transistor
12 Driving transistor
13 Condenser
101 Organic EL element in lighting apparatus
102 Glass cover
105 Cathode
106 Organic layer
107 Glass substrate provided with transparent electrode
108 Nitrogen gas
109 Water absorbent
A Display part
B Control part
C Wiring portion

The invention claimed is:

1. An organic electroluminescent element comprising an anode, a cathode, and an organic layer including a light-emitting layer sandwiched between the anode and the cathode, wherein the light-emitting layer comprises:
   at least one luminescent compound selected from a fluorescence-emitting compound;
   a host; and
   an assist dopant, wherein the assist dopant is selected from π-conjugated compounds having a structure represented by any of the following General Formulas 2 to 3:

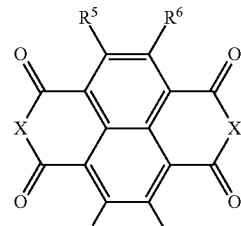

General formula 2

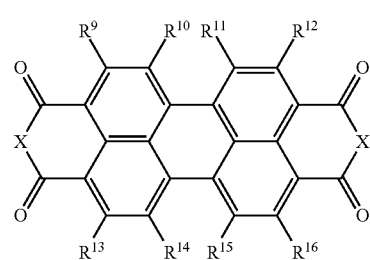

General formula 3 wherein Xs each independently represent O, and $R^5$ to $R^{16}$ each independently represent a hydrogen atom or a substituent; provided that at least one of $R^5$ to $R^{16}$ or at least one of $R^9$ to $R^{16}$ represents a group represented by the following General Formula 4:

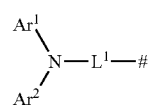

General formula 4 wherein $Ar^1$ and $Ar^2$ each independently represent a substituted or unsubstituted aryl group, $L^1$ represents a single bond or a substituted or unsubstituted arylene group, and # represents a bonding to the General Formulas 2 to 3; and $Ar^1$ and $Ar^2$ may form a ring structure via a single bond or a crosslinking group, wherein energy levels $S_1$ and $T_1$ of the assist dopant are lower than energy levels $S_1$ and $T_1$ of the host compound and higher than energy level $S_1$ of the luminescent compound, and wherein an amount of the fluorescence-emitting compound is 0.1 to 50% by mass ratio relative to the assist dopant.

2. The organic electroluminescent element according to claim 1,
wherein, in the General Formulas 2 to 3, at least two of $R^5$ to $R^8$ or at least two of $R^9$ to $R^{16}$ represent a group represented by the General Formula 4.

3. The organic electroluminescent element according to claim 1, wherein, in the General Formula 4, $L^1$ is an unsubstituted phenylene group.

4. The organic electroluminescent element according to claim 1,
wherein the group represented by the General Formula 4 is a group represented by any of the following General Formulas 5 to 8:

General formula 5

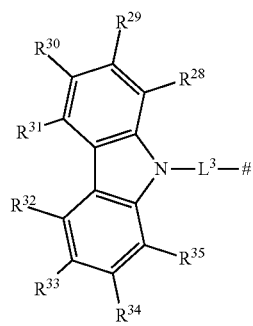

General formula 6

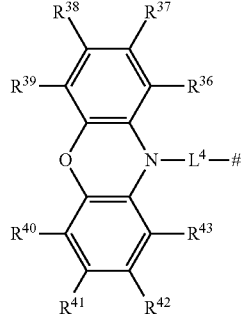

General formula 7

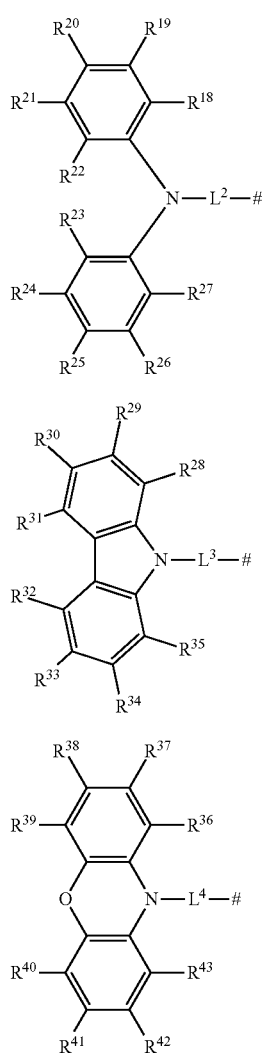

General formula 8

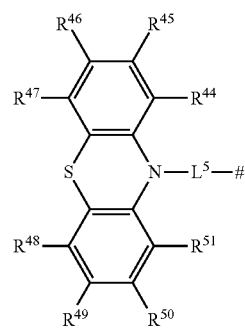

wherein $L^2$ to $L^5$ each independently represent a single bond or a substituted or unsubstituted arylene group, # represents a bonding to the General Formulas 2 to 3, and $R^{18}$ to $R^{27}$, $R^{28}$ to $R^{35}$, $R^{36}$ to $R^{43}$, and $R^{44}$ to $R^{51}$ each independently represent a hydrogen atom or a substituent; and $R^{18}$ and $R^{19}$, $R^{19}$ and $R^{20}$, $R^{20}$ and $R^{21}$, $R^{21}$ and $R^{22}$, $R^{23}$ and $R^{24}$, $R^{24}$ and $R^{25}$, $R^{25}$ and $R^{26}$, $R^{26}$ and $R^{27}$, $R^{28}$ and $R^{29}$, $R^{29}$ and $R^{30}$, $R^{30}$ and $R^{31}$, $R^{32}$ and $R^{33}$, $R^{33}$ and $R^{34}$, $R^{34}$ and $R^{35}$, $R^{36}$ and $R^{37}$, $R^{37}$ and $R^{38}$, $R^{38}$ and $R^{39}$, $R^{40}$ and $R^{41}$, $R^{41}$ and $R^{42}$, $R^{42}$ and $R^{43}$, $R^{44}$ and $R^{45}$, $R^{45}$ and $R^{46}$, $R^{46}$ and $R^{47}$, $R^{48}$ and $R^{49}$, $R^{49}$ and $R^{50}$, $R^{50}$ and $R^{51}$ may be bonded to each other to form a cyclic structure.

5. The organic electroluminescent element according to claim 1,
wherein $\Delta E_{ST}$ of the π-conjugated compound is 0.50 eV or less, the $\Delta E_{ST}$ being an absolute value of difference between the lowest singlet excited energy level and the lowest triplet excited energy level of the compound.

6. A display apparatus comprising the organic electroluminescent element according to claim 1.

7. A lighting apparatus comprising the organic electroluminescent element according to claim 1.

8. The organic electroluminescent element according to claim 1, wherein the fluorescence-emitting compound is selected from the group consisting of anthracene derivatives, pyrene derivatives, chrysene derivatives, fluoranthene derivatives, fluorene derivatives, arylacetylene derivatives, styrylarylene derivatives, styrylamine derivatives, arylamine derivatives, boron complexes, coumarin derivatives, pyrane derivatives, cyanine derivatives, croconium derivatives, squarylium derivatives, oxobenzanthracene derivatives, fluorescein derivatives, rhodamine derivatives, pyrylium derivatives, perylene derivatives, polythiophene derivatives, and rare earth complex-based compounds.

* * * * *